(12) United States Patent
Nielsen et al.

(10) Patent No.: US 7,157,079 B2
(45) Date of Patent: Jan. 2, 2007

(54) COMBINED TUMOR SUPPRESSOR GENE THERAPY AND CHEMOTHERAPY IN THE TREATMENT OF NEOPLASMS

(75) Inventors: Loretta Nielsen, Millington, NJ (US); Jo Ann Horowitz, Kenilworth, NJ (US); Daniel C. Maneval, San Diego, CA (US); G. William Demers, San Diego, CA (US)

(73) Assignee: Canji, Inc., San Diego, CA (US)

( * ) Notice: Subject to any disclaimer, the term of this patent is extended or adjusted under 35 U.S.C. 154(b) by 413 days.

(21) Appl. No.: 10/823,932

(22) Filed: Apr. 13, 2004

(65) Prior Publication Data

US 2005/0142112 A1   Jun. 30, 2005

Related U.S. Application Data

(63) Continuation of application No. 09/311,772, filed on May 13, 1999, now abandoned, which is a continuation of application No. 09/024,932, filed on Feb. 17, 1998, now abandoned.

(60) Provisional application No. 60/047,834, filed on May 28, 1997, provisional application No. 60/038,065, filed on Feb. 18, 1997.

(51) Int. Cl.
*A61K 31/41* (2006.01)
*A61K 48/00* (2006.01)
*C07D 401/14* (2006.01)
*C12N 15/861* (2006.01)

(52) U.S. Cl. .................. 424/93.2; 514/44; 514/290; 514/361; 435/320.1; 435/456; 435/375

(58) Field of Classification Search .............. None
See application file for complete search history.

(56) References Cited

U.S. PATENT DOCUMENTS

| 5,496,731 A | 3/1996 | Xu et al. |
| 5,747,469 A | 5/1998 | Roth et al. |
| 6,054,467 A | 4/2000 | Gjerset |
| 6,262,032 B1 | 7/2001 | Tocque |
| 6,316,462 B1 | 11/2001 | Bishop et al. |

FOREIGN PATENT DOCUMENTS

| EP | 0727486 | 8/1995 |
| EP | 0685493 | 12/1995 |
| WO | WO 94/06910 | 3/1994 |
| WO | WO 95/05738 | 3/1995 |
| WO | WO 95/10514 A1 | 4/1995 |
| WO | WO 95/11984 | 5/1995 |
| WO | WO 95/28948 A1 | 11/1995 |
| WO | WO 98/28948 A1 | 11/1995 |
| WO | WO 96/21456 | 7/1996 |
| WO | WO 97/23478 | 7/1997 |

OTHER PUBLICATIONS

Alberts, et al., (1997) "Safety aspects of Pegylated liposomal Doxyrubicin in Patients with Cancer," Drugs 54 Suppl. 4 30-35.
Allan, et al., *Scanning Microsc.* 2:503 (1988).
Allen, T. M., (1997) "Liposomes," Drugs 54 Suppl. 4 8-14.
Anderson, W.F., "Human gene therapy," *Nature* 392(6679 Suppl):25-30 (1998).
Baxter, et al., "Cell death by apoptosis in acute leukaemia." J Pathol. Jun. 1989;158(2):123-9.
Blagosklonny, et al., "In Vitro Evaluation of A *p*53-Expressing Adenovirus As An Anti-Cancer Drug," *Int. J. Cancer* 67:386-392 (1996).
Brinckerhoff, et al., Regulatory Issues: Dept. of Health and Human Services NIH Recombinant DNA Advisory Committee Minutes of Meeting. *Human Gene Therapy* 6(8): 1065-1124 (1995).
Bulinski J, et al. "Overexpression of MAP4 inhibits organelle motility and trafficking in vivo." J Cell Sci. Dec. 1997; 110(Pt 24): 3055-3064.
Chang, et al., "Restoration of the $G_1$ Checkpoint and the Apoptotic Pathway Mediated by Wild-type *p*53 Sensitizes Squamous Cell Carcinoma of the Head and Neck to Radiotherapy," *Arch Otolaryngol Head Neck Surg.*, 123:507-512 (1997).
Chen, et al., "Genetic mechanisms of tumor suppression by the human p53 gene." Science. Dec. 14, 1990;250(4987):1576-80.
Clarke, et al, "Thymocyte apoptosis induced by p53-dependent and independent pathways." Nature. Apr. 29, 1993;362(6423):849-52.
Clayman et al., "Adenovirus-mediated p53 gene transfer in patients with advanced recurrent head and neck squamous cell carcinoma," *Journal of Clinical Oncology* 16(6):2221-2232 (1998).
Columbano, et al., "Occurrence of cell death (apoptosis) in preneoplastic and neoplastic liver cells. A sequential study." Am J Pathol. Sep. 1984;116(3):441-6.

(Continued)

*Primary Examiner*—Scott D. Priebe
(74) *Attorney, Agent, or Firm*—Townsend and Townsend and Crew LLP

(57) ABSTRACT

In one embodiment, this invention provides methods of treating mammalian cancer or hyperproliferative cells, said method comprising contacting said cells with a tumor suppressor protein or tumor suppressor nucleic acid and also contacting said cell with at least one adjunctive anti-cancer agent. The invention also provides for a pharmacological composition comprising a tumor suppressor protein or a tumor suppressor nucleic acid and at least one adjunctive anti-cancer agent, and a kit for the treatment of mammalian cancer or hyperproliferative cells.

19 Claims, 13 Drawing Sheets

OTHER PUBLICATIONS

Dass CR, et al. "Enhanced anticancer therapy mediated by specialized liposomes." J Pharm Pharmacol. Oct. 1997; 49(10):972-975.

Delia, et al., "p53 Activity and Chemotherapy." *Nature Medicine* 2(7):724-725 (1996).

Denning C, et al. Bystander effects of different enzyme-prodrug systems for cancer gene therapy depend on different pathways for intercellular trans fer of toxic metabolites, a factor that will govern clinical choice of appropriate regimes. Hum Gene Ther. Oct. 10, 1997;8(15): 1825-1835.

Donehower, et al., *The Cancer Bulletin* 46:161 (1994), p. 165.

Drazan, et al., *Surgery* 116:197 (1994).

Frank, et al., "Combination *E2F-1* and *p53* Gene Transfer Does Not Enhance Growth Inhibition in Human Squamous Cell Carcinoma of the Head and Neck," *Clin. Cancer Research* 4:2265-2272 (1998).

Fujiwara, et al., (1994) Curr. Opin. Oncol. 6:96.

Fujiwara, et al., "Induction of chemosensitivity in human lung cancer cells *in Vivo* by adenovirus-mediated transfer of the wild-type p53 gene," *Cancer Research* 54:2287-2291 (1994).

Gallardo, et al., "Adenovirus-based Transfer of Wild-Type *p53* Gene Increases Ovarian Tumor Radiosensitivity," *Cancer Research* 56:4891-4893 (1996).

Gjerset, et al., "Use of Wild-Type *p53* to Achieve Complete Treatment Sensitization of Tumor Cells Expressing Endogenous Mutant p53," *Molecular Carcinogenesis* 14:275-285 (1995).

Gobe, et al., "Cell death by apoptosis following X-irradiation of the foetal and neonatal rat kidney." Int J Radiat Biol. Oct. 1988;54(4):567-76.

Gurnani, et al., "Adenovirus-mediated p53 gene therapy has greater efficacy when combined with chemotherapy against human head and neck, ovarian, prostate, and breast cancer," *Cancer Chemother Pharmacol.* 44:143-151 (1999).

Harris, Curtis C. et al., "Structure and function of the p53 tumor suppressor gene: clues for rational cancer therapeutic strategies," *Journal of the National Cancer Institute* 88(20):1442-1455 (1996).

Hehir et al., "Molecular characterization of replication-competent variants of adenovirus vectors and genome modifications to prevent their occurrence." *J Virol.* 70(12):8459-8467 (1996).

Ijiri, et al., "Apoptosis (cell death) induced in mouse bowel by 1,2-dimethylhydrazine, methylazoxymethanol acetate, and gamma-rays." Cancer Res. Nov. 15, 1989;49(22):6342-6.

Ijiri, et al., "Cell death (apoptosis) in mouse intestine after continuous irradiation with gamma rays and with beta rays from tritiated water." Radiat Res. Apr. 1989;118(1):180-91.

Kalechman, et al., "The antitumoral effect of the immunomodulator AS101 and paclitaxel (Taxol) in a murine model of lung adenocarcinoma." *J. Immunol.* 156(3):1101-1109 (1996.

Kianmanesh AR, et al., "A "distant" bystander effect of suicide gene therapy: regression of nontransduced tumors together with a distant transduced tumor." Hum Gene Ther. Oct. 10, 1997;8(15): 1807-1814.

Lanni, et al., p53-independent apoptosis induced by paclitaxel through an indirect mechanism. Proc Natl Acad Sci U S A. Sep. 2, 1997;94(18):9679-83.

Lechanteur C, et al. "HSV-1 thymidine kinase gene therapy for colorectal adenocarcinoma-derived peritoneal carcinomatosis." Gene Ther. Nov. 1997;4(11): 1189-1194.

Liu, et al., "Growth suppression of human head and neck cancer cells by the introduction of a wild-type p53 gene via a recombinant adenovirus." Cancer Res. Jul. 15, 1994;54(14):3662-7.

Lopes NM, et al. "Assessment of microtubule stabilizers by semiautomated in vitro microtubule protein polymerization and mitotic block assays." Cancer Chemother Pharmacol. 1997; 41(1): 37-47.

Lowe, et al., "p53-dependent apoptosis modulates the cytotoxicity of anticancer agents." Cell. Sep. 24, 1993;74(6):957-67.

Mallams AK, et al. "Antitumor 8-chlorobenzocycloheptapyridines: a new class of selective, nonpeptidic, nonsulfhydryl inhibitors of ras farnesylation." Bioorg Med Chem. Jan. 1997; 5(1): 93-99.

Muhlradt PF, et al. "Epothilone B stabilizes microtubuli of macrophages like taxol without showing taxol-like endotoxin activity." Cancer Res. Aug. 15 1997; 57(16): 3344-3346.

Nguyen, et al., "Gene therapy for lung cancer: enhancement of tumor suppression by a combination of sequential systemic cisplatin and adenovirus-mediated p53 gene transfer," *J. Thorac. Cardiavasc. Surg.* 112:1372-1377 (1996).

Nielsen and Maneval, "p53 tumor suppressor gene therapy for cancer," *Cancer Gene Therapy* 5(1):52-63 (1998).

Nielsen, et al. "Adenovirus-mediated *p53* Gene Therapy and Paclitaxel Have Synergistic Efficacy in Models of Human Head and Neck, Ovarian, Prostate, and Breast Cancer," *Clin. Cancer Research* 4:835-846 (1998).

Nielsen et al., "Combination therapy with the farnesyl protein transferase inhibitor SCH66336 and SCH58500 (p53 adenovirus) in preclinical cancer models," *Cancer Research* 59:5896-5901 (1999).

Nikiforov MA, et al. "Suppression of apoptosis by bcl-2 does not prevent p53-mediated control of experimental metastasis and anchorage dependence." Oncogene. Dec. 18, 1997; 15(25): 3007-3012.

Njoroge FG, et al. "Structure-activity relationship of 3-substituted N-(pyridinylacetyl)-4-(8-chloro -5,6-dihydro -11H-benzo[5,6]cyclohepta[1,2-b]pyridin-11-ylidene)- piperidine inhibitors of farnesyl-protein transferase: design and synthesis of in vivo active antitumor compounds." J Med Chem. Dec. 19, 1997; 40(26): 4290-4301.

Ogawa, et al., "Novel combination therapy for human colon cancer with adenovirus-mediated wild-type p53 gene transfer and DNA-damaging chemotherapeutic agent," *Int. J. Cancer* 73:367-370 (1997).

Ono Y, et al. "Regression of experimental brain tumors with 6-thioxanthine and *Escherichia coli* gpt gene therapy" Hum Gene Ther. Nov. 20, 1997; 8(17): 2043-2055.

Orkin and Motulsky, "Report and recommendations of the panel to assess the NIH investment in research on gene therapy" [online], Dec. 7, 1995.

Panda D, et al., "Stabilization of microtubule dynamics by estramustine by binding to a novel site in tubulin: a possible mechanistic basis for its antitumor action." Proc Natl Acad Sci U S A. Sep. 30, 1997; 94(20): 10560-10564.

Panda D, et al. "Differential effects of vinblastine on polymerization and dynamics at opposite microtubule ends." J Biol Chem. Nov. 22, 1996; 271(47): 29807-29812.

Parsels, et al., "Prevention of Fluorodeoxyuridine-Induced Cytotoxicity and DNA Damage in HT29 Colon Carcinoma Cells by Conditional Expression of Wild-Type p53 Phenotype," *Molecular Pharmacology* 52:600-605 (1997).

Pirollo, et al., "p53 mediated sensitization of squamous cell carcinoma of the head and neck to radiotherapy," *Oncogene*, 14:1735-1746 (1997).

Qazilbash MH, et al. "Cancer gene therapy using a novel adeno-associated virus vector expressing human wild-type p53." Gene Ther. Jul. 1997; 4(7): 675-682.

Rabinovitch A, et al. "Combination therapy with cyclosporine and interleukin-4 or interleukin-10 prolongs survival of synergeneic pancreatic islet grafts in nonobese diabetic mice." Transplantation. Dec. 15, 1997; 64(11): 1525-1531.

Reid et al., "Intravascular adenoviral agents in cancer patients: Lessons from clinical trials," *Cancer Gene Therapy* 9:979-986 (2002).

Roth et al., (1996) Modification of tumor suppressor gene expression and induction of apoptosis in non-small cell lung cancer (NSCLC) with an adenovirus vector expressing wildtype p53 and cisplatin. Hum Gene Ther. May 20, 1996;7(8):1013-30.

Roth, *Proc. Am. Ass'n Cancer Res.* 35:692 (1994).

Sarraf, et al., "Kinetic studies on a murine sarcoma and an analysis of apoptosis." Br J Cancer. Dec. 1986;54(6):989-98.

Sandig, et al., "Adenovirally transferred $p16^{INK4/CDKN2}$ and $p53$ genes cooperate to induce apoptotic tumor cell death," *Nature Med.*, 3:313-319 (1997).

Schuler et al., "A phase I study of adenovirus-mediated wild-type *p53* gene transfer in patients with advanced non-small cell lung cancer," *Human Gene Therapy* 9:2075-2082 (1998).

Seth, et al., "A recombinant adenovirus expressing wild type p53 induces apoptosis in drug-resistant human breast cancer cells: A gene therapy approach for drug-resistant cancers." Cancer Gene Ther. Nov.-Dec. 1997;4(6):383-90.

Shaw, et al.,. "Induction of apoptosis by wild-type p53 in a human colon tumor-derived cell line." Proc Natl Acad Sci U S A. May 15, 1992;89(10):4495-9.

Son, et al. "Exposure of human ovarian carcinoma to cisplatin transiently sensitizes the tumor cells for liposome-mediated gene transfer," *Proc. Natl. Acad. Sci. USA*, 91:12669-12672 (1994).

Spitz, et al., "Adenoviral-mediated Wild-Type *p53* Gene Expression Sensitizes Colorectal Cancer Cells to Ionizing Radiation," *Clin. Cancer Research* 2:1665-1671 (1996).

Spitz, et al., "*In Vivo* Adenovirus-Mediated p53 Tumor Suppressor Gene Therapy for Colorectal Cancer," *Anticancer Research*, 16:3415-3422 (1996).

Su H, et al. Tissue-specific expression of herpes simplex virus thymidine kinase gene delivered by adeno-associated virus inhibits the growth of human hepatocellular carcinoma in athymic mice. Proc Natl Acad Sci U S A. Dec. 9, 1997;94(25): 13891-13896.

Tishler and Lamppu, "The interaction of taxol and vinblastine with radiation induction of p53 and p21$^{WAF1/CIP1}$," *Br J Cancer* 74(Suppl XXVII):S82-S85 (1996).

Vasquez RJ, et al. "Nanomolar concentrations of nocodazole alter microtubule dynamic instability in vivo and in vitro." Mol Biol Cell. Jun. 1997; 8(6): 973-985.

Verma and Somia, "Gene therapy—promises, problems and prospects," *Nature* 389(6648):239-242 (1997).

Wahl et al., "Loss of normal p53 function confers sensitization to Taxol by increasing G2/M arrest and apoptosis," *Nature Medicine* 2(1): 72-79 (1996).

Weedon, et al., "Apoptosis. Its nature and implications for dermatopathology." Am J Dermatopathol. 1979 Summer;1(2):133-44. Review.

Wills et al., "Development and characterization of recombinant adenoviruses encoding human p53 for gene therapy of cancer," *Human Gene Therapy* 5:1079-1088 (1994).

Wiznerowicz M, et al. "Double-copy bicistronic retroviral vector platform for gene therapy and tissue engineering: application to melanoma vaccine development." Gene Ther. Oct. 1997; 4(10): 1061-1068.

Yeager TR, et al. "Overcoming cellular senescence in human cancer pathogenesis." Genes Dev. Jan. 15, 1998; 12(2): 163-174.

Yonish-Rouach, et al., "Wild-type p53 induces apoptosis of myeloid leukaemic cells that is inhibited by interleukin-6." Nature. Jul. 25, 1991;352(6333):345-7.

Zhang FL, et al. "Characterization of Ha-ras, N-ras, Ki-Ras4A, and Ki-Ras4B as in vitro substrates for farnesyl protein transferase and geranylgeranyl protein transferase type I." J Biol Chem. Apr. 11, 1997; 272(15): 10232-10239.

Tishler et al., Microtubule-active drugs taxol, vinblastine, and nocodazole increase the levels of transcriptionally active p53, Cancer Res. Dec. 15, 1995;55(24):6021-5.

Normal diploid fibroblast, MRC-9 cells, did not show more pronounced effects with combination treatment

COMBINED TUMOR SUPPRESSOR GENE THERAPY AND CHEMOTHERAPY IN THE TREATMENT OF NEOPLASMS

The present application is a continuation of application Ser. No. 09/311,772, filed May 13, 1999, now abandoned which is a continuation of application Ser. No. 09/024.932. filed Feb. 17, 1998, now abandoned which claims priority from U.S. Provisional Application No. 60/038,065, filed Feb. 18, 1997, now abandoned; and, U.S. Provisional Application No. 60/047,834, filed May 28, 1997, now abandoned. Each of the aforementioned applications is explicitly incorporated herein by reference in their entirety and for all purposes.

FIELD OF THE INVENTION

This invention describes novel methods of treating subjects afflicted with hyperproliferative diseases such as tumors or metastatic disease. In particular, this invention provides methods of inhibiting the hyperproliferation of cells, more specifically neoplastic cells, comprising the combined use of a tumor suppressor gene or gene product and an adjunctive anti-cancer agent.

BACKGROUND OF THE INVENTION

Chromosome abnormalities are often associated with genetic disorders, degenerative diseases, and cancer. In particular, the deletion or multiplication of copies of whole chromosomes or chromosomal segments, and higher level amplifications of specific regions of the genome are common occurrences in cancer. See, for example Smith (1991) *Breast Cancer Res. Treat.,* 18: Suppl. 1: 5–14; van de Viler (1991) *Became. Beefiest. Acta.* 1072: 33–50, Sato (1990) *Cancer. Res.,* 50: 7184–7189. In fact, the amplification of DNA sequences containing proto-oncogenes and the deletion of DNA sequences containing tumor-suppressor genes, are each frequently characteristic of tumorigenesis. Dutrillaux (1990) *Cancer Genet. Cytogenet.* 49: 203–217.

Mutation of the p53 gene is the most common genetic alteration in human cancers (Bartek (1991) *Oncogene* 6: 1699–1703, Hollstein (1991) *Science,* 253: 49–53). Moreover, introduction of wild-type p53 in mammalian cancer cells lacking endogenous wild-type p53 protein suppresses the neoplastic phenotype of those cells (see, e.g., U.S. Pat. No. 5,532,220).

Of the many available chemotherapeutic drugs, paclitaxel, available commercially as TAXOL® (NSC number: 125973) has generated interest because of its efficacy in clinical trials against drug-refractory tumors, including ovarian and mammary gland tumors (Hawkins (1992) *Oncology,* 6:17–23, Horwitz (1992) *Trends Pharmacol. Sci.* 13: 134–146, Rowinsky (1990) *J. Natl. Canc. Inst.* 82: 1247–1259). Recent studies on the interaction of paclitaxel and tumor suppressor gene therapy show that reduced levels of tumor suppressor (i.e., p53) correlated with increased G2/M phase arrest, micronucleation, and p53 independent paclitaxel-induced apoptosis. In contrast, surviving cells with intact p53 progressed through mitosis and transiently accumulated in the subsequent G1 phase, coincident with increased p53 and $p21^{Cip1,waf1}$ protein levels (Wahl (1996) *Nature Med.* 2:72–79). Similarly, Hawkins (1996) *Canc. Res.* 56: 892–898, showed that inactivation of p53 enhanced sensitivity to certain antimitotic agents including paclitaxel. The authors suggested that p53 may play a role in DNA repair, thereby allowing cells to progress more readily through S phase even in the presence of drugs. These studies thus suggest that tumor suppressor gene therapy and drug therapy with anti-mitotic agents (especially paclitaxel therapy) act at cross purposes.

SUMMARY OF THE INVENTION

This invention provides methods of treating hyperproliferative mammalian cells. The invention is premised, in part, on the surprising discovery that adjunctive anti-cancer agents in combination with tumor suppressor (e.g., p53) gene therapy provide an enhanced effect in inhibiting proliferation of neoplastic or other cells having deficient tumor suppressor activity.

Thus, in one embodiment, this invention provides methods of treating cancer or hyperproliferative cells by contacting the cells with a tumor suppressor protein or tumor suppressor nucleic acid and with at least one adjunctive anti-cancer agent. In some embodiments, the methods include co-administration of the tumor suppressor protein or nucleic acid and the adjunctive anti-cancer agent with at least one chemotherapeutic agent. For example, a tumor suppressor nucleic acid (e.g., a nucleic acid encoding p53) can be administered with an adjunctive anti-cancer agent (e.g., paclitaxel) and a DNA damaging agent such as cisplatin, carboplatin, navelbine (vinorelbine tartate).

The cancer or hyperproliferative cells are often neoplastic cells. When the cells are present in a tumor the method inhibits tumor growth and thereby provides a method of treating a cancer. Such cancers include, but are not limited to, an ovarian cancer, pancreatic cancer, a non-small cell lung cancer, small cell lung cancer, hepatocarcinoma, melanoma, retinoblastoma, breast tumor, colorectal carcinoma, leukemia, lymphoma, brain tumor, cervical carcinoma, sarcoma, prostate tumor, bladder tumor, tumor of the reticuloendothelial tissues, Wilm's tumor, astrocytoma, glioblastoma, neuroblastoma, ovarian carcinoma, osteosarcoma, renal cancer, or head and neck cancer.

A preferred adjunctive anti-cancer agent is paclitaxel or a paclitaxel derivative while a preferred tumor suppressor nucleic acid is a nucleic acid that encodes a tumor suppressor protein selected from the group consisting of p53 protein and its analogues, and a retinoblastoma (RB) protein. A particularly preferred tumor suppressor nucleic acid encodes a wild-type p53 protein and a particularly preferred retinoblastoma protein is a $p110^{RB}$ or a $p56^{RB}$.

The tumor suppressor nucleic acid is preferably delivered to the target cell by a vector. Such vectors' viruses have been modified by recombinant DNA technology to enable the expression of the tumor suppressor nucleic acid in the target cell. These vectors may be derived from vectors of non-viral (e.g., plasmids) or viral (e.g., adenovirus, adenoassociated virus, retrovirus, herpes virus, vaccinia virus) origin. In the preferred practice of the invention, the vector is a recombinantly modified adenoviral vector. Non-viral vectors are preferably complexed with agents to facilitate the entry of the DNA across the cellular membrane. Examples of such non-viral vector complexes include the formulation with polycationic agents which facilitate the condensation of the DNA and lipid-based delivery systems. An example of a lipid-based delivery system would include liposome based delivery of nucleic acids.

Particularly suitable adenoviral vectors (e.g., for delivery of a nucleic acid encoding a wild-type p53 protein) comprise a partial or total deletion of a protein IX DNA. In one embodiment, the deletion of the protein IX gene sequence extends from about 3500 bp from the 5' viral termini to about 4000 bp from the 5' viral termini. The vector may also comprise a deletion of a non-essential DNA sequence in adenovirus early region 3 and/or in adenovirus early region 4 and in one embodiment the deletion is the DNA sequence E1a and/or E1b. A particularly preferred recombinant adenoviral vector for delivery of a human p53 cDNA comprises the adenovirus type 2 major late promoter or the human CMV promoter, and the adenovirus type 2 tripartite leader cDNA. One such preferred adenoviral vector is ACN53.

Preferred paclitaxel or paclitaxel derivatives include paclitaxel (sold under the trademark TAXOL®) and/or TAXOLERE® (docetaxel) with paclitaxel (TAXOL®) being most preferred. Another preferred adjunctive anti-cancer is Epothilone. In one particularly preferred embodiment, the tumor suppressor is A/C/N/53 and the adjunctive anti-cancer agent is paclitaxel.

The tumor suppressor protein or tumor suppressor nucleic acid can be dispersed in a pharmacologically acceptable excipient. Similarly, the adjunctive anti-cancer (e.g., paclitaxel or paclitaxel derivative) can be dispersed in a pharmacologically acceptable excipient. The tumor suppressor protein or tumor suppressor nucleic acid and said paclitaxel or paclitaxel derivative can both be dispersed in a single composition (comprising one or multiple excipient(s)).

The tumor suppressor (protein or nucleic acid) and/or the adjunctive anti-cancer can be administered intra-arterially, intravenously (e.g., injected), intraperitoneally and/or intra-tumorally, together or sequentially. Preferred sites of administration include intra-hepatic-artery, intraperitoneal, or, where it is desired to treat cells in the head (e.g, neurological cells), into the carotid system of arteries.

The tumor suppressor protein or nucleic acid can be administered in a single dose or a multiplicity of treatments, e.g., each separated by at least about 6 hours, more preferably in least three treatments separated by about 24 hours.

In another preferred embodiment, the tumor suppressor protein or tumor suppressor nucleic acid is administered (with or without an adjunctive anti-cancer agent) in a total dose ranging from about $1 \times 10^9$ to about $1 \times 10^{14}$, or about $1 \times 10^9$ to about $7.5 \times 10^{15}$, preferably about $1 \times 10^{11}$ to about $7.5 \times 10^{13}$, adenovirus particles in a treatment regimen selected from the group consisting of: the total dose in a single dose, the total dose administered daily over 5 days, the total dose administered daily over 15 days, and the total dose administered daily over 30 days. The dose can also be administered continuously for 1 to 30 days. The paclitaxel or paclitaxel derivative is administered in a total dose ranging from 75–350 mg/m$^2$ over 1 hour, 3 hours, 6 hours, or 24 hours in a treatment regimen selected from the group consisting of administration in a single dose, in the total dose administered daily on each of day 1 and day 2, in the total dose administered daily on each of day 1, day 2, and day 3, on a daily dosage for 15 days, on a daily dosage for 30 days, on daily continuous infusion for 15 days, on daily continuous infusion for 30 days. A preferred dose is 100–250 mg/m$^2$ in 24 hours. Alternatively, the paclitaxel or derivative can be administered weekly at 60 mg/m$^2$. This method of administration can be repeated for two or more cycles (more preferably for three cycles) and the two or more cycles are can be spaced apart by three or four weeks.

In some preferred embodiments, a daily dose in the range of $7.5 \times 10^9$ to about $7.5 \times 10^{15}$, preferably about $1 \times 10^{12}$ to about $7.5 \times 10^{13}$, adenovirus particles can be administered each day for up to 30 days (e.g., a regimen of 2 days or 2 to 5 days or 14 days or 30 days with the same dose being administered each day). The multiple regimen can be repeated in recurring cycles of 21 to 28 days. Preferred routes of administration include intra-arterial (e.g., intra-hepatic artery), intratumorally, and intraperitoneally.

When the tumor suppressor nucleic acid (e.g., p53) is administered in an adenoviral vector with an adjunctive anti-cancer agent (e.g., paclitaxel) and a DNA damaging agent (e.g., cisplatin, carboplatin, or navelbine), the adenoviral vector is administered for 5–14 days at about $7.5 \times 10^{12}$ to about $7.5 \times 10^{13}$ adenoviral particles per day. If the adenoviral vector and paclitaxel is administered with carboplatin, the dose is typically $7.5 \times 10^{13}$ adenoviral particles per day. For example, a daily dose of about $7.5 \times 10^{12}$ adenoviral particles can be used for administration to the lung.

This invention also provides for kits for the treatment of mammalian cancer or hyperproliferative cells. The kits include a tumor suppressor protein or nucleic acid described herein (more preferably a wild-type p53 protein or nucleic acid (e.g., in a viral or non-viral vector), or a retinoblastoma (RB) protein or nucleic acid); and an adjunctive anti-cancer agent described herein (e.g., paclitaxel or a paclitaxel derivative) and/or optionally any of the other chemotherapeutic agents described herein. The kit can optionally further include instructions describing the administration of both the tumor suppressor protein or nucleic acid and the adjunctive anti-cancer agent (and optionally an other chemotherapeutic agent) to inhibit the growth or proliferation of the cancer or hyperproliferative cells. One particularly preferred kit includes A/C/N/53 and paclitaxel.

In another embodiment this invention provides pharmacological compositions comprising a tumor suppressor protein or a tumor suppressor nucleic acid and an adjunctive anti-cancer agent. In various embodiments, the pharmacological composition can optionally include any of the other chemotherapeutic compounds described herein. One particularly preferred composition includes a p53 nucleic acid (e.g., A/C/N/53) and paclitaxel. The tumor suppressor nucleic acid or protein and the chemotherapeutic agent (e.g., paclitaxel) can be in different excipients or can be contained in a single excipient as described herein. Where there are multiple excipients, the excipients can be intermixed or held separately (e.g., as in microcapsules).

In still another embodiment, this invention provides a composition comprising a mammalian cancer or hyperproliferative cell, wherein said cell contains an exogenous tumor suppressor nucleic acid or a tumor suppressor protein. The cell may additionally include an adjunctive anti-cancer agent such as paclitaxel or a paclitaxel derivative. The exogenous tumor suppressor nucleic acid or tumor suppressor protein may be any one or more of the tumor suppressor nucleic acids and/or proteins described herein. Similarly the cell can be any one or more of the hyperproliferative and/or cancerous cells described herein.

In yet another embodiment, this invention provides a method of treating a metastatic cell. The method involves contacting the cell with a tumor suppressor nucleic acid or tumor suppressor polypeptide. Suitable tumor suppressor nucleic acids or polypeptides include any of the tumor suppressors nucleic acids and/or polypeptides disclosed herein. The method can additionally include contacting the cell with any of the the adjunctive anti-cancer agents disclosed herein. In a particularly preferred embodiment, the method involves topical administration of the tumor suppressor nucleic acid and/or polypeptide to a surgical wound.

In another embodiment, this invention provides particularly preferred dosage regimen. Thus, in one embodiment, this invention provides a method of treating mammalian cells, where the method involves administering to the cells a total dose of a tumor suppressor protein or tumor suppressor nucleic acid, wherein said total dose is administered in a multiplicity of administrations of incremental doses of said tumor suppressor protein or tumor suppressor nucleic acid. Preferred multiple administrations are each separated by at least about 6 hours. One preferred administration is in least three treatments separated by about 24 hours.

In another embodiment, this invention provides a method of treating a mammalian cell. The method involves administering to the cell a total dose of a tumor suppressor protein or tumor suppressor nucleic acid, wherein the total dose is administered in a multiplicity of administrations of incremental doses of tumor suppressor protein or tumor suppressor nucleic acid. The administrations may be spaced by at least about six hours. The method can involve at least comprising at least three incremental doses and the doses can be administered daily. In one embodiment, the method can comprise at least three treatments separated by about 24 hours. In another embodiment the method can involve tumor administering the tumor suppressor nucleic acid is administered in a total dose ranging from about $1 \times 10^9$ to about $7.5 \times 10^{15}$, or about $1 \times 10^{11}$ to about $7.5 \times 10^{13}$, adenovirus particles in a treatment regimen selected from the group consisting of: the total dose in a single dose, the total dose administered daily over 5 days, the total dose administered daily over 15 days, and the total dose administered daily over 30 days. The method may further comprise administering paclitaxel or a paclitaxel derivative in a total dose ranging from about 75 mg/m$^2$ to about 350 mg/m$^2$ over 24 hours in a treatment regimen selected from the group consisting of administration in a single dose, in a dose administered daily on day 1 and day 2, in a dose administered daily on day 1, day 2, and day 3, on a daily dosage for 15 days, on a daily dosage for 30 days, on daily continuous infusion for 15 days, on daily continuous infusion for 30 days. These treatment regimens may be is repeated for two or more cycles and the two or more cycles can be spaced apart by three or four weeks. The cells thus treated include neoplastic cells comprising a cancer selected from the group consisting of an ovarian cancer, mesothelioma, pancreatic cancer, a non-small cell lung cancer, small cell lung cancer, hepatocarcinoma, melanoma, retinoblastoma, breast tumor, colorectal carcinoma, leukemia, lymphoma, brain tumor, cervical carcinoma, sarcoma, prostate tumor, bladder tumor, tumor of the reticuloendothelial tissues, Wilm's tumor, astrocytoma, glioblastoma, neuroblastoma, osteosarcoma, renal cancer, and head and neck cancer. The treatment treating preferably results in inhibition of growth or proliferation of a tumor as assayed by measurement of the volume of the tumor.

The invention also provides for a pharmacological composition comprising a tumor suppressor protein or a tumor suppressor nucleic acid and at least one adjunctive anti-cancer agent. The adjunctive anti-cancer agent can be paclitaxel or a paclitaxel derivative. The tumor suppressor protein or tumor suppressor nucleic acid can be selected from the group consisting of a nucleic acid that encodes a wild-type p53 protein, a nucleic acid that encodes a retinoblastoma (RB) protein, a wild-type p53 protein, and a retinoblastoma (RB) protein.

The retinoblastoma protein can be p110$^{RB}$ or a p56$^{RB}$. The nucleic acid can be contained in a recombinant adenoviral vector. The nucleic acid can be contained in a recombinant adenoviral vector comprising a partial or total deletion of a protein IX DNA and comprising a nucleic acid encoding a P53 protein. In one embodiment, the deletion of the protein IX gene sequence can extend from about 3500 bp for the 5' viral termini to about 4000 bp from the 5' viral termini. The deletion of DNA can include sequence designated E1a and E1b. The recombinant adenoviral vector can further comprise the adenovirus type 2 major late promoter or the human CMV promoter, the adenovirus type 2 tripartite leader cDNA and a human p53 cDNA. In a preferred embodiment, the vector is A/C/N/53. The composition can be paclitaxel, or a paclitaxel derivative or a paclitaxel analogue.

The invention further provides for a composition comprising a mammalian cancer or hyperproliferative cell, wherein said cell contains an exogenous a tumor suppressor nucleic acid or a tumor suppressor protein and an adjunctive anti-cancer agent. The tumor suppressor nucleic acid can be a nucleic acid that encodes a tumor suppressor protein selected from the group consisting of wild-type p53 protein, and a retinoblastoma (RB) protein. The retinoblastoma protein can be a p110$^{RB}$ or a p56$^{RB}$. The cells can be present in a mammal. The cells can be neoplastic cells and the neoplastic cells can comprise a cancer selected from the group consisting of an ovarian cancer, pancreatic cancer, a non-small cell lung cancer, small cell lung cancer, hepatocarcinoma, melanoma, retinoblastoma, breast tumor, colorectal carcinoma, leukemia, lymphoma, brain tumor, cervical carcinoma, sarcoma, prostate tumor, bladder tumor, tumor of the reticuloendothelial tissues, Wilm's tumor, astrocytoma, glioblastoma, neuroblastoma, osteosarcoma, renal cancer, and head and neck cancer.

The invention provides for a method of treating a metastatic cell, said method comprising contacting said cell with a tumor suppressor nucleic acid or tumor suppressor polypeptide and an adjunctive anti-cancer agent. The contacting can comprise topical administration of a tumor suppressor nucleic acid to a surgical wound. The method can further include co-administration of a chemotherapeutic agent, and the chemotherapeutic agent can be cisplatin, carboplatin, or navelbine.

DEFINITIONS

The term "adjunctive anti-cancer agent" refers to an agent which has at least one of the following activities: the ability to modulate of microtubule formation or action, the ability to inhibit polyprenyl-protein transferase activity, the ability to inhibit angiogenesis, or the ability to inhibit endocrine activity. Adjunctive anti-cancer agents useful in the invention are described in more detail below. As used herein, adjunctive anti-cancer agents of the invention do not include compounds with DNA damaging activity.

"Tumor suppressor genes' are nucleic acids for which loss-of-function mutations are oncogenic. Thus, the absence, mutation, or disruption of normal expression of a tumor suppressor gene in an otherwise healthy cell increases the likelihood of, or results in, the cell attaining a neoplastic state. Conversely, when a functional tumor suppressor gene or protein is present in a cell, its presence suppresses the tumorigenicity, malignancy or hyperproliferative phenotype of the host cell. Examples of tumor suppressor nucleic acids within this definition include, but are not limited to p110$^{RB}$, p56$^{RB}$, p53, and other tumor suppressors described herein and in copending application U.S. Ser. No. 08/328,673 filed on Oct. 25, 1994. Tumor suppressor nucleic acids include tumor suppressor genes, or nucleic acids derived therefrom (e.g., cDNAs, cRNAs, mRNAs, and subsequences thereof encoding active fragments of the respective tumor suppressor polypeptide), as well as vectors comprising these sequences.

A "tumor suppressor polypeptide or protein" refers to a polypeptide that, when present in a cell, reduces the tumorigenicity, malignancy, or hyperproliferative phenotype of the cell.

The term "viral particle" refers to an intact virion. The concentration of infectious adenovirus viral particles is typically determined by spectrophotometric detection of DNA, as described, for instance, by Huyghe (1995) *Human Gene Ther.* 6:1403–1416.

The terms "neoplasia" or "neoplastic" are intended to describe a cell growing and/or dividing at a rate beyond the normal limitations of growth for that cell type.

The term "tumorigenic" or "tumorigenicity" are intended to mean having the ability to form tumors or capable of causing tumor formation.

The phrase "treating a cell" refers to the inhibition or amelioration of one or more disease characteristics of a diseased cell. When used in reference to a cancer cell that is neoplastic (e.g., a mammalian cancer cell lacking an endogenous wild-type tumor suppressor protein), the phrase "treating a cell" refers to mitigation or elimination of the neoplastic phenotype. Typically such treatment results in inhibition (a reduction or cessation of growth and/or proliferation) of the cell as compared to the same cell under the same conditions but for the treatment (e.g., adjunctive anti-cancer agent and or tumor suppressor nucleic acid or polypeptide). Such inhibition may include cell death (e.g., apoptosis). These terms when used with reference to a tumor refer to inhibition of growth or proliferation of the tumor mass (e.g., as measured volumetrically). Such inhibition may be mediated via reduction in growth rate and/or proliferation rate and/or death of cells comprising the tumor mass. The inhibition of growth or inhibition of proliferation can be accompanied by an alteration in cellular phenotype (e.g., restoration of morphology characteristic of healthy cells, restoration of contact inhibition, loss of invasive phenotype, inhibition of anchorage independent growth, etc.). For the purposes of this disclosure, a diseased cell will have one or more pathological traits. These traits in a diseased cell may include, inter alia, defective expression of one or more tumor suppressor proteins. Defective expression may be characterized by complete loss of one or more functional tumor suppressor proteins or a reduction in the level of expression of one or more functional tumor suppressor proteins. Such cells are often neoplastic and/or tumorigenic.

The term "systemic administration" refers to administration of a composition or drug, such as the recombinant adenoviral vectors of the invention or the adjunctive anti-cancer or chemotherapeutic compounds described herein, in a manner that results in the introduction of the composition or drug into the circulatory system. The term "regional administration" refers to administration of a composition or drug into a specific anatomical space, such as intraperitoneal, intrathecal, subdural, or to a specific organ, and the like. For example, regional administration includes administration of the composition or drug into the hepatic artery for regional administration to the liver. The term "local administration" refers to administration of a composition or drug into a limited, or circumscribed, anatomic space, such as intratumoral injection into a tumor mass, subcutaneous injections, intramuscular injections, and the like. Any one of skill in the art would understand that local administration or regional administration may also result in entry of the composition or drug into the circulatory system.

The term "reduced tumorigenicity" is used herein to refer to the conversion of hyperproliferative (e.g. neoplastic) cells to a less proliferative state. In the case of tumor cells, "reduced tumorigenicity" is intended to mean tumor cells that have become less tumorigenic or non-tumorigenic or non-tumor cells whose ability to convert into tumor cells is reduced or eliminated. Cells with reduced tumorigenicity either form no tumors in vivo or have an extended lag time of weeks to months before the appearance of in vivo tumor growth. Cells with reduced tumorigenicity may also result in slower growing three dimensional tumor mass compared to the same type of cells having fully inactivated or non-functional tumor suppressor gene growing in the same physiological milieu (e.g., tissue, organism age, organism sex, time in menstrual cycle, etc.).

As used herein an "active fragment" of a gene or polypeptide includes smaller portion(s) (subsequences) of the gene or nucleic acid derived therefrom (e.g., cDNA) that retain the ability to encode proteins having tumor suppressing activity. Similarly, an active fragment of a polypeptide refers to a subsequence of a polypeptide that has tumor suppressing protein. One example of an active fragment is $p56^{RB}$ as described, e.g., in copending U.S. Ser. No. 08/328,673 filed on Oct. 25, 1994.

The term "malignancy" is intended to describe a tumorigenic cell having the ability to metastasize.

"Nucleic acids", as used herein, may be DNA or RNA. Nucleic acids may also include modified nucleotides that permit correct read through by a polymerase and do not alter expression of a polypeptide encoded by that nucleic acid.

The phrase "nucleotide sequence" includes both the sense and antisense strands as either individual single strands or in the duplex.

The phrase "DNA sequence" refers to a single or double stranded DNA molecule composed of the nucleotide bases, adenosine, thymidine, cytosine and guanosine.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It being further understood that the sequence includes the degenerate codons of the native sequence or sequences which may be introduced to provide codon preference in a specific host cell.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

"Isolated" or "substantially pure" when referring to nucleic acid sequences encoding tumor suppressor protein or polypeptide or fragments thereof refers to isolated nucleic acids which do not encode proteins or peptides other than the tumor suppressor protein or polypeptide or fragments thereof.

The term "recombinant" refers to DNA which has been isolated from its native or endogenous source and modified either chemically or enzymatically to delete naturally-occurring flanking nucleotides or provide flanking nucleotides that do not naturally occur. Flanking nucleotides are those nucleotides which are either upstream or downstream from the described sequence or sub-sequence of nucleotides.

A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). It is recognized that vectors often include an expression cassette placing the nucleic acid of interest under the control of a promoter. Vectors include, but are not limited to replicons (e.g., plasmids, bacteriophages) to which fragments of DNA may be attached and become replicated. Vectors thus include, but are not limited to RNA, autonomous self-replicating circular DNA (plasmids), and includes both the expression and nonexpression plasmids. Where a recombinant microorganism or cell culture is described as hosting an "expression vector" this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term effective amount is intended to mean the amount of vector or drug which achieves a positive outcome on controlling cell growth and/or proliferation.

The abbreviation "C.I.U." as used herein, stands for "cellular infectious units." The C.I.U. is calculated by measuring viral hexon protein positive cells (e.g., -293 cells) after a 48 hr. infection period (Huyghe (1995) *Human Gene Ther.* 6:1403–1416).

The abbreviation "m.o.i." as used herein refers to "multiplicity of infection" and is the C.I.U. per cell.

The term "paclitaxel" as used herein refers to the drug commercially known as TAXOL®. TAXOL® inhibits eukaryotic cell replication by enhancing polymerization of tubulin moieties into stabilized microtubule bundles that are unable to reorganize into the proper structures for mitosis.

The term "contacting a cell" when referring to contacting with a drug and/or nucleic acid is used herein to refer to contacting in a manner such that the drug and/or nucleic acid is internalized into the cell. In this context, contacting a cell with a nucleic acid is equivalent to transfecting a cell with a nucleic acid. Where the drug is lipophilic or the nucleic acid is complexed with a lipid (e.g., a cationic lipid) simple contacting will result in transport (active, passive and/or diffusive) into the cell. Alternatively the drug and/or nucleic acid may be itself, or in combination with a carrier composition be actively transported into the cell. Thus, for example, where the nucleic acid is present in an infective vector (e.g., an adenovirus) the vector may mediate uptake of the nucleic acid into the cell. The nucleic acid may be complexed to agents which interact specifically with extracellular receptors to facilitate delivery of the nucleic acid into the cell, examples include ligand/polycation/DNA complexes as described in U.S. Pat. Nos. 5,166,320 and 5,635,383. Additionally, viral delivery may be enhanced by recombinant modification of the knob or fiber domains of the viral genome to incorporate cell targeting moieties.

The constructs designated herein as "A/C/N/53", "A/M/N/53", $p110^{RB}$, $p56^{RB}$, refer to the constructs so designated in copending application U.S. Ser. No. 08/328,673, filed on Oct. 25, 1994, International Application WO 95/11984.

A "conservative substitution", when describing a protein refers to a change in the amino acid composition of the protein that does not substantially alter the protein's activity. Thus, uconservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. For example, the following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Proteins* W.H. Freeman and Company. In addition, individual substitutions, deletions or additions which alter, add or delete a single amino acid or a small percentage of amino acids in an encoded sequence are also "conservatively modified variations".

BRIEF DESCRIPTION OF THE DRAWINGS

FIG. 3a illustrates results with MDA-MB-231 tumors. FIG. 3b illustrates results with MDA-MB-468 (-468) tumors, and FIG. 3c illustrates results with MDA-MB-435 (-435) tumors.

DETAILED DESCRIPTION

Figure 1:
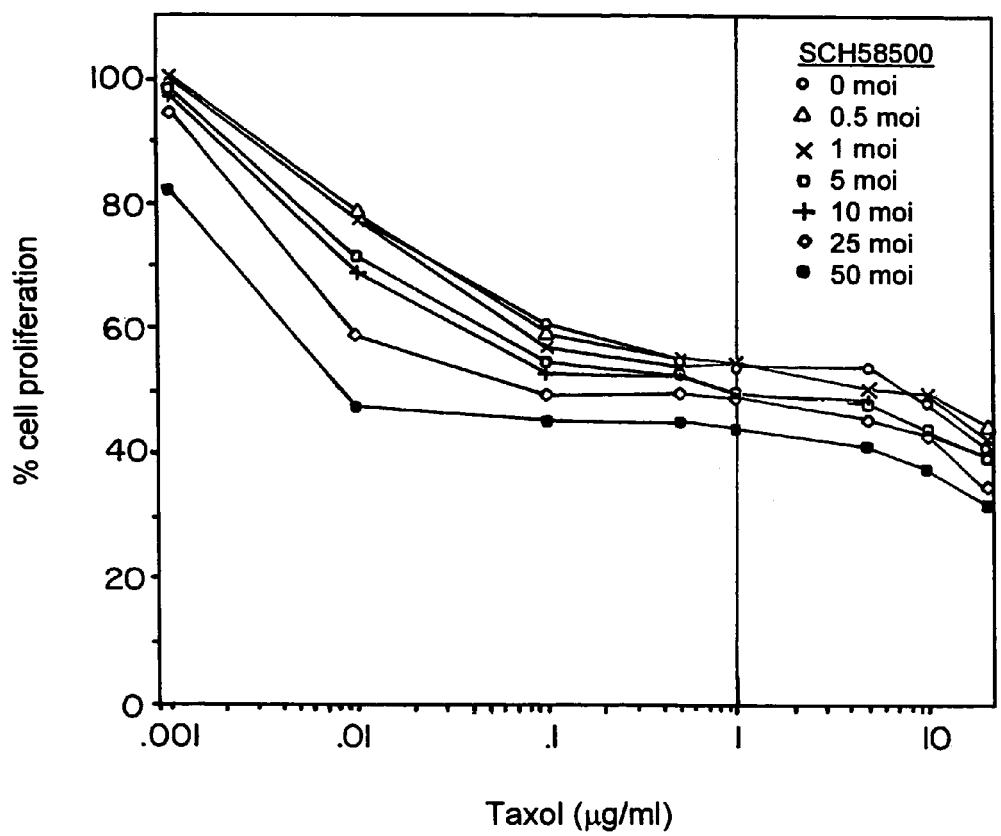
FIG. 1 illustrates the in vitro inhibition of SK-OV-3 ovarian tumor cells by various concentrations of p53 (A/C/N/53) and/or TAXOL®.

This invention provides new methods of inhibiting the growth and/or proliferation of cells, more particularly the growth and proliferation of cancer cells. In one embodiment, the methods involve contacting the cells with a tumor suppressor nucleic acid, or tumor suppressor protein and with an adjunctive anti-cancer agent. Typically, the tumor suppressor protein or nucleic acid used will be the same species as the tumor suppressor protein that is lacking. Thus, where the cell lacks endogenous p53 activity, a p53 protein or p53 nucleic acid will be used.

It was a surprising discovery of this invention that, contrary to the results described in previous studies (see, e.g., Wahl et al. (1996) Nature Med., 2(1): 72–79, and Hawkins et al. (1996) Canc. Res. 56: 892–898), the treatment of mammalian cells lacking or deficient in endogenous wild-type tumor suppressor protein (i.e., many neoplastic cells), with both an adjunctive anti-cancer agent (e.g., paclitaxel (TAXOL®)) and a tumor suppressor gene or polypeptide (e.g., p53) results in inhibition of proliferation and/or growth of the cells greater than that observed with either the chemical treatment or the tumor suppressor construct alone. Moreover, it was a discovery of this invention that pretreatment with adjunctive anti-cancer agents dramatically increases the anti-proliferative effect of a tumor suppressor nucleic acid. Without being bound by a particular theory, it is believed that possible means by which an adjunctive anti-cancer agent may contribute to this enhanced effect is: to increase the transfection efficiency of various gene therapy vectors (e.g., adenovirus vectors); or, to increase expression levels of the tumor suppressor gene; or, to stabilize microtubules to assist in intracellular virus transport; or, to provide enhanced effect through the interaction of various intracellular mechanisms (e.g., signaling pathways, apoptotic pathways, cell cycling pathways).

Thus, in one embodiment, this invention provides methods of inhibiting diseased mammalian cells lacking, or deficient in, an endogenous wild-type tumor suppressor protein of cells by contacting them with an adjunctive anti-cancer agent and with a tumor suppressor nucleic acid and/or tumor suppressor polypeptide. When the cells are present in a tumor the method inhibits tumor growth and thereby provides a method of treating a cancer. Particularly preferred tumor suppressor nucleic acids or polypeptides include p53, RB, h-NUC (see, e.g., Chen (1995) Cell Growth Differ. 6:199–210) or active fragments thereof (e.g., p110RB, p56RB), while particularly preferred adjunctive anti-cancer agents (compounds) include paclitaxel and compounds with paclitaxel-like activity such as paclitaxel derivatives (e.g., analogues).

It was also a discovery of this invention that contacting of cells with a tumor suppressor nucleic acid and/or polypeptide can inhibit metastatic cells. Such inhibition can take the form of inhibition of the formation, growth, migration, or reproduction of metastatic cells. In one embodiment, the inhibition can be characterized by the inhibition (e.g., reduction and/or elimination) in the appearance of neoplasms remote from the primary tumor. This invention thus provides methods for treating (mitigating or eliminating) the progression of metastatic disease. The methods involve contacting metastatic cells with a tumor suppressor nucleic acid and/or polypeptide. In a particularly preferred embodiment, this method may involve contacting the cells in a surgical wound site (e.g., after removal (debulking) of a tumor mass) with a tumor suppressor nucleic acid and/or tumor suppressor polypeptide in combination with adjunctive anticancer agent. The cells can additionally be contacted with an adjunctive anti-cancer agent as described herein.

In still another embodiment, this invention provides for advantageous treatment regimens utilizing tumor suppressor genes and gene products. In part, these treatment regimens are based on the surprising discovery that tumor suppressor nucleic acids and/or polypeptides are more effective in inhibiting cell or tumor growth when delivered in multiple administrations rather than in a single bolus.

The order in which the tumor suppressor and adjunctive anti-cancer agents are administered is not critical to the invention. Thus the composition(s) can be administered simultaneously or sequentially. For instance, in one embodiment, pretreatment of a cell with at least one adjunctive anti-cancer agent (alone or in combination with a chemotherapeutic agent) increases the efficacy of a subsequently administered tumor suppressor nucleic acid and/or polypeptide. In one embodiment, the chemotherapeutic agent is administered before the adjunctive anti-cancer agent and the tumor suppressor nucleic acid and/or polypeptide. In another embodiment, the adjunctive anti-cancer agent (alone or in combination with a chemotherapeutic agent) is administered simultaneously with the tumor suppressor nucleic acid and/or polypeptide. In a further embodiment, the tumor suppressor nucleic acid and/or polypeptide is administered after the tumor suppressor nucleic acid and/or polypeptide.

The anti-tumor effect of administering the composition and methods of the invention also includes an anti-tumor, non-specific effect, the so-called "bystander effect," (see, e.g., Zhang (1996) Cancer Metastasis Rev. 15:385–401 and Okada (1996) Gene Ther. 3:957–96). Furthermore, the immune system can also be manipulated to selectively accentuate (or depress) the humoral or the cellular arm of the immune system, i.e., modulate the B cell and/or T cell (e.g., a cytotoxic lymphocyte (CTL) or tumor infiltrating lymphocyte (TIL)) response. For example, an increase in TILs is observed upon administration of a p53-expressing adenovirus to humans. Specifically, an increase in TILs (phenotypically T helper cells, $CD3^+$ and $CD4^+$) is observed upon intra-hepatic arterial administration of a p53-expressing adenovirus for the treatment of metastatic hepatic carcinoma, as described in detail below.

It is recognized that the methods of this invention are not restricted to the use of a single adjunctive anti-cancer agent or even the use of a single chemotherapeutic. Thus this invention provides for methods of inhibiting diseased mammalian cells lacking an endogenous tumor suppressor protein, or a tumor comprising such cells, by contacting the cells or tumor with a tumor suppressor nucleic acid and one or more adjunctive anti-cancer agent as described herein.

I. Adjunctive Anti-Cancer Agents
   A) Microtubule Affecting Agents

As explained above, in one embodiment, this invention provides methods of inhibiting diseased cells lacking an endogenous tumor suppressor protein by contacting the cells with a tumor suppressor protein or tumor suppressor nucleic acid and an adjunctive anticancer agent such as a microtubule affecting agent (e.g., paclitaxel, a paclitaxel derivative or a paclitaxel-like compound). As used herein, a microtubule affecting agent is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (TAXOL®, NSC 125973), TAXOL® derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) *Science*, 274: 2009) estramustine, nocodazole, MAP4, and the like. Examples of such agents are also described in the scientific and patent literature, see, e.g., Bulinski (1997) *J. Cell Sci.* 110:3055–3064; Panda (1997) *Proc. Natl. A cad. Sci.* USA 94:10560–10564; Muhlradt (1997) *Cancer Res.* 57:3344–3346; Nicolaou (1997) *Nature* 387:268–272; Vasquez (1997) *Mol. Biol. Cell.* 8:973–985; Panda (1996) *J. Biol. Chem.* 271:29807–29812.

Particularly preferred agents are compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) *Cancer Chemother. Pharmacol.* 41:37–47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

In a preferred embodiment, compounds with possible tubulin polymerization activity are screened in vitro. In a preferred embodiment, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) *Lab. Anim. Sci.*, 45(2):145–150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) *J. Molec. Biol.*, 89: 737–758. U.S. Pat. No. 5,569,720 also provides in vitro and in vivo assays for compounds with paclitaxel-like activity.

B) Polyprenyl-protein Transferase Inhibitors

In still another embodiment, this invention provides for the combined use of tumor suppressor nucleic acids and/or polypeptides and polyprenyl-protein transferase inhibitors. Particularly preferred polyprenyl-protein transferase inhibitors include, but are not limited to farnesyl-protein transferase (FPT) inhibitors, geranylgeranyl-protein transferase inhibitors, and other monoterpene protein transferases. Examples of compounds that are polyprenyl-protein transferase inhibitors are well known in the scientific and patent literature, see, e.g., Zhang (1997) *J. Biol. Chem.* 272: 10232–10239; Njoroge (1997) *J. Med. Chem.* 40:4290–4301; Mallams (1997) *Bioorg. Med. Chem.* 5:93–99.

Exemplary compounds that are farnesyl-protein transferase inhibitors are given below:

The FPT inhibitor, designated "FPT39," as described in International Application WO 97/23478, filed Dec. 19, 1996, where FPT39 is designated compound "39.0," see pg 95 of WO 97/23478.

Compound FPT39:

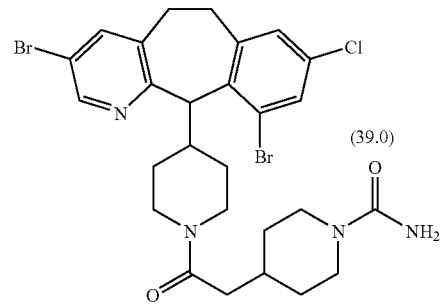

(39.0)

As described infra, when FPT39 is used in combination therapy with a p53 expressing adenovirus of the invention against prostate tumor cells and mammary tumor cells, the combination was more effective at killing tumor cells than either agent alone.

Oligopeptides (mostly tetrapeptides, but also pentapeptides including the formula Cys-Xaa1-Xaa2-Xaa3: EPA 461, 489; EPA 520,823; EPA 528,486; and WO 95/11917).

Peptido-mimetic compounds, especially Cys-Xaa-Xaa-Xaa mimetics: EPA 535,730, EPA 535,731; EPA 618,221; WO 94/09766; WO 94/10138; WO 94/07966; U.S. Pat. Nos. 5,326,773, US 5,340,828, US 5,420,245; WO 95/20396; U.S. Pat. Nos. 5,439,918; and WO 95/20396.

Farnesylated peptide mimetic compounds—specifically farnesylated Cys-Xaa-Xaa-Xaa mimetic: GB-A2.276,618.

Other peptido-mimetic compounds: U.S. Pat. No. 5,352, 705, WO 94/00419; WO 95/00497; WO 95/09000; WO 95/09001; WO 91/12612; WO 95/25086; EPA 675,112, and FR-A 2,718,149.

Fused-ring tricyclic benzocycloheptapyridines: WO 95/10514; WO 95/10515; WO 95/10516; WO 96/30363; WO 96/30018; WO 96/30017; WO 96/30362; WO 96/31111; WO 96/31478; WO 96/31477; WO 9631505; International Patent Application No. PCT/US96/19603, WO 97/23478; U.S. application Ser. No. 08/728104, U.S. application Ser. No. 08/712,989, U.S. application Ser. No. 08/713,326, U.S. application Ser. No. 08/713,908, U.S. application Ser. No. 08/713,705, U.S. application Ser. No. 08/713,703; U.S. application Ser. No. 08/710,225, U.S. application Ser. No. 08/711,925, U.S. application Ser. No. 08/712,924; U.S. application Ser. No. 08/713,323; and U.S. application Ser. No. 08/713,297.

Farnesyl derivatives: EPA 534,546; WO 94/19357; WO 95/08546, EPA 537,007; and WO 95/13059.

Natural products and derivatives: WO 94/18157; U.S. Pat. No. 5,430,055; GB-A 2,261,373, GB-A 2,261,374, GB-A 2,261,375; U.S. Pat. Nos. 5,420,334, U.S. 5,436,263.

Other compounds: WO 94/26723; WO 95/08542; U.S. Pat. No. 5,420,157; WO 95/21815; and WO 96/31501.

C) Anti-Angiogenic Compounds

The tumor suppressor proteins or nucleic acids of this invention can also be administered in conjunction with antiangiogenic compounds. Preferred antiangiogenic compositions inhibit the formation or proliferation of blood vessels, more preferably the formation and/or proliferation of blood vessels to tumors.

Suitable antiangiogenic compositions include, but are not limited to Galardin (GM6001, Glycomed, Inc., Alameda, Calif.), endothelial response inhibitors (e.g., agents such as interferon alpha, TNP-470, and vascular endothelial growth factor inhibitors), agents that prompt the breakdown of the cellular matrix (e.g., Vitaxin (human LM-609 antibody, Ixsys Co., San Diego, Calif.; Metastat, CollaGenex, Newtown, Pa.; and Marimastat BB2516, British Biotech), and agents that act directly on vessel growth (e.g., CM-101, which is derived from exotoxin of Group A Streptococcus antigen and binds to new blood vessels inducing an intense host inflammatory response; and Thalidomide).

Several kinds of steroids have also been noted to exert antiangiogenic activity. In particular, several reports have indicated that medroxyprogesterone acetate (MPA), a synthetic progesterone, potently inhibited neovascularization in the rabbit corneal assay (Oikawa (1988) *Cancer Lett.* 43: 85). A pro-drug of 5FU, 5'-deoxy-5-fluorouridine (5'DFUR), might be also characterized as an antiangiogenic compound, because 5'DFUR is converted to 5-FU by the thymidine phosphorylase activity of PD-ECGF/TP. 5'DFUR might be selectively active for PD-ECGF/TP positive tumor cells with high angiogenesis potential. Recent clinical investigations in showed that 5'DFUR is likely to be effective for PD-ECGF/TP-positive tumors. It was showed that a dramatic enhancement of antitumor effect of 5'DFUR appeared in PD-ECGF/TP transfected cells compared with untransfected wild-type cells (Haraguchi (1993) *Cancer Res.* 53: 5680–5682). In addition, combined 5'DFUR+MPA compounds are also effective antiangiogenics (Yayoi (1994) *Int J Oncol.* 5: 27–32). The combination of the 5'DFUR+MPA might be categorized as a combination of two angiogenesis inhibitors with different spectrums, an endothelial growth factor inhibitor and a protease inhibitor. Furthermore, in in-vivo experiments using DMBA-induced rat mammary carcinomas, 5'DFUR exhibited a combination effect with AGM-1470 (Yamamoto (1995) *Oncol Reports* 2:793–796).

Another group of antiangiogenic compounds for use in this invention include polysaccharides capable of interfering with the function of heparin-binding growth factors that promote angiogenesis (e.g., pentosan polysulfate).

Other modulators of angiogenesis include platelet factor IV, and AGM 1470. Still others are derived from natural sources collagenase inhibitor, vitamin D3-analogues, fumigallin, herbimycin A, and isoflavones.

D) Endocrine Therapy

Endocrine therapy, which is already established and a representative cytostatic treatment, can lead hormone-dependent cells to be quiescent and can reduce tumor cell number in-vivo and can inhibit tumor growth in patients with hormone-dependent tumors. Such therapies are expected to augment the effect of tumor suppressors in the treatment of hyperproliferative cells. Thus, in another embodiment, this invention provides, e.g., for the combined use of a tumor suppressor nucleic acid and/or polypeptide and an anti-estrogen, anti-androgen, or anti-progesterone. Endocrine therapeutics are well known to those of skill in the art are include, but are not limited to tamoxifen, toremifene (see, e.g., U.S. Pat. No. 4,696,949), flutamide, megace, and lupron, see, also, e.g., WO 91/00732, WO 93/10741, WO 96/26201, and Gauthier et al. *J. Med. Chem.* 40: 2117–2122 (1997).

E) Delivery of Adjunctive Anti-Cancer Agents: Pharmaceutical Compositions

Pharmaceutical Compositions

The adjunctive anti-cancer agents used in the methods of the invention are typically combined with a pharmaceutically acceptable carrier (excipient) to form a pharmacological composition. The pharmaceutical composition of the invention can comprise one or more adjunctive anti-cancer agents with or without a tumor suppressor gene or polypeptide, e.g., p53 or RB.

Pharmaceutically acceptable carriers can contain a physiologically acceptable compound that acts, e.g., to stabilize the composition or to increase or decrease the absorption of the agent and/or pharmaceutical composition. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the adjunctive anti-cancer agents, or excipients or other stabilizers and/or buffers. Detergents can also used to stabilize the composition or to increase or decrease the absorption of the pharmaceutical composition (see infra for exemplary detergents).

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a pharmaceutically acceptable carrier, including a physiologically acceptable compound depends, for example, on the route of administration of the adjunctive anti-cancer agent and on the particular physio-chemical characteristics of the adjunctive anti-cancer agent.

The compositions for administration will commonly comprise a solution of the adjunctive anti-cancer agent dissolved in a pharmaceutically acceptable carrier, preferably an aqueous carrier for water-soluble adjunctive anti-cancer agents. A variety of carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of adjunctive anti-cancer agent in these formulations can vary widely, and will be selected primarily based on fluid volumes, viscosities, body weight and the like in accordance with the particular mode of administration selected and the patient's needs.

Routes of Delivery

The adjunctive anti-cancer agents used in the methods of the invention are useful for and can be delivered alone or as pharmaceutical compositions (with or without a tumor suppressor, e.g., p53) by any means known in the art, e.g., systemically, regionally, or locally; by intraarterial, intratumoral, intravenous (IV), parenteral, intra-pleural cavity, topical, oral, or local administration, as subcutaneous, intratracheal (e.g., by aerosol) or transmucosal (e.g., buccal, bladder, vaginal, uterine, rectal, nasal mucosa), intra-tumoral (e.g., transdermal application or local injection). Particularly preferred modes of administration include intra-arterial injections, especially when it is desired to have a "regional effect," e.g., to focus on a specific organ (e.g., brain, liver, spleen, lungs). For example, intra-hepatic artery injection is preferred if the anti-tumor regional effect is desired in the liver; or, intra-carotid artery injection, where it is desired to deliver a composition to the brain, (e.g., for treatment of brain tumors) a carotid artery or an artery of the carotid system of arteries (e.g., occipital artery, auricular artery, temporal artery, cerebral artery, maxillary artery, etc.).

Paclitaxel and certain paclitaxel derivatives are only marginally soluble in aqueous solutions. In a preferred embodiment, these compositions are either delivered directly to the tumor locale (e.g. by injection, canalization, or direct application during a surgical procedure) or they are solubilized in an acceptable excipient. Methods of administering paclitaxel and its derivatives are well known to those of skill in the art (see, e.g., U.S. Pat. Nos. 5,583,153, 5,565,478, 5,496,804, 45,484,809. Other paclitaxel derivatives are water soluble analogues and/or prodrugs (see, U.S. Pat. Nos. 5,411,984 and 5,422,364) and are conveniently administered by any of a variety of methods as described above.

The pharmaceutical compositions of this invention are particularly useful for topical administration e.g., in surgical wounds to treat incipient tumors, neoplastic and metastatic cells and their precursors In another embodiment, the compositions are useful for parenteral administration, such as intravenous administration or administration into a body cavity or lumen of an organ.

Treatment Regimens

The pharmaceutical compositions can be administered in a variety of unit dosage forms depending upon the method of administration. For example, unit dosage forms suitable for oral administration include powder, tablets, pills, capsules and lozenges. It is recognized that the adjunctive anti-cancer compounds (e.g., paclitaxel and related compounds described of, when administered orally, must be protected from digestion. This is typically accomplished either by complexing the adjunctive anti-cancer agent with a composition to render it resistant to acidic and enzymatic hydrolysis or by packaging the adjunctive anti-cancer agent in an appropriately resistant carrier such as a liposome. Means of protecting compounds from digestion are well known in the art (see, e.g., U.S. Pat. No. 5,391,377 describing lipid compositions for oral delivery of therapeutic agents).

Dosages for typical chemotherapeutics are well known to those of skill in the art. Moreover, such dosages are typically advisorial in nature and may be adjusted depending on the particular therapeutic context, patient tolerance, etc. Thus, for example, a typical pharmaceutical composition (I, paclitaxel) dosage for intravenous (IV) administration would be about 135 mg/m$^2$ administered over 1–24 hours (typically at 1, 3, or 6 hours, more preferably 3 hours) and more preferably repeated every three weeks for 3 to 6 cycles. To decrease the frequency and severity of hypersensitivity reactions, patients may also receive about 20 mg of dexamethasone (Decadron, and others) orally about 12 hours and 6 hours before, and about 50 mg of diphenhydramine (BENADRYL®, and others) plus about 300 mg of cimetidine (TAGAMET®) or 50 mg of rantidine (ZANTAC®) IV 30 to 60 minutes before treatment with paclitaxel. Considerably higher dosages (e.g., ranging up to up to about 350 mg/m$^2$ per day may be used, particularly when the drug is administered to a secluded site and not into the blood stream, such as into a body cavity or into a lumen of an organ. Substantially higher dosages are possible by any selected route, for example, topical administration. Actual methods for preparing parenterally administrable compositions will be known or apparent to those skilled in the art and are described in more detail in such publications as Remington's Pharmaceutical Science, 15th ed., Mack Publishing Company, Easton, Penn. (1980) and U.S. Pat. Nos. 5,583,153, 5,565,478, 5,496,804, and 5,484,809. Typical doses, e.g., for intraperitoneal administration, will be 20–150 mg/m$^2$ weekly, or about 250 mg/m$^2$ every 3 weeks.

The compositions containing the adjunctive anti-cancer agents can be administered for therapeutic treatments. In therapeutic applications, compositions are administered to a patient suffering from a disease characterized by hyperproliferation of one or more cell types in an amount sufficient to cure or at least partially arrest the disease and/or its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the adjunctive anti-cancer agents of this invention to effectively treat the patient.

II. Tumor Suppressor Genes and Gene Products

A) Preferred Known Tumor Suppressors

As explained above, in one embodiment, this invention provides methods of inhibiting the growth and/or proliferation of cells by contacting the cells with a tumor suppressor nucleic acid and an adjunctive anti-cancer agent (e.g., paclitaxel, a paclitaxel derivative or a paclitaxel-like compound).

Tumor suppressor genes are well known to those of skill in the art and include, but are not limited to RB, p53, APC, FHIT (see, e.g., Siprashvili (1997) *Proc. Natl. Acad. Sci. USA* 94:13771–13776), BRACA1 and BRCA2, VHL, WT, DCC, FAP, NF, MEN, E-cadherin, nm23, MMACI, and PTC. The RB or retinoblastoma gene is the prototypical tumor suppressor and has been well characterized (see, e.g., Bookstein (1990) *Science* 247: 712–715, Benedict (1980) *Cancer Invest.*, 8: 535–540, Riley (1990) *Ann. Rev. Cell Biol.* 10-1-29, and Wienberg (1992) *Science* 254: 1138–1146. Perhaps the best characterized tumor suppressor is p53 which has been implicated in many neoblastomas as well as in the genetic predisposition to the development of diverse tumors in families with Li-Fraumeni syndrome (see, e.g., Wills (1994) *Hum. Gene Therap.* 5:1079–1088, U.S. Pat. No. 5,532,220, WO 95/289048, and Harris (1996) *J. Nat. Canc. Inst.* 88(20): 1442) which describe the cloning expression and use of p53 in gene therapy). Other tumor suppressors include WT (i.e., WT1 at 11p13) gene characteristic of Wilms' tumor (see Call et al. (1990) Cell, 60: 60: 509–520, Gessler (1990) Nature 343: 774–778, and Rose et al. (1990) Cell, 60: 495–508). The tumor suppressor gene called FHIT, for Fragile Histidine Triad, was found in a region on chromosome 3 (3p14.2, also reported at 3p21) that is known to be particularly prone to translocations, breaks, and gaps is believed to lead to esophageal, stomach and colon cancers (see, e.g., Ohta et al. (1996) Cell, 84: 587–597, GenBank Accession No: U469227). The tumor suppressor genes DCC (18q21) and FAP are associated with colon carcinoma (see, e.g., Hedrick et al. (1994) Genes Dev., 8(10): 1174–1183, GenBank Accession No: X76132 for DCC, and Wienberg (1992) Science, 254: 1138–1146 for FAP). The NF tumor suppressors (NF1 at 17q11 and NF2 at 22q12) are associated with neurological tumors (e.g., neurofribromatosis for NF1 see, e.g., Caivthon et al. (1990) Cell, 62: 193–201, Viskochil et al. (1990) Cell, 62: 187–192, Wallace et al. (1990) Science, 249: 181–186, and Xug et al. (1990) Cell, 62: 599–608; and Meningioma and schwannoma for NF2). The MEN tumor suppressor is associated with tumors of the multiple endocrine neoplasia syndrome (see, e.g., Wienberg Science, 254: 1138–1146, and Marshall (1991) Cell, 64: 313–326). The VHL tumor suppressor is associated with von Hippel-Landau disease (Latif (1993) Science 260: 1317–1320, GenBank Accession No: L15409). The widely publicized BRCA1 and BRCA2 genes are associated with breast cancer (see, e.g., Skolnick (1994) Science, 266: 66–71, GenBank Accession No: U14680 for BRCA1, and Teng (1996) Nature Genet. 13:241–244, GenBank Accession No: U43746)). In addition, the E-cadherin gene is associated with the invasive phenotype of prostate cancer (Umbas (1992) Cancer Res. 52: 5104–5109, Bussemakers (1992) Cancer Res. 52: 2916–2999, GenBank Accession No: 272397). The NM23 gene is associated with tumor metastasis (Dooley (1994) Hum. Genet., 93(1): 63–66, GenBank Accession No: X75598). Other tumor suppressors include DPC4 (identified at 18q21) associated with pancreatic cancer, hMLH1 (3p) and hMSH2 (2p) associated with colon cancers, and CDKN2 (p16) and (9p) associated with melanoma, pancreatic and esophageal cancers. Finally, the human PTC gene (a homologue of the drosophila patched (ptc) gene) is associated with nevoid basal cell carcinoma syndrome (NBCCS) and with somatic basal cell carcinomas (see, e.g., see Hahn et al. (1996) Cell, 85: 841–851). This list of tumor suppressor genes is neither exhaustive nor intended to be limiting and is meant simply to illustrate the wide variety of known tumor suppressors.

B) Identification and Screening of Previously Unknown Tumor Suppressors

Methods of identifying or assaying for tumor suppressor genes are well known to those of skill in the art. Typically hyperproliferative cells are screened for gene loss of which, or mutation of which, is associated (correlated) with the hyperproliferative state. The most stringent test for a gene to qualify as a tumor suppressor gene (TSG) is its ability to suppress the tumorigenic phenotype of a tumor or of cells derived from a tumor. The tumor suppressor nucleic acid is preferably introduced into tumor cells as a cloned cDNA in an appropriate expression vector, or an individual chromosome harboring a candidate tumor suppressor gene is introduced into tumor cells by microcell transfer technique. Alternatively, the tumor suppressor gene product (e.g., a tumor suppressor polypeptide) is introduced into the cell(s) and the proliferation rate of the cells is measured (e.g., by counting cells or measuring tumor volume, etc.). Complete or partial inhibition of proliferation (e.g., decrease of proliferation rate), contact inhibition, loss of invasive phenotype, cell differentiation, and apoptosis, are all indicators of suppression of the tumorigenic phenotype (reduced susceptibility to the neoplastic state).

Methods of screening tumors to identify altered or underexpressed nucleic acids are well known to those of skill in the art. Such methods include, but are not limited to subtractive hybridization (see, e.g., Hampson (1992) Nucleic Acids Res. 20:2899), comparative genomic hybridization ((CGH), see, e.g., WO 93/18186, Kallioniemi (1992) Science, 258: 818), and expression monitoring using high density arrays of nucleic acid probes (see, e.g., Lockhart (1996) Nature Biotechnology, 14(13): 1675–1680).

C) Preparation of p53 and Other Tumor Suppressors

As indicated above, this invention involves contacting a cell, e.g., in vitro, in physiological solution (e.g., blood), in a tissue organ, or organism with a tumor suppressor nucleic acid or a tumor suppressor gene product such as a polypeptide. The tumor suppressor nucleic acid or polypeptide can be a nucleic acid or polypeptide of any known tumor suppressor including, but not limited to RB, p53, h-NUC (Chen (1995) supra), APC, FHIT, BRACA1, BRCA2, VHL, WT, DCC, FAP, NF, MEN, E-cadherin, nm23, MMACI, and PTC as described above. In a preferred embodiment, the tumor suppressor is an RB nucleic acid or polypeptide or a p53 nucleic acid or polypeptide or active fragment(s) thereof.

In a most preferred embodiment, the p53 or RB tumor suppressor nucleic acid is present in an expression cassette under control of a promoter that expresses the tumor suppressor gene or cDNA when it is located in the target (e.g., tumor) cell. Methods of constructing expression cassettes and/or vectors encoding tumor suppressor genes are well known to those of skill in the art as described below.

1. Preparation of Tumor Suppressor Nucleic Acids.

DNA encoding the tumor suppressor proteins or protein subsequences of this invention may be prepared by any suitable method including, for example, cloning and restriction of appropriate sequences or direct chemical synthesis (e.g., using existing sequence information as indicated above) by methods such as the phosphotriester method of Narang (1979) Meth. Enzymol. 68: 90–99; the phosphodiester method of Brown et al., Meth. Enzymol. 68: 109–151 (1979); the diethylphosphoramidite method of Beaucage et al., Tetra. Lett., 22: 1859–1862 (1981); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In one embodiment, tumor suppressor nucleic acids of this invention may be cloned using DNA amplification methods such as polymerase chain reaction (PCR). Thus, for example, the nucleic acid sequence or subsequence is PCR amplified, using a sense primer containing one restriction site (e.g., NdeI) and an antisense primer containing another restriction site (e.g., HindIII). This will produce a nucleic acid encoding the desired tumor suppressor sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the published sequence information for any particular known tumor suppressor gene, cDNA, or protein. Appropriate restriction sites can also be added to the nucleic acid encoding the tumor suppressor protein or protein subsequence by site-directed mutagenesis. The plasmid containing the tumor suppressor sequence or subsequence is cleaved with the appropriate restriction endonuclease and then ligated into the vector encoding the second molecule according to standard methods.

As indicated above, the nucleic acid sequences of many tumor suppressor genes are known. Thus, for example, the nucleic acid sequence of p53 is found in Lamb et al. (1986) *Mol. Cell Biol.* 6: 1379–1385, GenBank Accession No: M13111). Similarly, the nucleic acid sequence of RB is described by Lee et al. (1987) *Nature,* 329: 642–645 (GenBank Accession No: M28419). The nucleic acid sequences of other tumor suppressors are available as indicated above in Section II(a). Using the available sequence information one of ordinary skill in the art can clone the tumor suppressor genes into vectors suitable for practice in this invention.

The p53 and RB tumor suppressors are particularly preferred for use in the methods of this invention. Methods of cloning p53 and RB into vectors suitable for expression of the respective tumor suppressor proteins or for gene therapy applications are well known to those of skill in the art. Thus, for example, the cloning and use of p53 is described in detail by Wills (1994) supra; in U.S. Pat. No. 5,532,220, in copending U.S. Ser. No. 08/328,673 filed on Oct. 25, 1994, and in WO 95/11984. Typically the expression cassette is constructed with the tumor suppressor cDNA operably linked to a promoter, more preferably to a strong promoter (e.g., the Ad2 major late promoter (Ad2 MLP), or the human cytomegalovirus immediate early gene promoter (CMV)). In a particularly preferred embodiment, the promoter is followed by the tripartite leader cDNA and the tumor suppressor cDNA is followed by a polyadenylation site (e.g., the E1b polyadenylation site) (see, e.g., copending U.S. Ser. No. 08/328,673, WO 95/11984 and Wills (1994) supra). It will be appreciated that various tissue-specific promoters are also suitable. Thus, for example, a tyrosinase promoter can be used to target expression to melanomas (see, e.g., Siders (1996) *Cancer Res.* 56:5638–5646). In a particularly preferred embodiment, the tumor suppressor cDNA is expressed in a vector suitable for gene therapy as described below.

2. Preparation of Tumor Suppressor Protein.

a) De novo Chemical Synthesis

Using known sequences of tumor suppressor polypeptides, the tumor suppressor proteins or subsequences thereof may be synthesized using standard chemical peptide synthesis techniques. Where the desired subsequences are relatively short (e.g., when a particular antigenic determinant is desired) the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis;* pp. 3–284 in *The Peptides: Analysis, Synthesis, Biology. Vol.* 2: *Special Methods in Peptide Synthesis, Part a.,* Merrifield, et al. *J. Am. Chem. Soc.,* 85: 2149–2156 (1963), and Stewart et al., *Solid Phase Peptide Synthesis, 2nd* ed. Pierce Chem. Co., Rockford, Ill. (1984).

b) Recombinant Expression

In a preferred embodiment, the tumor suppressor proteins or subsequences thereof, are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

Methods of cloning the tumor suppressor nucleic acids into a particular vector are described above. The nucleic acid sequences encoding tumor suppressor proteins or protein subsequences may then be expressed in a variety of host cells, including *E. coli,* other bacterial hosts, yeast, and various higher eukaryotic cells such as the COS, CHO and HeLa cells lines and myeloma cell lines. As the tumor suppressor proteins are typically found in eukaryotes, a eukaryote host is preferred. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant tumor suppressor proteins can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology Vol.* 182: *Guide to Protein Purification.,* Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

One of skill in the art would recognize that after chemical synthesis, biological expression, or purification, the tumor suppressor protein(s) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski (1993) *J. Biol. Chem.* 268: 14065–14070; Kreitman (1993) *Bioconjug. Chem.* 4: 581–585; and Buchner (1992) *Anal. Biochem.* 205: 263–270). Debinski (1993) supra, for example, describes the denaturation and reduction of inclusion body proteins in guanidine-DTE. The protein is then refolded in a redox buffer containing oxidized glutathione and L-arginine.

One of skill will appreciate that many conservative variations of the nucleic acid and polypeptide sequences described herein yield functionally identical products. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties (see, the definitions section, supra), are also readily identified as being highly similar to a disclosed amino acid sequence, or to a disclosed nucleic acid sequence which encodes an amino acid. Such conservatively substituted variations of each explicitly described sequence are a feature of the present invention.

One of skill would recognize that modifications can be made to the tumor suppressor proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Modifications to nucleic acids and polypeptides may be evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques.

D) Delivery of Tumor Suppressors to Target Cells.

The tumor suppressors used in the methods of this invention can be introduced to the cells either as a protein or as a nucleic acid. Where the tumor suppressor is provided as a protein, a tumor suppressor gene expression product (e.g., a p53 or an RB polypeptide or fragment thereof possessing tumor suppressor activity) is delivered to the target cell using standard methods for protein delivery (see discussion, below). Alternatively, where the tumor suppressor is a tumor suppressor nucleic acid (e.g., a gene, a cDNA, an mRNA, etc.) the nucleic acid is introduced into the cell using conventional methods of delivering nucleic acids to cells. These methods typically involve delivery methods of in vivo or ex vivo gene therapy as described below. Particularly preferred methods of delivering p53 or RB include lipid or liposome delivery and/or the use of retroviral or adenoviral vectors.

1. In vivo Gene Therapy

In a more preferred embodiment, the tumor suppressor nucleic acids (e.g., cDNA(s) encoding the tumor suppressor protein) are cloned into gene therapy vectors that are competent to transfect cells (such as human or other mammalian cells) in vitro and/or in vivo.

Several approaches for introducing nucleic acids into cells in vivo, ex vivo and in vitro have been used. These include lipid or liposome based gene delivery (WO 96/18372; WO 93/24640; Mannino (1988) *BioTechniques* 6(7): 682–691; Rose, U.S. Pat. No. 5,279,833; WO 91/06309; and Felgner (1987) *Proc. Natl. Acad. Sci. USA* 84: 7413–7414) and replication-defective retroviral vectors harboring a therapeutic polynucleotide sequence as part of the retroviral genome (see, e.g., Miller (1990) *Mol. Cell. Biol.* 10:4239 (1990); Kolberg (1992) *J. NIH Res.* 4: 43, and Cornetta (1991) *Hum. Gene Ther.* 2: 215).

For a review of gene therapy procedures, see, e.g., Zhang (1996) *Cancer Metastasis Rev.* 15:385–401; Anderson, *Science* (1992) 256: 808–813; Nabel (1993) *TIBTECH* 11: 211–217; Mitani (1993) *TIBTECH* 11: 162–166; Mulligan (1993) *Science*, 926–932; Dillon (1993) *TIBTECH* 11: 167–175; Miller (1992) *Nature* 357: 455–460; Van Brunt (1988) *Biotechnology* 6(10): 1149–1154; Vigne (1995) Restorative Neurology and Neuroscience 8: 35–36; Kremer (1995) *British Medical Bulletin* 51(1) 31–44; Haddada (1995) in *Current Topics in Microbiology and Immunology*, Doerfler and Böhm (eds) Springer-Verlag, Heidelberg Germany; and Yu (1994) *Gene Therapy*, 1:13–26.

The vectors useful in the practice of the present invention are typically derived from viral genomes. Vectors which may be employed include recombinantly modified enveloped or non-enveloped DNA and RNA viruses, preferably selected from baculoviridiue, parvoviridiae, picornoviridiae, herpesveridiae, poxviridae, adenoviridiae, or picornnaviridiae. Chimeric vectors may also be employed which exploit advantageous ments of each of the parent vector properties (See e.g., Feng (1997) Nature Biotechnology 15:866–870. Such viral genomes may be modified by recombinant DNA techniques to include the tumor suppressor gene and may be engineered to be replication deficient, conditionally replicating or replication competent. In the preferred practice of the invention, the vectors are replication deficient or conditionally replicating. Preferred vectors are derived from the-adenoviral, adeno-associated viral and retroviral genomes. In the most preferred practice of the invention, the vectors are replication incompetent vectors derived from the human adenovirus genome.

Conditionally replicating viral vectors are used to achieve selective expression in particular cell types while avoiding untoward broad spectrum infection. Examples of conditionally replicating vectors are described in Bischoff, et al. (1996) Science 274:373–376; Pennisi, E. (1996) Science 274:342–343; Russell, S. J. (1994) Eur. J. of Cancer 30A (8):1165–1171. Additionally, the viral genome may be modified to include inducible promoters which achieve replication or expression of the transgene only under certain conditions. Examples of inducible promoters are known in the scientific literature (See, e.g. Yoshida and Hamada (1997) Biochem. Biophys. Res. Comm. 230:426–430; Iida, et al. (1996) J. Virol. 70(9):6054–6059; Hwang, et al.(1997) J. Virol 71(9):7128–7131; Lee, et al. (1997) Mol. Cell. Biol. 17(9):5097–5105; and Dreher, et al.(1997) J. Biol. Chem 272(46); 29364–29371. The transgene may also be under control of a tissue specific promoter region allowing expression of the transgene only in particular cell types.

Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher (1992) *J. Virol.* 66(5) 2731–2739; Johann (1992) *J. Virol.* 66 (5):1635–1640 (1992); Sommerfelt (1990) *Virol.* 176:58–59; Wilson (1989) *J. Virol.* 63:2374–2378; Miller (1991) J. Virol. 65:2220–2224; Wong-Staal et al., PCT/US94/05700, and Rosenburg and Fauci (1993) in *Fundamental Immunology*, Third Edition Paul (ed) Raven Press, Ltd., New York and the references therein, and Yu (1994) supra). The vectors are optionally pseudotyped to extend the host range of the vector to cells which are not infected by the retrovirus corresponding to the vector. The vesicular stomatitis virus envelope glycoprotein (VSV-G) has been used to construct VSV-G-pseudotyped HIV vectors which can infect hematopoietic stem cells (Naldini et al. (1996) *Science* 272:263, and Akkina (1996) *J Virol* 70:2581).

Adeno-associated virus (AAV)-based vectors are also used to transduce cells with target nucleic acids, e.g., in the in vitro production of nucleic acids and peptides, and in in vivo and ex vivo gene therapy procedures. See, Okada (1996) *Gene Ther.* 3:957–964; West (1987) *Virology* 160: 38–47; Carter (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351, for an overview of AAV vectors. Construction of recombinant AAV vectors are described in a number of publications, including Lebkowski, U.S. Pat. No. 5,173,414; Tratschin (1985) *Mol. Cell. Biol.* 5(11):3251–3260; Tratschin (1984) *Mol. Cell. Biol.* 4: 2072–2081; Hermonat (1984) *Proc. Natl. Acad. Sci. USA* 81: 6466–6470; McLaughlin (1988) and Samulski (1989) *J. Virol.*, 63:03822–3828. Cell lines that can be transformed by rAAV include those described in Lebkowski (1988) *Mol. Cell. Biol.*, 8:3988–3996. Other suitable viral vectors include herpes virus and vaccinia virus.

In a particularly preferred embodiment, the tumor suppressor gene is expressed in an adenoviral vector suitable for gene therapy. The use of adenoviral vectors in vivo, and for gene therapy, is well described in the patent and scientific literature, e.g., see, Hermens (1997) *J. Neurosci. Methods.*, January, 71(1): 85–98; Zeiger (1996) *Surgery* 120:921–925; Channon (1996) *Cardiovasc Res.* 32:962–972; Huang (1996) *Gene Ther.* 3:980–987; Zepeda (1996) *Gene Ther.* 3:973–979; Yang (1996) *Hum. Mol. Genet.* 5:1703–1712; Caruso (1996) *Proc. Natl. Acad. Sci. USA* 93:11302–11306; Rothmann (1996) *Gene Ther.* 3:919–926; Haecker (1996) *Hum. Gene Ther.* 7:1907–1914. The use of adenoviral vectors is described in detail in WO 96/25507. Particularly preferred adenoviral vectors are described by Wills (1994) supra; in copending U.S. Ser. No. 08/328,673, and WO 95/11984.

Particularly preferred adenoviral vectors include a deletion of some or all of the protein IX gene. In one embodiment, the adenoviral vectors include deletions of the E1a and/or E1b sequences. In a most preferred embodiment, the adenoviral construct is a p53 encoding construct such as A/C/N/53 or A/M/N/53 (see, e.g., U.S. Ser. No. 08/328,673, and WO 95/11984).

Also preferred are vectors derived from the human adenovirus type 2 or type 5. Such vectors are preferably are replication deficient by modifications or deletions in the E1a and/or E1b coding regions. Other modifications to the viral genome to achieve particular expression characteristics or permit repeat administration or lower immune response are preferred. More preferred are recombinant adenoviral vectors having complete or partial deletions of the E4 coding region, optionally retaining E4 ORF6 and ORF 6/7. The E3 coding sequence may be deleted but is preferably retained. In particular, it is preferred that the promoter operator region of E3 be modified to increase expression of E3 to achieve a more favorable immunological profile for the therapeutic vectors. Most preferred are human adenoviral type 5 vectors containing a DNA sequence encoding p53 under control of the cytomegalovirus promoter region and the tripartite leader sequence having E3 under control of the CMV promoter and deletion of E4 coding regions while retaining E4 ORF6 and ORF 6/7. In the most preferred practice of the invention as exemplified herein, the vector is ACN53.

In a particularly preferred embodiment, the tumor suppressor gene is p53 or RB. As explained above. the cloning and use of p53 is described in detail by Wills (1994) supra; in copending U.S. Ser. No. 08/328,673 filed on Oct. 25, 1994, and in WO 95/11984.

2. Ex vivo Gene Therapy

In one embodiment, the methods of this invention are used to inhibit hyperproliferative (e.g., neoplastic) cells in a subject (e.g., a mammal including but not limited to rat, murine, bovine, porcine, equine, canine, feline, largomorph, or human). Pathologic hyperproliferative cells are characteristic off disease states including, but not limited to Grave's disease, psoriasis, benign prostatic hypertrophy, Li-Fraumeni syndrome, breast cancer, sarcomas, bladder cancer, colon cancer, lung cancer various leukemia and lymphomas and other neoplasms.

Ex vivo application of the methods of this invention, in particular, provide means for depleting a suitable sample of pathologic hyperproliferative cells. Thus, for example hyperproliferative cells contaminating hematopoietic precursors during bone marrow reconstitution can be eliminated by the ex vivo application of the methods of this invention. Typically such methods involve obtaining a sample from the subject organism. The sample is typically a heterogenous cell preparation containing both phenotypically normal and pathogenic (hyperproliferative) cells. The sample is contacted with the tumor suppressor nucleic acids or proteins and the adjunctive anti-cancer agent according to the methods of this invention. The tumor suppressor gene can be delivered, e.g., in a viral vector, such as a retroviral vector or an adenoviral vector. The treatment reduces the proliferation of the pathogenic cells thereby providing a sample containing a higher ratio of normal to pathogenic cells which can be reintroduced into the subject organism.

Ex vivo cell transformation for diagnostics, research, or for gene therapy (e.g., via re-infusion of the transformed cells into the host organism) is well known to those of skill in the art. In a preferred embodiment, cells are isolated from the subject organism, transfected with the tumor suppressor gene or cDNA of this invention, and re-infused back into the subject organism (e.g., patient). Various cell types suitable for ex vivo transformation are well known to those of skill in the art. Particular preferred cells are progenitor or stem cells (see, e.g., Freshney (1994) *Culture of Animal Cells, a Manual of Basic Technique, third edition* Wiley-Liss, New York, and the references cited therein for a discussion of how to isolate and culture cells from patients). Transformed cells are cultured by means well known in the art. See, also Kuchler (1977) *Biochemical Methods in Cell Culture and Virology*, Kuchler, R. J., Dowden, Hutchinson and Ross, Inc., and Atlas (1993) *CRC Handbook of Microbiological Media* (Parks ed) CRC press, Boca Raton, Fla. Mammalian cell systems often will be in the form of monolayers of cells, although mammalian cell suspensions are also used. Alternatively, cells can be derived from those stored in a cell bank (e.g., a blood bank). Illustrative examples of mammalian cell lines include the HEC-1-B cell line, VERO and Hela cells, Chinese hamster ovary (CHO) cell lines, W138, BHK, Cos-7 or MDCK cell lines (see, e.g., Freshney, supra).

In one particularly preferred embodiment, stem cells are used in ex-vivo procedures for cell transformation and gene therapy. The advantage to using stem cells is that they can be differentiated into other cell types in vitro, or can be introduced into a mammal (such as the donor of the cells) where they will engraft in the bone marrow. Methods for differentiating stem cells (e.g., CD34+) stem cells in vitro into clinically important immune cell types using cytokines such a GM-CSF, IFN-gamma and TNF-alpha are known (see, e.g., Inaba (1992) *J. Exp. Med.* 176:1693–1702; Szabolcs (1995) 154:5851–5861).

Rather than using stem cells, T cells or B cells are also used in some embodiments in ex vivo procedures. Several techniques are known for isolating T and B cells. The expression of surface markers facilitates identification and purification of such cells. Methods of identification and isolation of cells include FACS, incubation in flasks with fixed antibodies which bind the particular cell type and panning with magnetic beads.

Stem cells are isolated for transduction and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as CD4+ and CD8+ (T cells), CD45+ (panb cells), GR-1 (granulocytes), and Ia$^d$ (differentiated antigen presenting cells). For an example of this protocol see, e.g., Inaba (1992) supra.

In humans, bone marrow aspirations from iliac crests are performed e.g., under general anesthesia in the operating room. The bone marrow aspirations is approximately 1,000 ml in quantity and is collected from the posterior iliac bones and crests. If the total number of cells collected is less than about 2×10$^8$/kg, a second aspiration using the sternum and anterior iliac crests in addition to posterior crests is performed. During the operation, irradiated packed red cells are administered to replace the volume of marrow taken by the aspiration. Human hematopoietic progenitor and stem cells are characterized by the presence of a CD34 surface membrane antigen. This antigen is used for purification, e.g., on affinity columns which bind CD34. After the bone marrow is harvested, the mononuclear cells are separated from the other components by means of ficol gradient centrifugation. This can be performed by a semi-automated method using a cell separator (e.g., a Baxter Fenwal CS3000+ or Terumo machine). The light density cells, composed mostly of mononuclear cells are collected and the cells are incubated in plastic flasks at about 37° C. for about 1.5 hours. The adherent cells (monocytes, macrophages and B-Cells) are discarded. The non-adherent cells are then collected and incubated with a monoclonal anti-CD34 antibody (e.g., the murine antibody 9C5) at 4° C. for 30 minutes with gentle rotation. The final concentration for the anti-CD34 antibody is preferably about 10 µg/ml. After two washes, paramagnetic microspheres (e.g., Dyna Beads, supplied by Baxter Immunotherapy Group, Santa Ana, Calif.) coated with sheep antimouse IgG (Fc) antibody are added to the cell suspension at a ratio of about 2 cells/bead. After a further incubation period of about 30 minutes at about 4° C., the rosetted cells with magnetic beads are collected with a magnet. Chymopapain (Baxter Immunotherapy Group, Santa Ana, Calif.) at a final concentration of 200 U/ml can be added to release the beads from the CD34+ cells.

Alternatively, and preferably, an affinity column isolation procedure can be used which binds to CD34, or to antibodies bound to CD34 (see, e.g., Ho (1995) *Stem Cells* 13 (suppl. 3): 100–105 and Brenner (1993) *Journal of Hematotherapy* 2: 7–17).

In another embodiment, hematopoietic stem cells can be isolated from fetal cord blood. Yu (1995) *Proc. Natl. Acad. Sci. USA*, 92: 699–703 describe a preferred method of transducing CD34+ cells from human fetal cord blood using retroviral vectors.

3. Administration of Tumor Suppressor-Expressing Nucleic Acid: Vectors and Expression Cassettes Routes of Administration Expression cassettes and vectors (e.g., retroviruses, adenoviruses, liposomes, etc.) containing the therapeutic, tumor suppressor-expressing nucleic acids of the invention, can be administered directly to the organism for transduction of cells in vivo. Administration is by any of the routes normally used for introducing a molecule into ultimate contact with blood or tissue cells, e.g., systemically, regionally, or locally, as discussed in detail, supra, for the administration of adjunctive anti-cancer agents. The "packaged" nucleic acids (at a minimum, a tumor suppressor coding sequence with a promoter) are administered in any suitable manner, preferably with pharmaceutically acceptable carriers, also discussed supra. Suitable methods of administering such packaged nucleic acids are available and well known to those of skill in the art, and, although more than one route can be used to administer a particular composition, a particular route can often provide a more immediate and more effective reaction than another route.

For example, administration of a recombinant adenovirus vector engineered to express a tumor suppressor gene can elicit an immune response, specifically, an antibody response, against the adenoviral vector. Some patients may have pre-existing anti-adenoviral reacting antibodies. Thus, in some circumstances, regional or local, rather than systemic, administration, of the tumor-suppressor expressing adenoviral vector is optimal and most effective. For example, as discussed below, ovarian cancer limited to the abdominal cavity is one clinical scenario in which regional p53 gene therapy, i.e., intraperitoneal (IP) administration, should be considered as a preferred treatment plan. Administration of recombinant adenoviruses IP also results in infection of the peritoneal lining and absorption of the adenoviral vector into the systemic circulation (other means of regional administration can also result in introduction of the adenoviral vector into the systemic circulation). The extent of this effect may depend on the concentration and/or total amount of viral particles administered IP. If the systemic effect is desired, a higher concentration over several consecutive days may be preferred.

Local administration of the tumor suppressor-expressing adenoviral vector of the invention is also preferred in some circumstances, e.g., when the patient has pre-existing anti-adenoviral reactive antibodies. Such "local administration" can be, e.g., by intra-tumoral injection, if internal, or mucosal application, if external. Alternatively, a "local administration" effect can be effected by targeting the adenoviral vector to the tumor using, e.g., tumor specific antigen-recognizing reagents (as antibodies) on liposomes or on the adenovirus itself.

Formulations

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration of pharmaceutical compositions comprising the tumor suppressor-expressing nucleic acids can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d)

suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The packaged nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose sealed containers, such as ampules and vials.

Formulations of the invention as injection solutions and suspensions can be prepared from sterile powders, granules, and tablets of the kind previously described. The exact composition of the formulation, the concentration of the reagents and nucleic acid in the formulation, its pH, buffers, and other parameters will vary depending on the mode and site of administration (e.g., whether systemic, regional or local administration) and needs related to storage, handling, shipping, and shelf life of the particular pharmaceutical composition. Optimization of these parameters depending on the particular need of the formulation can be done by routine methods; and any of ingredients and parameters for known injectable formulations can be used. One example of a suitable formulation is, e.g., a recombinant wild type p53-expressing adenovirus vector of the invention (rAd5/p53) at a concentration of about $7.5 \times 10^{11}$ to $7.5 \times 10^{10}$ particles per ml, sodium phosphate monohydrate at 0.42 mg/ml, sodium phosphate dibasic anhydride at 2.48 mg/ml, sodium chloride at sodium phosphate monohydrate at 5.8 mg/ml, sucrose at 20.0 mg/ml, magnesium chloride hexahydrate at 0.40 mg/ml, typically stored in 1.0 ml dosages. An exemplary formulation for enhanced stability during storage and distribution, especially at refrigeration temperatures, uses rAd5/p53 (at also about $7.5 \times 10^{11}$ to $7.5 \times 10^{10}$ particles per ml), sodium phosphate monobasic dihydrate at 1.7 mg/ml, tromethamine (Trizma, or, Tris base, Sigma Chemical Co., St. Louis, Mo.) at 1.7 mg/ml, magnesium chloride hexahydrate at 0.4 mg/ml, sucrose at 20 mg/ml, polysorbate 80 at 0.15 mg/ml, glycerol at 100 mg/ml, typically stored in 1.0 ml dosages.

Cells transduced by the packaged nucleic acid as described above in the context of ex vivo therapy can also be administered intravenously or parenterally as described above.

The dose administered to a patient, in the context of the present invention, should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment, the physician evaluates circulating plasma levels of the vector, vector toxicities, progression of the disease, and the production of anti-vector antibodies. The typical dose for a nucleic acid is highly dependent on route of administration and gene delivery system. Depending on delivery method the dosage can easily range from about 1 μg to 100 mg or more. In general, the dose equivalent of a naked nucleic acid from a vector is from about 1 μg to 100 μg for a typical 70 kilogram patient, and doses of vectors which include a viral particle are calculated to yield an equivalent amount of therapeutic nucleic acid.

For administration, transduced cells of the present invention can be administered at a rate determined by the $LD_{50}$ of the vector, or transduced cell type, and the side-effects of the vector or cell type at various concentrations, as applied to the mass and overall health of the patient. Administration can be accomplished via single or divided doses as described below.

In a preferred embodiment, prior to infusion, blood samples are obtained and saved for analysis. Vital signs and oxygen saturation by pulse oximetry are closely monitored. Blood samples are preferably obtained 5 minutes and 1 hour following infusion and saved for subsequent analysis. In ex vivo therapy, leukopheresis, transduction and reinfusion can be repeated are repeated every 2 to 3 months. After the first treatment, infusions can be performed on a outpatient basis at the discretion of the clinician. If the reinfusion is given as an outpatient, the participant is monitored for at least 4, and preferably 8 hours following the therapy.

As described above, the adenoviral constructs can be administered systemically (e.g., intravenously), regionally (e.g., intraperitoneally) or locally (e.g., intra- or peri-tumoral or intracystic injection, e.g., to treat bladder cancer). Particularly preferred modes of administration include intra-arterial injection, more preferably intra-hepatic artery injection (e.g., for treatment of liver tumors), or, where it is desired to deliver a composition to a brain tumor, a carotid artery or an artery of the carotid system of arteries (e.g., occipital artery, auricular artery, temporal artery, cerebral artery, maxillary artery, etc.). Delivery for treatment of lung cancer can be accomplished, e.g., by use of a bronchoscope. Typically such administration is in an aqueous pharmacologically acceptable buffer as described above. However, on one particularly preferred embodiment, the adenoviral constructs or the tumor suppressor expression cassettes are administered in a lipid formulation, more particularly either complexed with liposomes to for lipid/nucleic acid complexes (e.g., as described by Debs and Zhu (1993) WO 93/24640; Mannino (1988) supra; Rose, U.S. Pat. No. 5,279, 833; Brigham (1991) WO 91/06309; and Felgner (1987) supra) or encapsulated in liposomes, more preferably in immunoliposomes directed to specific tumor markers. It will be appreciated that such lipid formulations can also be administered topically, systemically, or delivered via aerosol.

4. Enhancing Tumor Suppressor Delivery

Tumor suppressor delivery can be enhanced by the use of one or more "delivery-enhancing agents". A "delivery-enhancing agent" refers to any agent which enhances delivery of a therapeutic gene, such as a tumor suppressor gene to a cancerous tissue or organ. Such enhanced delivery may be achieved by various mechanisms. One such mechanism may involve the disruption of the protective glycosaminoglycan layer on the epithelial surface of an organ or tissue (e.g., the bladder). Examples of such delivery-enhancing agents are detergents, alcohols, glycols, surfactants, bile salts, heparin antagonists, cyclooxygenase inhibitors, hypertonic salt solutions, and acetates. Alcohols include for example the aliphatic alcohols such as ethanol, N-propanol, isopropanol, butyl alcohol, acetyl alcohol. Glycols include glycerine, propyleneglycol, polyethyleneglycol and other low molecular weight glycols such as glycerol and thioglycerol. Acetates such as acetic acid, gluconol acetate, and sodium acetate are further examples of delivery-enhancing agents. Hypertonic salt solutions like 1M NaCl are also examples of delivery-enhancing agents. Examples of surfactants are sodium dodecyl sulfate (SDS) and lysolecithin, polysorbate 80, nonylphenoxypolyoxyethylene, lysophosphatidylcholine, polyethylenglycol 400, polysorbate 80, polyoxyethylene ethers, polyglycol ether surfactants and DMSO. Bile salts such as taurocholate, sodium tauro-deoxycholate, deoxycholate, chenodesoxycholate, glycocholic acid, glycochenodeoxycholic acid and other astringents like silver nitrate may be used. Heparin-antagonists like quaternary amines such as prolamine sulfate may also be used. Cyclooxygenase inhibitors such as sodium salicylate, salicylic acid, and non-steroidal anti-inflammatory drug (NSAIDS) like indomethacin, naproxen, diclofenac may be used.

Detergents include anionic, cationic, zwitterionic, and nonionic detergents. Exemplary detergents include but are not limited to taurocholate, deoxycholate, taurodeoxycholate, cetylpyridium, benalkonium chloride, ZWITTER-GENT®3-14 detergent, CHAPS (3-[(3-Cholamidopropyl) dimethylammoniol]-1-propanesulfonate hydrate, Aldrich), Big CHAP (as described in U.S. Ser. No. 08/889,355, filed Jul. 8, 1997; and, International Application WO 97/25072, Jul. 17, 1997), Deoxy Big CHAP (ibid), TRITON®-X-100 detergent, C12E8, Octyl-B-D-Glucopyranoside, PLURONIC®-F68 detergent, TWEEN® 20 detergent, and TWEEN® 80 detergent (CALBIOCHEM® Biochemicals).

In an embodiment, the delivery-enhancing agent is included in the buffer in which the recombinant adenoviral vector delivery system is formulated. The delivery-enhancing agent may be administered prior to the recombinant virus or concomitant with the virus. In some embodiments, the delivery-enhancing agent is provided with the virus by mixing a virus preparation with a delivery-enhancing agent formulation just prior to administration to the patient. In other embodiments, the delivery-enhancing agent and virus are provided in a single vial to the care giver for administration.

In the case of a pharmaceutical composition comprising a tumor suppressor gene contained in a recombinant adenoviral vector delivery system formulated in a buffer which further comprises a delivery-enhancing agent, the pharmaceutical composition is preferably be administered over time in the range of about 5 minutes to 3 hours, preferably about 10 minutes to 120 minutes, and most preferably about 15 minutes to 90 minutes. In another embodiment the delivery-enhancing agent may be administered prior to administration of the recombinant adenoviral vector delivery system containing the tumor suppressor gene. The prior administration of the delivery-enhancing agent may be in the range of about 30 seconds to 1 hour, preferably about 1 minute to 10 minutes, and most preferably about 1 minute to 5 minutes prior to administration of the adenoviral vector delivery system containing the tumor suppressor gene.

The concentration of the delivery-enhancing agent will depend on a number of factors known to one of ordinary skill in the art such as the particular delivery-enhancing agent being used, the buffer, pH, target tissue or organ and mode of administration. The concentration of the delivery-enhancing agent will be in the range of 1% to 50% (v/v), preferably 10% to 40% (v/v) and most preferably 15% to 30% (v/v). Preferably, the detergent concentration in the final formulation administered to the patient is about 0.5–2× the critical micellization concentration (CMC). A preferred concentration of Big CHAP is about 2–20 mM, more preferable about 3.5–7 mM.

The buffer containing the delivery-enhancing agent may be any pharmaceutical buffer such as phosphate buffered saline or sodium phosphate/sodium sulfate, Tris buffer, glycine buffer, sterile water and other buffers known to the ordinarily skilled artisan such as those described by Good et al. (1966) *Biochemistry* 5:467. The pH of the buffer in the pharmaceutical composition comprising the tumor suppressor gene contained in the adenoviral vector delivery system, may be in the range of 6.4 to 8.4, preferably 7 to 7.5, and most preferably 7.2 to 7.4.

A preferred formulation for administration of a recombinant adenovirus is about $10^9$–$10^{11}$ PN/ml virus, about 2–10 mM Big CHAP or about 0.1–1.0 mM TRITON®-X-100 detergent, in phosphate buffered saline (PBS), plus about 2–3% sucrose (w/v) and about 1–3 mM $MgCl_2$, at about pH 6.4–8.4. The use of delivery-enhancing agents is described in detail in copending in copending application U.S. Ser. No. 08/779,627 filed on Jan. 7, 1997.

In order to facilitate the improved gene transfer for nucleic acid formulations comprising commercial Big-CHAP preparations, the concentration of Big CHAP will vary based on its commercial source. When the Big CHAP is sourced from CALBIOCHEM, it is preferred that the concentration be in a range of 2 to 10 millimolar. More preferred is 4 to 8 millimolar. Most preferred is approximately 7 millimolar.

When the Big CHAP is sourced from Sigma, it is preferred that the concentration of Big CHAP be in a range of 15 to 35 millimolar. More preferred is 20 to 30 millimolar. Most preferred is approximately 25 millimolar.

In a further embodiment of the invention, delivery-enhancing agents having Formula I are provided:

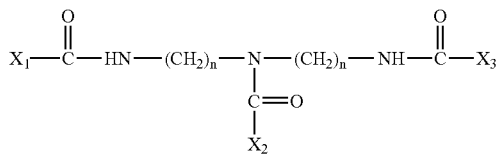

wherein n is an integer from 2–8, $X_1$ is a cholic acid group or deoxycholic acid group, and $X_2$ and $X_3$ are each independently selected from the group consisting of a cholic acid group, a deoxycholic acid group, and a saccharide group. At least one of $X_2$ and $X_3$ is a saccharide group. The saccharide group may be selected from the group consisting of pentose monosaccharide groups, hexose monosaccharide groups, pentose-pentose disaccharide groups, hexose-hexose disaccharide groups, pentose-hexose disaccharide groups, and hexose-pentose disaccharide groups. In one preferred embodiment, the compounds of the present invention have the Formula II:

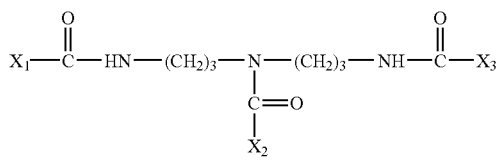

wherein $X_1$ and $X_2$ are selected from the group consisting of a cholic acid group and a deoxycholic acid group and $X_3$ is a saccharide group.

These compounds are preferably used in the range of about 0.002 to 2 mg/ml, more preferably about 0.02 to 2 mg/ml, most preferably about 0.2 to 2 mg/ml in the formulations of the invention. Most preferred is approximately 2 mg/ml.

Phosphate buffered saline (PBS) is the preferred solubilizing agent for these compounds. However, one of ordinary skill in the art will recognize that certain additional excipients and additives may be desirable to achieve solubility characteristics of these agents for various pharmaceutical formulations. For examples, the addition of well known solubilizing agents such as detergents, fatty acid esters, surfactants may be added in appropriate concentrations so as to facilitate the solubilization of the compounds in the various solvents to be employed. When the solvent is PBS, a preferred solubilizing agent is Tween 80 at a concentration of approximately 0.15%.

5. Administration of Tumor Suppressor Proteins

Tumor suppressor proteins (polypeptides) can be delivered directly to the tumor site by injection or administered systemically as described above. In a preferred embodiment, the tumor suppressor proteins are combined with a pharmaceutically acceptable carrier (excipient) to form a pharmacological composition as described above. The tumor suppressor polypeptide will be administered in a therapeutically effective dose. Thus the compositions will be administered in an amount sufficient to cure or at least partially arrest the disease and/or its complications. Amounts effective for this use will depend upon the severity of the disease and the general state of the patient's health.

It will be recognized that tumor suppressor polypeptides, when administered orally, must be protected from digestion. This is typically accomplished either by complexing the polypeptide with a composition to render it resistant to acidic and enzymatic hydrolysis or by packaging the polypeptide in an appropriately resistant carrier such as a liposome as described above. Means of protecting polypeptides for oral delivery are well known in the art (see, e.g., U.S. Pat. No. 5,391,377 describing lipid compositions for oral delivery of therapeutic agents).

III. Combination Pharmaceuticals

The tumor suppressor and the adjunctive anti-cancer agent can be administered individually with either the tumor suppressor nucleic acid or polypeptide being administered before the adjunctive anti-cancer (tumor suppressor pretreatment) or the adjunctive anti-cancer being administered before the tumor suppressor nucleic acid and/or polypeptide (cancer drug pretreatment). Of course the tumor suppressor nucleic acid and/or polypeptide and the adjunctive anti-cancer agent can be administered simultaneously.

In one embodiment, the tumor suppressor nucleic acid and/or polypeptide and the adjunctive anti-cancer agent are administered as a single pharmacological composition. In this embodiment, the tumor suppressor nucleic acid and/or polypeptide and the adjunctive anti-cancer agent can be suspended or solubilized in a single homogeneous delivery vehicle. Alternatively the tumor suppressor nucleic acid and/or polypeptide and the adjunctive anti-cancer agent can each be suspended or solubilized in different delivery vehicles which in turn are suspended (disbursed) in single excipient either at the time of administration or continuously. Thus, for example, an adjunctive anti-cancer agent may be solubilized in a polar solvent (e.g., paclitaxel in ethanol) and the tumor suppressor nucleic acid may be complexed with a lipid which are then either stored together in a suspension or, alternatively are combined at the time of administration. Various suitable delivery vehicles, excipients, etc., are described above.

IV. Treatment Regimen: Combined and Individual Therapy

A) Tumor Suppressor Treatment Regimen

It was a discovery of this invention that tumor suppressor nucleic acids or polypeptides, more particularly tumor suppressor nucleic acids show greater efficacy in inhibiting tumor growth when administered in multiple doses rather than in a single dose. Thus this invention provides a treatment regimen for a tumor suppressor gene or polypeptide that comprises multiple administrations of the tumor suppressor nucleic acid or polypeptide.

The tumor suppressor protein or tumor suppressor nucleic acid may be administered (with or without an adjunctive anti-cancer agent) in a total dose ranging from about $1 \times 10^9$ to about $1 \times 10^{14}$, about $1 \times 10^9$ to about $7.5 \times 10^{15}$, preferably about $1 \times 10^{11}$ to about $7.5 \times 10^{13}$, adenovirus particles in a treatment regimen selected from the group consisting of: the total dose in a single dose, the total dose divided over 5 days or administered daily for 5 days, the total dose divided over 15 days or administered daily for 15 days, and the total dose divided over 30 days or administered daily for 30 days. This method of administration can be repeated for two or more cycles (more preferably for three cycles) and the two or more cycles are can be spaced apart by three or four weeks. The treatment may consist of a single dosage cycle or dosage cycles may range from about 2 to about 12, more preferably from about 2 to about 6 cycles.

Particularly preferred treatment regimen include the total dose divided over 5 days and administered daily, the total dose divided over 15 days and administered daily, and the total dose divided over 30 days and administered daily.

In some preferred embodiments, a daily dose in the range of $7.5 \times 10^9$ to about $7.5 \times 10^{15}$, preferably about $1 \times 10^{12}$ to about $7.5 \times 10^{13}$, adenovirus particles can be administered each day for up to 30 days (e.g., a regimen of 2 days, 2 to 5 days, 7 days, 14 days, or 30 days with the same dose being administered each day). The multiple regimen can be repeated in recurring cycles of 21 to 28 days.

In some embodiments, different routes of administration will result in use of different preferred dosage ranges. For instance, for intra-hepatic arterial delivery, a preferred range will typically be between $7.5 \times 10^9$ and about $1 \times 10^{15}$, more preferably about $1 \times 10^{11}$ to about $7.5 \times 10^{13}$, adenovirus particles per day for 5 to 14 days. These regimens can further include administration of adjunctive anti-cancer agents, FUDR or 5'-deoxy-5-fluorouridine (5'-DFUR), or irinotecan hydrochloride (CPT-11; 7-ethyl-10-[4-(1-piperidino)-1-piperidino]carbonyloxycamptothecin). For intratumoral delivery, a preferred range will typically be between $7.5 \times 10^9$ and about $1 \times 10^{13}$, more preferably about $1 \times 10^{11}$ to about $7.5 \times 10^{12}$, adenovirus particles per day. For intraperitoneal delivery, a preferred range will typically be between $7.5 \times 10^9$ and about $1 \times 10^{15}$, more preferably about $1 \times 10^{11}$ to about $7.5 \times 10^{13}$, adenovirus particles per day for 5–10 days.

B) Combination Therapy Treatment Regimen

Where the tumor suppressor is used in combination with an adjunctive anti-cancer agent the tumor suppressor nucleic acid is administered in total dose as described above. In combination, the adjunctive anti-cancer agent is administered in a total dose dependent upon the agent used. For instance, paclitaxel or a paclitaxel derivative is administered in a total dose ranging from 75–350 mg/m$^2$ over 1 hour, 3 hours, 6 hours, or 24 hours in a treatment regimen selected from the group consisting of administration in a single dose, in a dose administered daily on day 1 and day 2, in a dose administered daily on day 1, day 2, and day 3, on a daily dosage for 15 days, on a daily dosage for 30 days, on daily continuous infusion for 15 days, on daily continuous infusion for 30 days. A preferred dose is 100–250 mg/m$^2$ in 24 hours.

Pretreatment with an adjunctive anti-cancer agent (e.g., paclitaxel) prior to treatment with a tumor suppressor nucleic acid enhances the efficacy of the tumor suppressor. Thus, in one particularly preferred embodiment the cell, tissue, or organism is treated with the adjunctive anti-cancer agent prior to the tumor suppressor nucleic acid. The adjunctive anti-cancer agent treatment preferably precedes the tumor suppressor nucleic acid treatment by about twenty four hours although longer or shorter periods are acceptable.

The pretreatment is particularly efficacious when the adjunctive anti-cancer agent is a paclitaxel-like compound, more preferably paclitaxel or a paclitaxel derivative (e.g., TAXOL® or (TAXOTERE®). Particularly preferred tumor suppressors are RB and p53 with p53 being most preferred, in particular p53 in an adenoviral vector (e.g., A/C/N/53).

V. Treatment of and Prophylaxis for Metastases

As illustrated in Examples 2 and 3, tumor suppressor (e.g., p53) gene replacement therapy has been demonstrated to have efficacy against human tumor cells in vitro, human tumor xenografts in immunocompromised hosts, and human lung tumors (in vivo). Surgical debulking of primary tumors in patients often results in tumor regrowth at the primary site and tumor metastasis from that site due to microscopic "nests" of tumor cells which are missed by the surgeon. Alternatively, in order to make sure that all the tumor is removed from a primary site, the patient may be subjected to disfiguring surgery which removes a large amount of normal tissue surrounding the primary tumor site.

In another embodiment, this invention provides methods of inhibiting the growth and/or proliferation of metastases (metastatic cells). The method generally involves either systemic or topical administration of a tumor suppressor, more preferably topical administration of p53 or RB.

A) Systemic Treatment

As explained in Examples 2 and 3, systemic treatment (e.g., intravenous injection) of tumor suppressor vectors (e.g., A/C/N/53) inhibited the progression of metastases in vivo. Thus, in one embodiment, this invention provides methods for inhibiting the progression of metastatic disease by administering to an organism a tumor suppressor nucleic acid and/or a tumor suppressor polypeptide as described above. The tumor suppressor is preferably a tumor suppressor nucleic acid, more preferably a p53 tumor suppressor nucleic acid and most preferably a p53 nucleic acid in an adenoviral vector (e.g. A/C/N/53). In another preferred embodiment, the tumor suppressor nucleic acid is provided encapsulated in a liposome or complexed to a lipid (see, e.g., Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Natl. Acad. Sci. USA* 84: 7413–7414).

B) Topical Treatment

In another embodiment, topical application of the tumor suppressor protein or tumor suppressor nucleic acid is preferred in conjunction with surgery. In this embodiment, the tumor suppressor, preferably in the form of an infectious vector, is applied along the surface of the wound cavity after tumor removal. The infectious particles will carry p53 into any residual tumor cells at the wound site, inducing their apoptosis (programmed cell death). This treatment will impact long-term patient survival and/or reduce the amount of normal tissue surrounding the tumor site which needs to be removed during surgery.

The tumor suppressor is preferably compounded in one of the many formulations known by those of skill in the art to be suitable for topical application. Thus, for example, an infections preparation of the human p53 tumor suppressor gene (e.g., A/C/N/53) is suspended in a suitable vehicle (e.g., petroleum jelly or other cream or ointment) which is suitable for spreading along the surface of the wound cavity. Alternatively, the tumor suppressor can be prepared in an aerosol vehicle for application as a spray inside the wound cavity. In other embodiments, the tumor suppressor can be prepared in degradable (resorbable) materials, e.g, resorbable sponges, that can be packed into the wound cavity and which release the tumor suppressor protein or vector in a time-dependent manner.

Preferred embodiments for application of recombinant adenoviral vectors to certain defined topical areas, e.g., cornea, gastro-intestinal tract, tumoral resection sites use solid carriers to support a longer incubation time and facilitate viral infection. Carriers can be gauze or ointments soaked with the recombinant adenovirus solution. The virus can be applied via the gauze support to the cornea to achieve improved transgene effects. The drained gauze can also be prophylactically applied to resected tumor areas in order to avoid recurrence. Ointments can be applied topically to areas of the gastrointestinal tract, or topically to areas of the pancreas for tumor suppressor gene therapy.

Exemplary ointment carriers include petroleum based PURALUBE® or water soluble KY-JELLY®. In an exemplary method, sterile gauze pads (5×5 cm) or tear flow test strips can be soaked in an adenoviral vector solution (e.g., $1\times10^9$ PN/ml) until totally wet. The pads or strips are layered on top of the target tissue and incubated at 37 degrees C. for 30 minutes. One of skill will recognize that other fabrics, gelatins, or ointments can be included that can take up or be mixable with water. In addition, other excipients may be added that can enhance gene transfer as described above.

VI. Combination Treatments With Other Chemotherapeutics

A) Tumor Suppressors Administered in Combination With Multiple Chemotherapeutic Combinations It will be appreciated that the methods of this invention are not limited to combination of a tumor suppressor with a single adjunctive anti-cancer agent. While methods typically involve contacting a cell with a tumor suppressor (e.g., p53) and an adjunctive anti-cancer agent such as paclitaxel, the methods of the invention also entail contacting the cell with a combination of a tumor suppressor gene or polypeptide and two, three or a multiplicity of adjunctive anti-cancer agents and optionally other chemotherapeutic drugs. In addition, one of skill will recognize that a chemotherapeutic agent(s) can also be used with tumor suppressor proteins or genes, in the absence of an adjunctive anti-cancer agent(s).

Many chemotherapeutic drugs are well known in the scientific and patent literature; exemplary drugs that can be used in the methods of the invention include but are not limited to: DNA damaging agents (including DNA alkylating agents) e.g., cisplatin, carboplatin (see, e.g., Duffull (1997) *Clin Phannacokinet.* 33:161–183); Droz (1996) *Ann Oncol.* 7:997–1003), navelbine (vinorelbine), Asaley, AZQ, BCNU, Busulfan, carboxyphthalatoplatinum, CBDCA, CCNU, CHIP, chlorambucil, chlorozotocin, cis-platinum, clomesone, cyanomorpholino-doxorubicin, cyclodisone, cytoxan, dianhydrogalactitol, fluorodopan, hepsulfam, hycanthone, melphalan, methyl CCNU, mitomycin C, mitozolamide, nitrogen mustard, PCNU, piperazine alkylator, piperazinedione, pipobroman, porfiromycin, spirohydantoin mustard, teroxirone, tetraplatin, thio-tepa, triethylenemelamine, uracil nitrogen mustard, Yoshi-864); topoisomerase I inhibitors (e.g., topotecan hydrochloride, irinotecan hydrochloride (CPT 11), camptothecin, camptothecin Na salt, aminocamptothecin, CPT-11 and other camptothecin derivatives); topoisomerase II inhibitors (doxorubicin, including doxorubicin encapsulated in liposomes (see, U.S. Pat. Nos. 5,013,556 and 5,213,804) amonafide, m-AMSA, anthrapyrazole derivatives, pyrazoloacridine, bisantrene HCL, daunorubicin, deoxydoxorubicin, mitoxantrone, menogaril, N,N-dibenzyl daunomycin, oxanthrazole, rubidazone, VM-26, and VP-16); RNA/DNA antimetabolites (e.g., L-alanosine, 5-azacytidine, 5-fluorouracil, acivicin, aminopterin, aminopterin derivatives, an antifol, Baker's soluble antifol, dichlorallyl lawsone, brequinar, ftorafur (pro-drug), 5,6-dihydro-5-azacytidine, methotrexate, methotrexate derivatives, N-(phosphonoacetyl)-L-aspartate (PALA), pyrazofurin, and trimetrexate); and, DNA antimetabolites (e.g., 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole, hydroxyurea, inosine, glycodialdehyde, macbecin II, pyrazoloimidazole, thioguanine, and thiopurine). The tumor suppressor nucleic acid and/or polypeptide can also be administered in combination with chemotherapeutic agents such as vincristine, temozolomide (see, e.g., U.S. Pat. No. 5,260,291), and toremifene (see, e.g., U.S. Pat. No. 4,696,949 for information on toremifene).

Preclinical studies in relevant animal models have shown that p53 adenovirus combined with cisplatin, carboplatin, navelbine, doxorubicin, 5-fluorouracil, methotrexate, or etoposide, inhibited cell proliferation more effectively than chemotherapy alone treating the tumors: SSC-9 head and neck, SSC-15 head and neck, SSC-25 head and neck, SK-OV-3 ovarian, DU-145 prostate, MDA-MB-468 breast and MDA-MB-231 breast tumor cells. In another embodiment, an enhanced anti-tumor efficacy is seen using a three drug combination of p53 gene (expressed, e.g., in an adenovirus vector), an adjuctive anti-cancer agent (e.g., paclitaxel) and a DNA damaging agent (e.g., cisplatin). The combination of p53, paclitaxel and cisplatin has been shown to be effective in an ovarian tumor model. These data support the combination of p53 gene therapy with chemotherapy in clinical trials.

These other chemotherapeutic drugs can be used in combination with the tumor suppressor nucleic acid and/or polypeptide with or without the presence of an adjunctive anti-cancer agent. This invention also contemplates the use of radiation therapy in combination with any of the tumor suppressors described above or in conjunction with the tumor suppressors described above combined with an adjunctive anti-cancer agent.

It will also be appreciated that any of these chemotherapeutics can be used individually in combination with a tumor suppressor nucleic acid or polypeptide according to the methods of this invention.

When the tumor suppressor nucleic acid (e.g., p53) is administered in an adenoviral vector with an adjunctive anti-cancer agent (e.g., paclitaxel) and a DNA damaging agent (e.g., cisplatin, carboplatin, or navelbine), the adenoviral vector is typically administered for 5 to 14 days at about $7.5\times10^{12}$ to about $7.5\times10^{13}$ adenoviral particles per day. For example, a daily dose of about $7.5\times10^{13}$ adenoviral particles in combination with carboplatin can be used. In one embodiment, a daily dose of about $7.5\times10^{12}$ adenoviral particles can be used for administration to the lung. In another embodiment, p53 is administered with topotecan.

Typically, the DNA damaging agent will be administered at the recommended dose, see, e.g., *Physician's Desk Reference,* 51st ed. (Medical Economics, Montvale, N.J. 1997). For instance, carboplatin is administered to achieve an AUC (an area under the curve) of about 6–7.5 mg/ml/min.

Protease Inhibitors

In still another embodiment, this invention provides for the combined use of tumor suppressor nucleic acids and/or polypeptides and protease inhibitors. Particularly preferred protease inhibitors include, but are not limited to collagenase inhibitors, matrix metalloproteinase (MMP) inhibitors (see, e.g., Chambers (1997) *J. Natl. Cancer Inst.* 89:1260–1270). In a preferred embodiment, the methods comprise administering concurrently or sequentially, an effective amount of a protease inhibitor and an effective amount of a tumor suppressor polypeptide and/or nucleic acid. Examples of compounds that are protease inhibitors are well known in the scientific and patent literature.

Immunomodulators

The tumor suppressor proteins and nucleic acids of this invention can be used in conjunction with immunomodulators where the immunomodulators either upregulate an immune response directed against the hyperproliferative or cancer cell (e.g., an immune response directed against a tumor specific antigen) or downregulate an immune response directed against the tumor suppressor protein, tumor suppressor nucleic acid, tumor suppressor vector (e.g., anti-adenoviral reaction), and/or combined chemotherapeutic.

Thus, for example, this invention provides for the combined sequential or concurrent administration of an effective amount of a tumor suppressor nucleic acid and/or tumor suppressor polypeptide with an effective amount of an immunomodulator. Immunomodulators include, but are not limited to cytokines such as IL-2, IL-4, IL-10 (U.S. Pat. No. 5,231,012; Lalani (1997) *Ann. Allergy Asthma Immunol.* 79:469–483; Geissler (1996) *Curr. Opin. Hematol.* 3:203–208), IL-12 (see, e.g., Branson (1996) *Human Gene Ther.* 1:1995–2002), and gamma-interferon.

Immunomodulators that function as immunosuppressants can be utilized to mitigate an immune response targeted against the therapeutic (e.g., tumor suppressor protein or nucleic acid or adjunctive anticancer agent, etc.). Immunosuppressants are well known to those of skill in the art. Suitable immunosuppressants include, but are not limited to cyclo-phosphamide, dexamethasone, cyclosporin, FK506 (tacrolimus) (Lochmuller (1996) *Gene Therapy* 3:706–716) IL-10, and the like. Antibodies against cell surface receptors which modulate the immune response can also be used. For instance, antibodies that block ligand binding to cellular receptors on B cells, T cells, NK cells, macrophages, and tumor cells can be used for this purpose. For examples of this strategy see, e.g., Yang (1996) *Gene Therapy* 3:412–420; Lei (1996) *Human Gene Therapy* 7:2273–2279; Yang (1996) *Science* 275:1862–1867.

VII. Therapeutic Kits

In another embodiment, this invention provides for therapeutic kits. The kits include, but are not limited to a tumor suppressor nucleic acid or polypeptide or a pharmaceutical composition thereof. The kits may also include an adjunctive anti-cancer agent or a pharmaceutical composition thereof or pharmaceutical composition thereof. The various compositions may be provided in separate containers for individual administration or for combination before administration. Alternatively the various compositions may be provided in a single container. The kits may also include various devices, buffers, assay reagents and the like for practice of the methods of this invention. In addition, the kits may contain instructional materials teaching the use of the kit in the various methods of this invention (e.g., in the treatment of tumors, in the prophylaxis and/or treatment of metastases, and the like).

The kit can optionally include one or more immunomodulators (e.g., immunosuppressants). Particularly preferred immunomodulators include any of the immunomodulators described herein.

VIII. Cells Containing Heterologous Tumor Suppressor Nucleic Acids or Polypeptides, and Other Agents Further provided by this invention is a transfected or otherwise treated prokaryotic or eukaryotic host cell, for example an animal cell (e.g., a mammalian cell) containing a heterologous tumor suppressor nucleic acid and/or tumor suppressor polypeptide. The cell may optionally additionally contain an adjunctive anti-cancer agent, e.g. paclitaxel or other microtubule affecting agent.

Suitable prokaryotic cells include, but are not limited to bacterial cells such as *E. coli* cells. Suitable animal cells preferably include mammalian, more preferably human cells. Host cells include, but are not limited to any mammalian cell, more preferably any neoplastic or tumor cell such as any of the cells described herein.

The transfected host cells described herein are useful as compositions for diagnosis or therapy. When used pharmaceutically, they can be combined with various pharmaceutically acceptable carriers as described above for ex vivo gene therapy. The cells can be administered therapeutically or prophylactically in effective amounts described in detail above. In a diagnostic context, the cells may be used for teaching or other reference purposes and provide suitable models for identification of cells thus transfected and/or treated.

IX. Preclinical and Clinical Efficacy of p53 Adenovirus Gene Therapy

Adenovirus-mediated p53 gene therapy is currently undergoing phase I/II clinical trials in several countries. The pharmaceutical composition used in these clinical trials included an exemplary wild type p53-expressing adenovirus of the invention (rAd/p53) consisting of a replication-deficient, type 5 adenovirus vector expressing the human tumor suppressor gene under the control of the cytomegalovirus promoter ("rAd5/p53"), as described herein (see Wills (1994) supra).

Regional Administration

Ovarian cancer limited to the abdominal cavity is one clinical scenario in which regional p53 gene therapy, i.e., intraperitoneal administration, should be considered as a preferred treatment plan.

EXAMPLES

The following examples are offered to illustrate, but not to limit the claimed invention.

Example 1

Combination Therapy with p53 and TAXOL®

The invention provides for the combined administration of nucleic acid expressing a tumor suppressor polypeptide and paclitaxel in the treatment of neoplasms. The following example details the ability of a p53 expressing adenovirus of the invention in combination with TAXOL® to treat neoplasms, and that the combination therapy was more effective at killing tumor cells than either agent alone.

Combination Therapy in vitro

The cells were subjected to one of three treatment regimes: In treatment 1, the cells were pretreated with TAXOL® twenty-four hours before exposure to the p53 adenovirus construct A/C/N/53. In treatment two, the cells were pretreated with the p53 adenovirus construct and then later contacted with TAXOL®. In treatment three, the cells were contacted simultaneously with both the TAXOL® and the p53 adenovirus. Thus, the p53 Ad and TAXOL® can be administered within the same twenty four (24) hour period or concurrently.

Approximately $1.5 \times 10^4$ cells in culture medium (head and neck cell lines SCC-9, SCC-15, and SCC-25 in 1:1 mix of DMEM+ Ham's F12 media with 0;4 µg/ml cortisol and 10% FBS and 1% non-essential amino acids, prostate DU-145 and Ovarian SK-OV-3 in Eagles essential medium plus 10% FBS) were added to each well on a 96 well microtitre plate and cultured for about 4 hours at 37° C. and 5% $CO_2$. The drug (TAXOL®), the p53 adenovirus, or the appropriate vehicle/buffer was added to each well. As paclitaxel is not water soluble, the drug was dissolved in ethyl alcohol prior to administration. Cells were then cultured overnight at 37° C. and 5% $CO_2$. p53 adenoviruses were administered in phosphate buffer (20 mM $NaH_2PO_4$, pH 8.0, 130 mM NaCl, 2 mM $MgCl_2$, 2% sucrose).

Cell death was then quantitated according to the method of Mosmann (1983) *J. Immunol. Meth.*, 65: 55–63. Briefly, approximately 25 µl of 5 mg/ml MTT vital dye [3-(4,5 dimethylthiazol-2yl)-2,5-diphenyltetrazolium bromide] was added to each well and allowed to incubate for 3–4 hrs. at 37° C. and 5% $CO_2$. Then 100 µl of 10% SDS detergent was added to each well and allowed to incubate overnight at 37° C. and 5% $CO_2$. Signal in each well was then quantitated using a Molecular devices microtiter plate reader (Thermo-Max). The particular cell-lines used and the results obtained therefrom are listed in Table 1.

Table 1. In vitro evaluation of the adjunctive anti-cancer agent TAXOL® combined with tumor suppressor nucleic acid.

TABLE 1

In vitro evaluation of the adjunctive anti-cancer agent TAXOL® combined with tumor suppressor nucleic acid.

| Cell line Cancer | TAXOL® dose (µg/ml) | A/C/N/ 53 dose (m.o.i.) | Treatment TAXOL® pretreatment | p53 pretreatment | simultaneous |
|---|---|---|---|---|---|
| SK-OV-3 Ovarian cancer | 0.37 | 40 | additive effect $p \leq 0.0001$ | no effect $p > 0.2000$ | additive effect $p \leq 0.0001$ |
| SCC-25 Head and neck cancer | 0.10 or 0.01 | 2.5 or 5.0 | additive effect $p \leq 0.0001$ | very small effect $p = 0.0606$ | additive effect $p \leq 0.0001$ |
| SCC-15 Head and neck cancer | 0.10 or 0.01 | 2.5 or 5.0 | additive effect $p \leq 0.002$ | additive effect $p \leq 0.0001$ | additive effect $p \leq 0.0001$ |
| DU-145 prostate cancer | 0.36 or 0.036 or 0.0036 | 2.5 or 5.0 | additive effect $p \leq 0.03$ | additive effect $p \leq 0.0001$ | additive effect $p \leq 0.0001$ |
| SCC-9 Head and neck cancer | 0.12 or 0.012 or 0.0012 | 2.5 or 5.0 | additive effect $p \leq 0.01$ | additive effect $p \leq 0.0001$ | additive effect $p \leq 0.0001$ |

In general, the p53 adenovirus was more effective when added after or concurrently with TAXOL® than when it was added first. These results suggest a synergistic interaction between A/C/N/53 and TAXOL®.

Isobologram Analysis Establishes Synergistic Effect.

SK-OV-3 (p53 null) ovarian tumor cells were treated with combinations of TAXOL® and p53/adenovirus (A/C/N/53) as illustrated in Table 2. Dosing was performed as described above. Cell death was quantitated on day 3 using the MTT assay as described above. In addition, a dose response curve for p53 Ad alone (using the doses listed in Table 2) was generated (after 2 day cell exposure to the drug) and a dose response curve for TAXOL® alone was performed using the doses listed above (3 day cell exposure to the drug).

Table 2. Treatment groups for combined TAXOL® and p53 Ad (A/C/N/53) treatments.

TABLE 2

Treatment groups for combined TAXOL® and p53 Ad (A/C/N/53) treatments.

| Group | TAXOL® (µg/ml) | p53 AD (m.o.i.) |
|---|---|---|
| 1 | 0.001 | 0.5 |
| 2 | 0.01 | 0.5 |
| 3 | 0.1 | 0.5 |
| 4 | 0.5 | 0.5 |
| 5 | 1 | 0.5 |
| 6 | 5 | 0.5 |
| 7 | 10 | 0.5 |
| 8 | 20 | 0.5 |
| 9 | 0.001 | 1 |
| 10 | 0.01 | 1 |
| 11 | 0.1 | 1 |
| 12 | 0.5 | 1 |
| 13 | 1 | 1 |
| 14 | 5 | 1 |
| 15 | 10 | 1 |
| 16 | 20 | 1 |
| 17 | 0.001 | 5 |
| 18 | 0.01 | 5 |
| 19 | 0.1 | 5 |
| 20 | 0.5 | 5 |
| 21 | 1 | 5 |
| 22 | 5 | 5 |
| 23 | 10 | 5 |
| 24 | 20 | 5 |
| 25 | 0.001 | 10 |
| 26 | 0.01 | 10 |
| 27 | 0.1 | 10 |
| 28 | 0.5 | 10 |
| 29 | 1 | 10 |
| 30 | 5 | 10 |
| 31 | 10 | 10 |

TABLE 2-continued

Treatment groups for combined TAXOL ®
and p53 Ad (A/C/N/53) treatments.

| Group | TAXOL ® (µg/ml) | p53 AD (m.o.i.) |
|---|---|---|
| 32 | 20 | 10 |
| 33 | 0.001 | 25 |
| 34 | 0.01 | 25 |
| 35 | 0.1 | 25 |
| 36 | 0.5 | 25 |
| 37 | 1 | 25 |
| 38 | 5 | 25 |
| 39 | 10 | 25 |
| 40 | 20 | 25 |
| 41 | 0.001 | 50 |
| 42 | 0.01 | 50 |
| 43 | 0.1 | 50 |
| 44 | 0.5 | 50 |
| 45 | 1 | 50 |
| 46 | 5 | 50 |
| 47 | 10 | 50 |
| 48 | 20 | 50 |

FIG. 1 illustrates the inhibition of cell proliferation (as compared to the buffer control) as a function of treatment. In general increasing doses of either TAXOL® or p53 decreased the rate of cell proliferation with the combination of p53 and TAXOL® having a greater effect than either drug alone.

Figure 2:
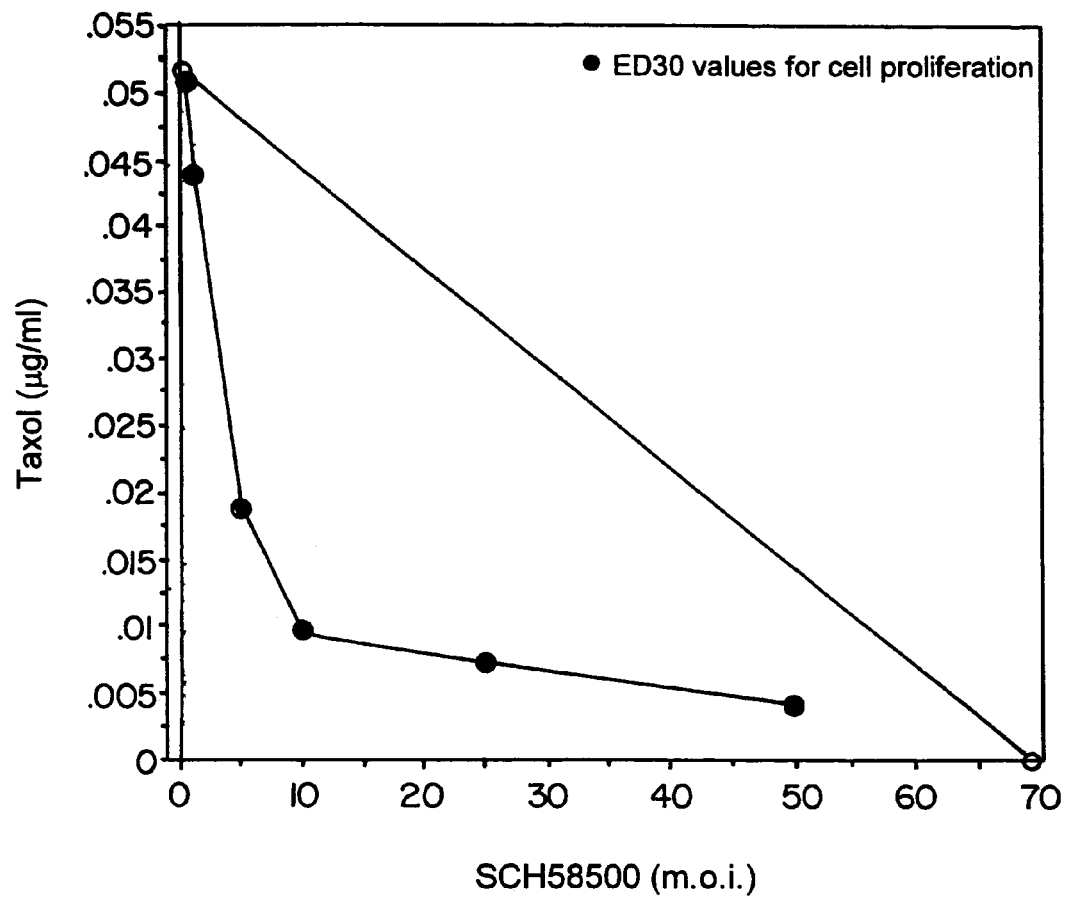
FIG. 2 provides an isobologram analysis for the experiments illustrated in FIG. 1. Synergism between TAXOL® and p53 (A/C/N/53) was observed when the cells were pretreated with TAXOL® 24 hours before p53 treatment.

FIG. 2 illustrates an isobologram analysis of these data using the Isobole method as reviewed by Berenbaum (1989) *Pharmacol. Rev.* 93–141. Synergism between TAXOL® and p53 (A/C/N/53) was observed when cells were pretreated with TAXOL® 24 hours before p53 (A/C/N/53) treatment. In FIG. 2, the straight line (isobole for $ED_{30}$) represents the effects on cell proliferation which would be expected if treatment with the two drugs were merely additive. In fact, the observed effects fall to the lower left of the isobole line indicating that lower than predicted concentrations of each drug were needed and a synergistic interaction between the two drugs has occurred.

Example 2 p53 Adenovirus-Mediated Gene Therapy Against Metastases

The invention provides for the administration of nucleic acid expressing a tumor suppressor polypeptide in the treatment of metastases. The following example details the ability of a p53 expressing adenovirus of the invention to infect various tissues in the body and to treat metastases.

Female scid mice (mice homozygous for the SCID mutation lack both T and B cells due to a defect in V(D)J recombination) were injected with $5 \times 10^6$ MDA-MB-231 mammary carcinoma cells into their mammary fat pads. After the primary tumors were well established and had time to metastasize to the lungs, the primary tumors were surgically removed (on day 11). Mice were treated with intravenous A/C/N/53 or with control buffer on days 23, 30, 37, 44 (1qW) with control buffer or with A/C/N/53 (a p53 in an adenovirus) at $4 \times 10^8$ C.I.U./injection. On day 49, the lungs were harvested, fixed, stained and examined microscopically.

The results are illustrated below in Table 3.

TABLE 3

Inhibition of MDA-MB-231 lung metastases using A/C/N/53

| Treatment | No Metastases | ≦6 Metastases | ≧84 Metastases |
|---|---|---|---|
| Buffer n = 17 | 11 (65%) | 1 (6%) | 5 (29%) |
| A/C/N/53 n = 10 | 5 (50%) | 4 (40%) | 1 (10%) |

The A/C/N/53 treatment decreased the number of metastases in the mice that had them.

In a second experiment, 231 tumors in the mammary fat pads of scid or scid-beige mice were given peritumoral injections with A/C/N/53. A total dose of $2-4 \times 10^9$ C.I.U. given in 10 injections decreased the number of mice with lung metastases by 80% in scid mice and 60% in scid-beige mice. Also the number of metastases per mouse was dramatically reduced in mice with any lung tumors at all. As indicated above, intravenous dosing with A/C/N/53 also demonstrated efficacy against lung metastases in scid mice. These data indicate that cancer gene therapy with A/C/N/53 may impact the severity of metastatic disease in addition to decreasing primary tumor burden.

In another experiment, female scid mice were injected with $5 \times 10^6$ MDA-MB-231 mammary tumor cells/mouse into the mammary fat pad on day 0. The primary (mammary) tumors were surgically removed on day 18. The mice were treated with intravenous injections of buffer, beta-gal AD, or p53 Ad (A/C/N/53) on days 21, 24, 32, 39, and 36. The virus dose per injection was $4 \times 10^8$ C.I.U. (A/C/N/53) (PN/C.I.U.=23.3) and $9.3 \times 10^9$ particles beta-gal Ad (PN/C.I.U.=55.6; $1.7 \times 10^8$ C.I.U.).

Lungs and livers were harvested on day 51 and fixed in formalin. Tissue sections were evaluated for lung tumors and for liver damage. Major organs from 2 buffer and 2 beta-gal Ad mice were flash-frozen for cryosectioning and analysis of B-galactosidase enzyme activity.

TABLE 4

Inhibition of MDA-MB-231 lung metastases using A/C/N/53

| Lung Metastases per Mouse | Buffer Gp.* | Beta-gal Ad Gp.* | p53 Ad Grp. |
|---|---|---|---|
| ≦20 | 11% (1) | 8% (1) | 21% (3) |
| >20 and ≦100 | 11% (1) | 33% (4) | 79% (11) |
| >100 and ≦200 | 33% (3) | 33% (4) | 0% (0) |
| >200 and ≦300 | 33% (3) | 17% (2) | 0% (0) |
| >300 | 11% (1) | 8% (1) | 0% (0) |
| Total number evaluated | 9 | 12 | 14 |
| Regrowth of primary tumor | 82% (9/11) | 88% (14/16) | 100% (14/14) |

*Number of metastases is under-estimated. Multiple tumors had grown together in these lungs.

The number of metastases per lung in the buffer and beta-gal Ad groups was not significantly different (p=0.268, see Table 4).

p53 Ad treatment significantly reduced the number of metastases per lung when compared to either the buffer of beta-gal Ad groups (p<0.001 and p<0.002, respectively). In addition to the reduction in the number of metastases, there was also a dramatic reduction in the size of lung metastases in the p53 Ad group. In the control groups, tissue sections from most lungs were>50% occupied by neoplastic tissue and individual tumors were no longer recognizable over large areas of the lungs. In contrast, lung metastases in most of the p53 Ad group were small and easily distinguishable as individual tumors.

Adenovirus Tissue Distribution

Liver tissues had the highest number of infected cells (about 50%) and beta-galactosidase activity was intense. Lung had scattered patches of infected cells evenly distributed throughout the tissue. Intestines and stomach had periodic infection of cells in the outer smooth muscle wall surrounding the organs. There was also beta-galactosidase activity in scattered microvilli along the lumen. The smooth outer muscle wall surrounding the uterus had periodic infection of cells similar to that seen in the intestines. Most stromal cells in the ovary were infected. The spleen had scattered beta-galactosidase activity in the smooth muscle components of the organ. There were very few infected cells (<1%) inside the main bulk of striated heart muscle. There were almost no infected cells in primary tumors in the mammary fat pad, nor in the underlying striated muscle. There were no infected cells in the kidney.

Liver Pathology

All livers were grossly normal when necropsied. There was no overt necrosis in any liver. However, mice treated with adenovirus did have hepatocellular abnormalities (not present in the buffer group) which included elevated numbers of cells in mitosis, cellular inclusions, and changes in hepatocyte size and shape.

Example 3 p53 Adenovirus-mediated Gene Therapy Against Human Breast Cancer Xenografts

The invention provides for the treatment of various cancers by the administration of nucleic acid expressing a tumor suppressor polypeptide. The following example details the ability of a p53 expressing adenovirus of the invention to treat human breast cancer.

Introduction of wild-type p53 into tumors with null or mutant p53 offers a novel strategy for controlling tumor growth. Casey (1991) *Oncogene* 6: 1791–1797, introduced wild-type p53 into breast cancer cells in vitro via a plasmid DNA vector. The number of MDA-MB-468 (p53$^{mut}$) and T47D (p:53$^{mut}$) colonies arising after plasmid transfection was reduced 50% by wild-type p53. Also, none of the resultant colonies expressed the wild-type p53 transfectant. By contrast, the number of MCF-7 (p53 wt) colonies was not affected. Negrini (1994) *Cancer Res.* 54: 1818–1824, conducted a similar study using MDA-MB-231 cells. Colony formation was reduced 50% by transfection with a plasmid containing wild-type p53 and none of resultant colonies expressed wild-type p53. Paradoxically, in this study similar results were observed with MCF-7 cells.

In the study described in this example the efficacy of a replication-deficient, recombinant, E1 region-deleted, p53 adenovirus (p53 Ad; (A/C/N/53) Wills (1994) supra) was tested against three human breast cancer cell lines expressing mutant p53, MDA-MB-231, MDA-MB-468, and MDA-MB-435. The MDA-MB-231 cells carry an Arg-to-Lys mutation in codon 280 of the p53 gene (Bartek (1990) *Oncogene* 5: 893–899). The MDA-MB-468 cells carry an Arg-to-His mutation in codon 273 (Id.). The MDA-MB-435 cells carry a Gly-to-Glu mutation in codon 266 of the p53 gene (Lesoon-Wood (1995) *Hum. Gene Ther.* 6:395–405).

Previous studies have shown high levels of wild-type p53 expression in tumor cells from human breast, ovary, lung, colorectum, liver, brain, and bladder after infection with p53 Ad in vitro (Wills (1994) supra., Harris et al. (1996) *Cancer Gene Therapy* 3: 121–130). Adenovirus-mediated p53 expression ultimately resulted in changes in cell morphology and the induction of apoptosis in p53 null or mutant p53 tumor cells. Infection of 468 breast cancer cells by p53 Ad at 10 m.o.i. (multiplicity of infection) caused almost 100% inhibition of DNA synthesis by 72 hrs. after infection. In addition, infection with p53 Ad in vitro inhibited proliferation of MDA-MB-468 and MDA-MB-231 cells with ED$_{50}$ values of 3±2 and 12±10 m.o.i., respectively. Proliferation of three other p53-mutant breast carcinoma lines was also inhibited at low concentrations of p53 Ad. The ED$_{50}$ values were 16±4 m.o.i. for SK-BR-3 cells, 3±3 m.o.i. for T-47D cells, and 2±2 m.o.i. for BT-549 cells. Infection of MDA-MB-468 and MDA-MB-231 cells with 30 m.o.i. of an equivalent, recombinant adenovirus expressing *E. coli* beta-galactosidase (beta-gal), instead of p53, resulted in >67% beta-gal positive MDA-MB-468 cells and 34–66% beta-gal positive MDA-MB-231 cells. By correlating the percentage of beta-gal positive cells with the p53 anti-proliferative effects in a large panel of tumor cells with altered p53, Harris et al. (supra.) showed a strong positive correlation between the degree of p53-induced inhibition and the degree of adenovirus transduction. In contrast, cell lines expressing normal levels of wild-type p53 were minimally affected by p53 transduction, independent of the adenovirus transduction rate.

Proliferation of MCF7 and HBL-100 cells, two human mammary cell lines containing wild-type p53, was relatively unaffected by p53 Ad concentrations greater than or equal to 99 m.o.i. in vitro. In other words, growth inhibition of MCF-7 and HBL-100 cells required p53 Ad concentrations at least 8- and 33-fold higher than the ED$_{50}$ values for -231 and -468 cells, respectively. Using a similar recombinant p53 Ad, Katayose (1995) *Clin. Cancer Res.* 1:889–897, demonstrated increased p53 protein expression, decreased cell proliferation, and increased apoptotic cell death in -231 cells transduced in vitro. This study extends these in vitro results with -468 and -231 cells to breast cancer xenografts in vivo. The efficacy of adenovirus-mediated p53 gene therapy is evaluated in another breast cancer cell line (MDA-MB-435) which is resistant to adenovirus transduction in vitro.

Materials and Methods

Cell Lines and Adenovirus Infections in vitro

The human breast cancer cell lines MDA-MB-231, -468, and -435 were obtained from ATCC (Rockville, Md., USA). The -231 cells were cultured in DMEM (Life Technologies, Grand Island, N.Y.) with 10% fetal calf serum (FCS; Hyclone, Logan, Utah) at 37° C. and 5% $CO_2$. The -468 cells were cultured in Leibovitz's L-15 medium (Life Technologies) containing 10% FCS at 37° C. The -435 cells were cultured in Leibovitz's L-15 medium with 15% FCS and 10 μg/ml bovine insulin (Sigma Chem. Co., St. Louis, Mo.) at 37° C.

Construction and propagation of the human wild-type p53 expressing and *E. coli* beta-galactosidase (beta-gal) expressing recombinant adenoviruses (rAd), where transgene expression is directed by the human cytomegalovirus promoter, have been described previously (Wills (1994) supra). Adenoviruses were administered in phosphate buffer (20 mM $NaH_2PO_4$, pH 8.0, 130 mM NaCl, 2 mM $MgCl_2$, 2% sucrose). C.I.U. is defined as cellular infectious units. The concentration of infectious viral particles was determined by measuring viral hexon protein positive 293 cells after a 48 hr. infection period (Huyghe (1995) supra).

For in vitro infection studies with p53 Ad, cells were plated at a density of 1–5×10$^4$ cells/well in 12-well tissue culture dishes (Becton Dickinson, Lincoln Park, N.J., USA). Cells were transduced with 0, 10, or 50 m.o.i. (multiplicity of infection=C.I.U./cell) p53 Ad and cultured for 72 hrs. as previously described (Wills (1994) supra.). For in vitro infection studies with beta-gal Ad, cells were plated at a density of 1×10$^5$ cells/well. The cells were transduced with 0, 10, 50, or 100 m.o.i. beta-gal Ad. After 48 hours, the cells were fixed with 0.2% glutaraldehyde (Sigma Chemical Co.) then washed 3 times with PBS (Life Technologies). The cells were then assayed in 1 ml of X-Gal solution [1.3 mM MgCl$_2$, 15 mM NaCl, 44 mM Hepes buffer, pH 7.4, 3 mM potassium ferricyanide, and 1 mg/ml X-Gal in N,N-dimethylformamide (10% final conc.)]. X-Gal was purchased from Boehringer Mannheim Corp., Indianapolis, Ind. All other chemicals were purchased from Sigma.

To determine the percentage of transduced cells, 5 microscope fields were counted from each culture well and the average percent expressing beta-galactosidase was calculated for 3 wells at each m.o.i.

Adenovirus Treatment in vivo

Athymic female nude mice were purchased from Charles River Laboratories (Wilmington, Mass., USA). All mice were maintained in a VAF-barrier facility and all animal procedures were performed in accordance with the rules set forth in the N.I.H. Guide for the Care and Use of Laboratory Animals. Tumor cells were injected subcutaneously or into the mammary fat pad.

Cell inoculations were: 5×10$^6$-231 cells/mouse, 1×10$^7$ MDA-MB-468 cells/mouse, or 1×10$^7$ MDA-MB-435 cells/mouse. Tumors were allowed to grow in vivo for 10–11 days before the start of dosing, except for one -468 experiment where the tumors grew for 33 days before treatment started. Tumor volume was calculated as the product of measurements in three dimensions. Tumor volumes for different treatment groups on each day were compared by Student's t test using Statview II software (Abacus Concepts, Berkeley, Calif.). Average percent inhibitions for groups dosed on days 0–4 and 7–11 were calculated using significant values (p<0.05) from day 14 to the end of the study.

The specific effects of p53 were distinguished from adenovirus vector effects by subtracting the average tumor growth inhibition caused by beta-gal Ad from growth inhibition caused by p53 Ad. All virus injections were peri/intratumoral. In general, two 5-day courses of tumor therapy (i.e., 5 injections) were given to each mouse, separated by a 2 day "resting period". In some cases, this dosing regime was extended for more than 2 weeks and/or buffer vehicle was substituted for virus for some injections. Tumor growth curves show mean tumor volume±s.e.m.

Histology and Apoptag Immunohistochemistry

Tissue samples were fixed in 10% buffered formalin and processed overnight in a Miles VIP Tissue Processor, then imbedded in paraffin. Five micron tissue sections were cut with a Leitz microtome. The slides were stained with a routine Harris hematoxylin and eosin stain (Luna et al. (1968), *Manual of Histologic Staining Methods of the Armed Forces Institute of Pathology*. New York: McGraw Hill Book Co.).

Apoptag in situ apoptosis detection kits were purchased from Oncor (Gaithersburg, Md., USA). Samples were assayed as per kit directions. Briefly, deparaffinized, rehydrated tissue sections were treated with Oncor Protein Digesting Enzyme, incubated with TdT, and developed using an avidin-peroxidase kit (rabbit IgG-Sigma Chem. Co. #EXTRA-3) and DAB (Vector Lab. #SK4100). Slides were counterstained with methyl green.

Beta-galactosidase Assay

Tumors were embedded in TBS (Triangle Biomedical Sciences, Durham, N.C., USA) and flash frozen in a 2-methylbutane/dry ice bath. Frozen tissue sections (8 μm thick) were fixed in 0.5% glutaraldehyde at 4° C. for 5 min. and then assayed for beta-gal expression as described above.

Integrin FACS Analysis

Cells were suspended by treatment with 0.02% EDTA, pelleted, and then washed 2× with PBS. Cells were then resuspended at a concentration of 1×10$^6$ cells/ml and incubated with primary antibodies (final conc. 1:250/ml) at 4° C. for 1 hr. Cell suspensions were washed 2× with PBS to remove excess primary antibody. Cells were then incubated with FITC-conjugated rabbit antimouse adjunctive antibody (final conc. 1:250/ml, Zymed) at 4° C. for 1 h. Cells were washed as before with PBS and immediately analyzed. Fluorescence was measured with a FACS Vantage flow cytometer (Becton Dickinson, Mountain View, Calif., USA). Side scatter and forward scatter were determined simultaneously, and all data were collected with a Hewlett Packard computer equipped with FACS research software (Becton Dickenson). Primary antibodies used to detect integrin receptors were obtained from the following suppliers: anti-alpha$_v$, (12084-018, Gibco BRL); anti-beta$_3$ (550036, Becton Dickenson); anti-alpha$_v$beta$_3$ (MAP1976, Chemicon); anti-beta$_1$, (550034, Becton Dickenson); and anti-alpha$_v$beta$_5$ (MAB 1961, Chemicon).

Results

Adenovirus Transduction Efficiency and p53 Growth Inhibition in vitro

The -231 and -468 cells were both highly transduced in vitro at an m.o.i. of 10. By contrast, -435 cells were rarely transduced, even at 100 m.o.i. For -231 cells, 8% (10 m.o.i.), 46% (50 m.o.i.), and 62% (100 m.o.i.) of the cells were transduced by beta-gal Ad. For 468 cells, 78% (10 m.o.i.), 84% (50 m.o.i.), and 97% (100 m.o.i.) of the cells were transduced by beta-gal Ad. For 435 cells, 0.5% (10 m.o.i.), 1% (50 m.o.i.), and 1.3% (100 m.o.i.) of the cells were transduced by beta-gal Ad.

Figure 3A:
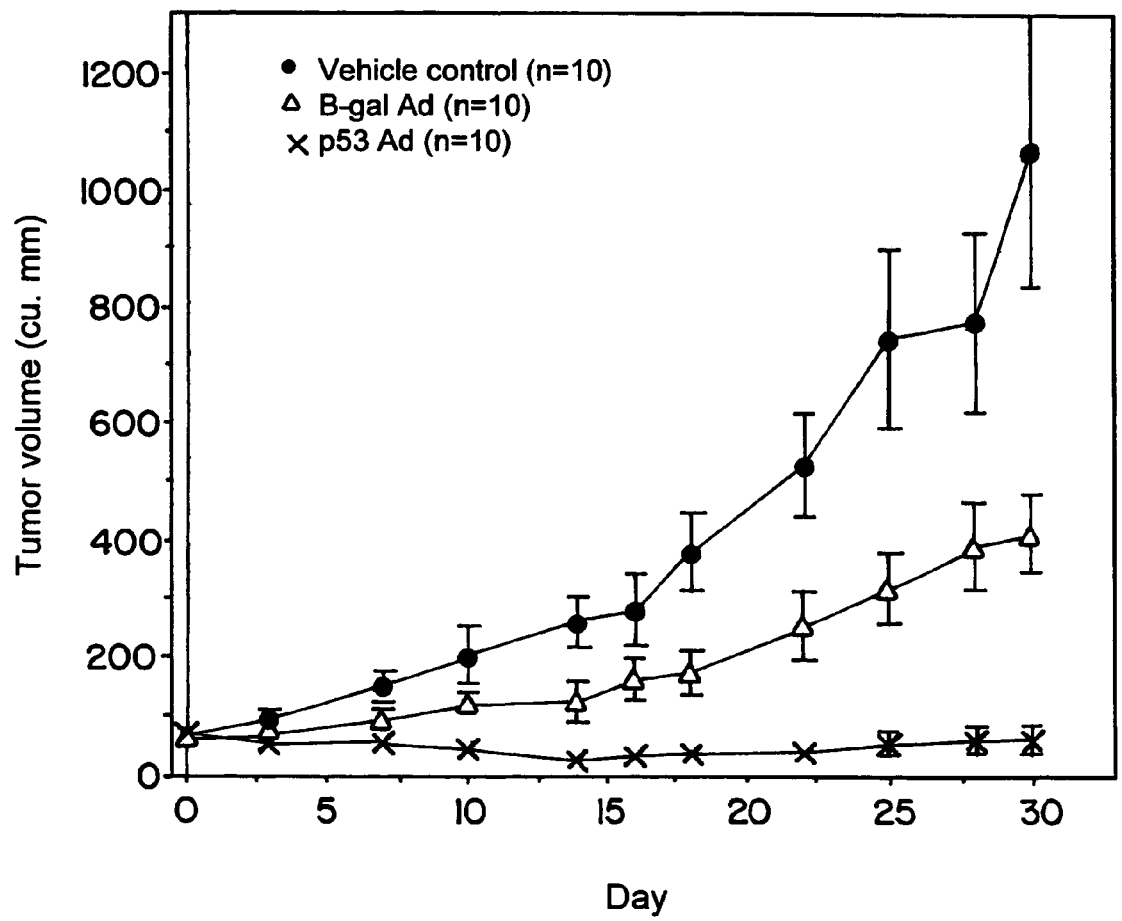
FIGS. 3a, 3b, and 3c illustrate the efficacy of p53 Ad against human breast cancer xenografts in nude mice. Mice were given a total dose of $2.2 \times 10^9$ C.I.U. adenovirus (A/C/N/53 or Ad) per mouse split into 10 injections on days 0–4 and 7–11. Mice were treated with p53 Ad, beta-gal Ad, or vehicle alone.
Figure 3B:
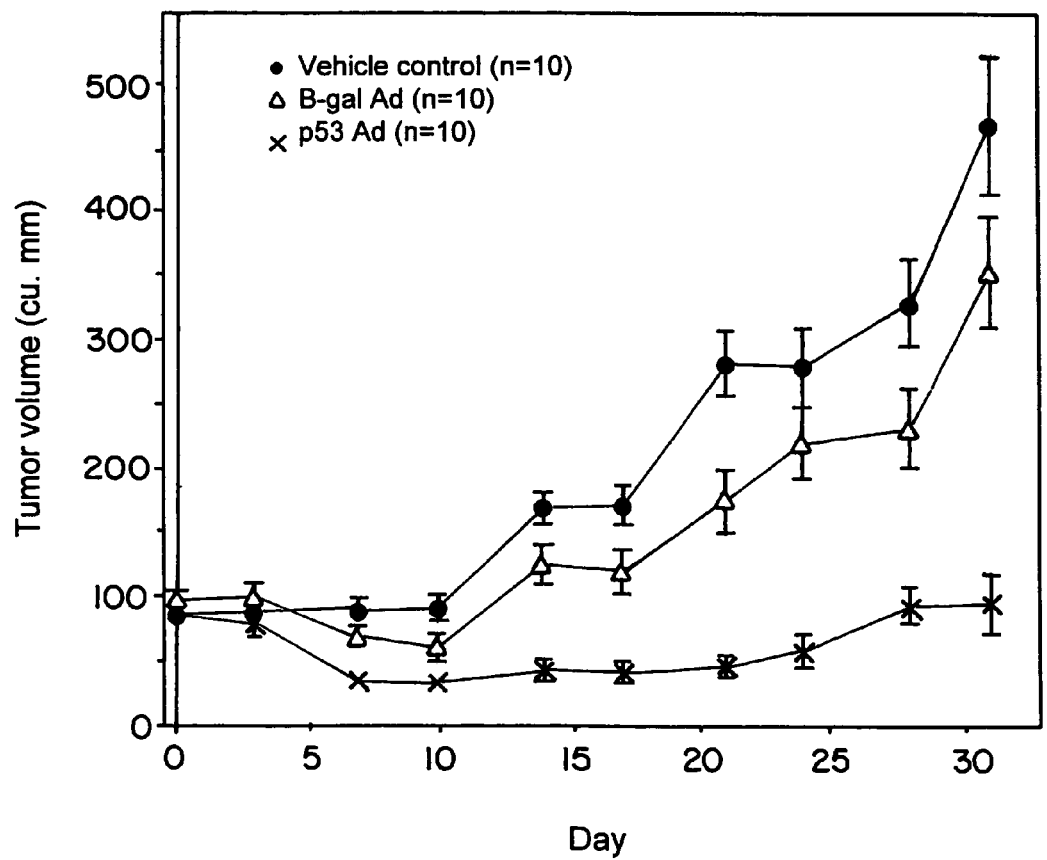
Figure 3C:
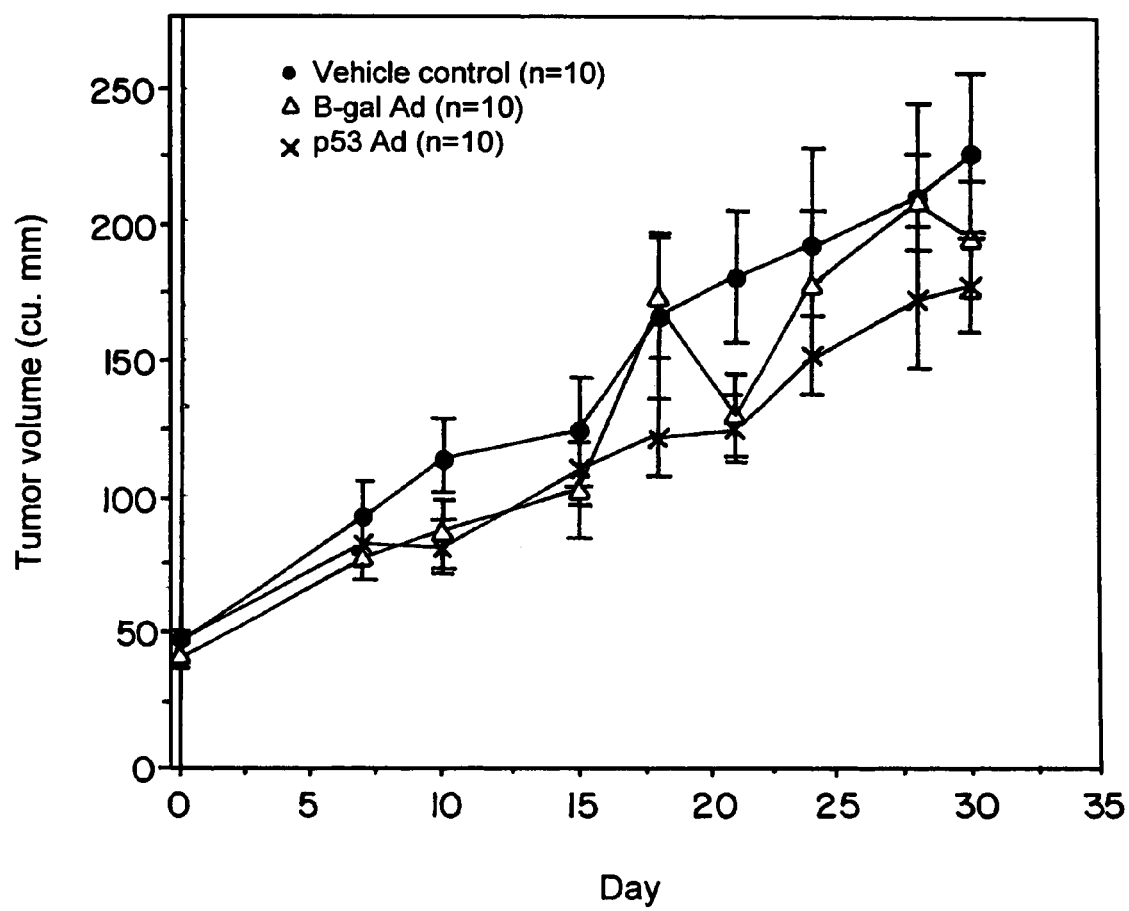
Figure 4A:
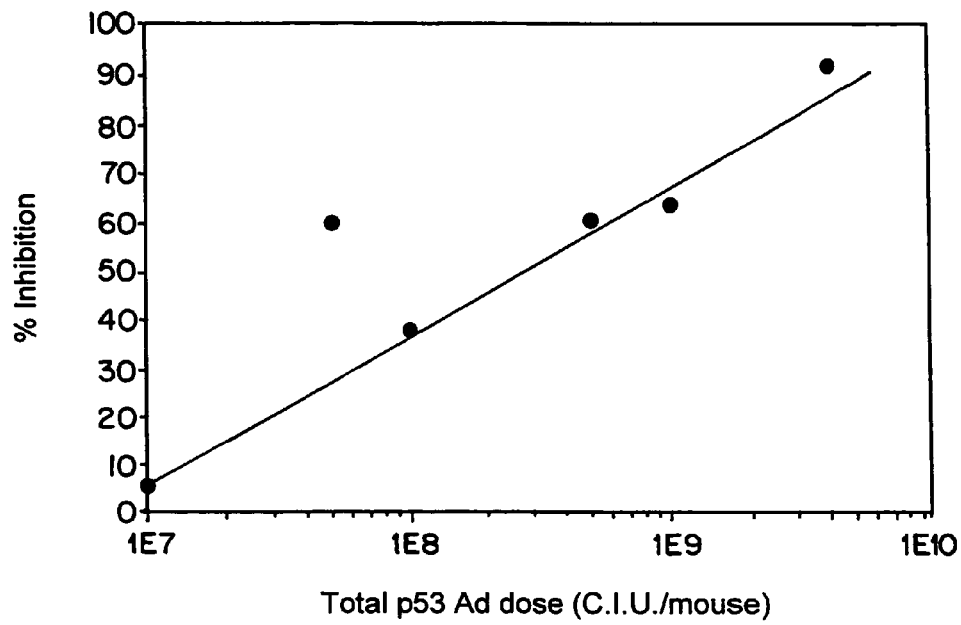
FIGS. 4a and 4b provide p53 Ad(A/C/N/53) dose response curves for MDA-MB-231 (-231) tumors (FIG. 4a) and for MDA-MB468 tumors (FIG. 4b). Mice were dosed with $1 \times 10^7 – 1 \times 10^9$ C.I.U. p53 Ad (A/C/N/53) split into 10 doses administered peritumorally on days 0–4 and 7–11. Average percent inhibitions were calculated by comparing the tumor volumes at each p53 Ad dose with buffer-treated tumors on the days 14/15, 18, 21, 24, 28, 30/32, and 35 (MDA-MB-468 tumors only on day 35). The -231 tumors averaged $22.5 \pm 1.2$ mm$^3$ on day 0, while the -468 tumors averaged $33.1 \pm 1.8$ mm$^3$ on day 0.
Figure 4B:
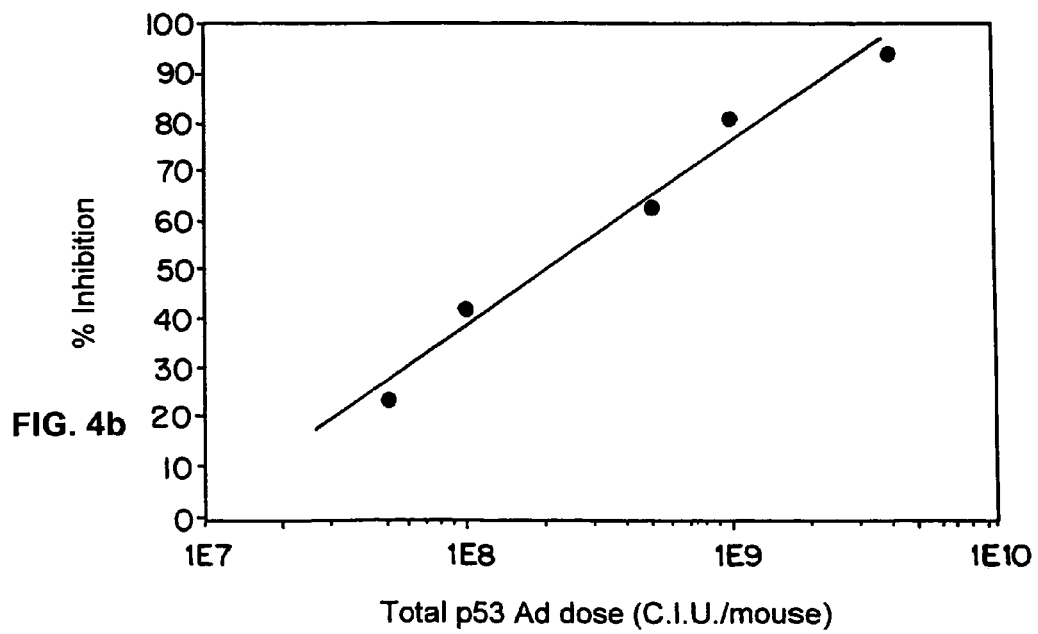
Figure 5:
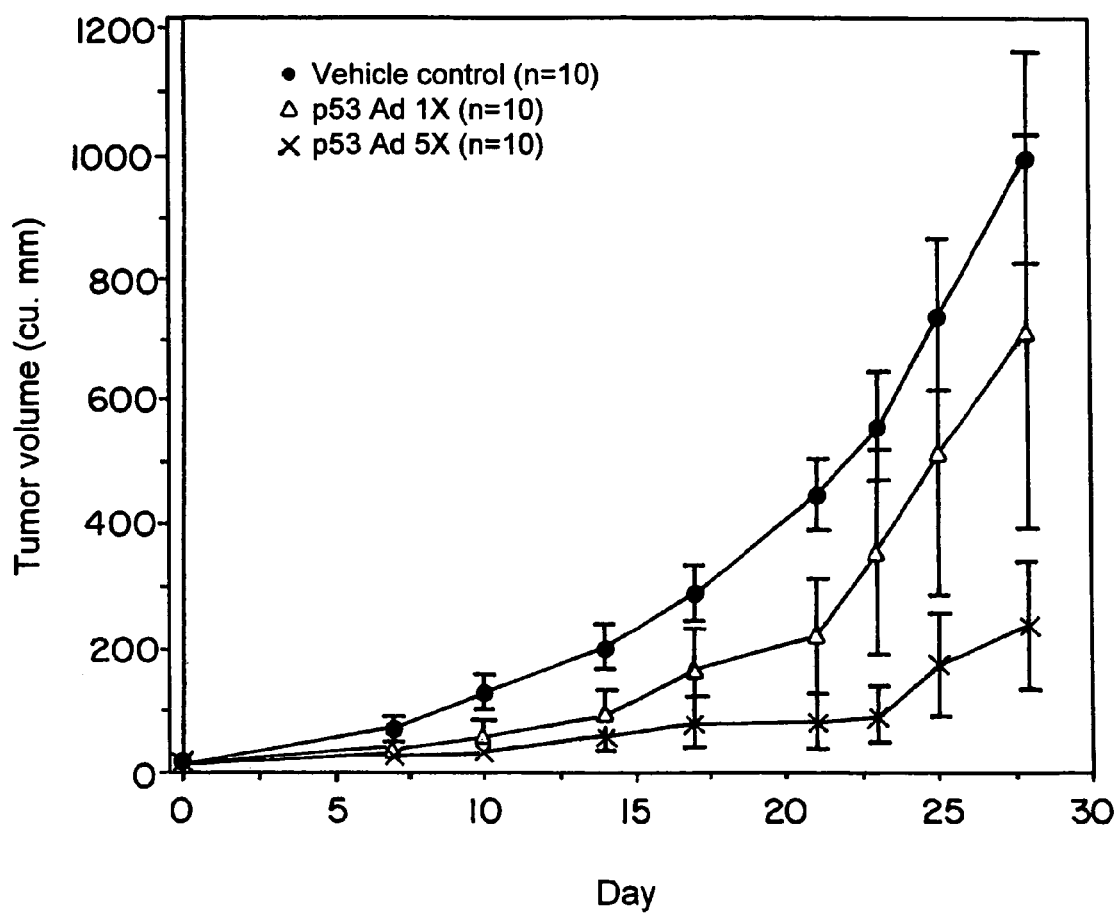
FIG. 5 provides a comparison of the efficacy of the therapeutic agent when administered as a single bolus or as split doses. Tumors (MDA-MB-231) were dosed with a total of $2.2 \times 10^8$ C.I.U. p53 Ad per week given during weeks 1 and 3.

Infection with 50 m.o.i. p53 Ad resulted in nearly complete cell death in the 231 and 468 cell cultures. By contrast, p53 Ad had no detectable effect on the growth of 435 cells.

p53 Ad Efficacy Against Human Breast Cancer Xenografts Adenovirus-mediated p53 gene therapy was highly effective against -231 and -468 xenografts (FIGS. 3a & 3b). In the 231 experiment, 1 mouse in the beta-gal Ad group and 3 mice in the p53 Ad group were tumor-free at the end of the study, and all tumors regressed during p53 Ad treatment. Inhibition of -231 tumor growth averaged 86% (p≦0.01). The component of growth inhibition due to p53 averaged 37%, while adenovirus-specific inhibition averaged 49% (p≦0.01). Inhibition of -468 tumor growth averaged 74% (p≦0.001). One mouse in the p53 Ad group was tumor-free at the end of the study and all tumors regressed during p53 Ad treatment. The component of growth inhibition due to p53 averaged 45% (p<0.001), while adenovirus-specific inhibition averaged 28% (p≦0.05). No side-effects were observed in either experiment. The ED$_{50}$ values for -231 and -468 tumor growth inhibition were 3×10$^8$ C.I.U. (cell infectious units) and 2×10$^8$ C.I.U., respectively (FIG. 4). The -435 tumors were almost completely resistant to p53 Ad treatment (FIG. 3c). Growth inhibition in the 435 tumor groups treated with adenovirus was not significant, FIG. 5 shows a comparison of the efficacy of two p53 Ad dosing regimes against -231 tumors. All mice were given 5 peritumoral injections per week. All mice treated with the therapeutic agent (p53 Ad) received a total of $2.2 \times 10^9$ C.I.U./mouse per week. One group received a single bolus injection containing the entire week's dose of adenovirus. The other 4 injections for the week consisted of buffer vehicle (1× group). The other treated group received the same Ad dose split into five injections per week (5× group). This dosing regime was given during weeks 1 and 3 (days 0–4, 14–18). Growth inhibition averaged 73% for the 5× group (p-<O.01), but only 44% for the 1× group (p<0.05 for the first three weeks of the study, not significant after day 21). The first cycle of p53 gene therapy was more effective than the second cycle. After the first therapy cycle, 4 mice in the 1× group, 5 mice in the 5× group, and 1 mouse in the vehicle control group were tumor-free. One mouse in the 5× group relapsed with a very small tumor by day 21. No further "cures" were observed after the second cycle of therapy.

Figure 6:
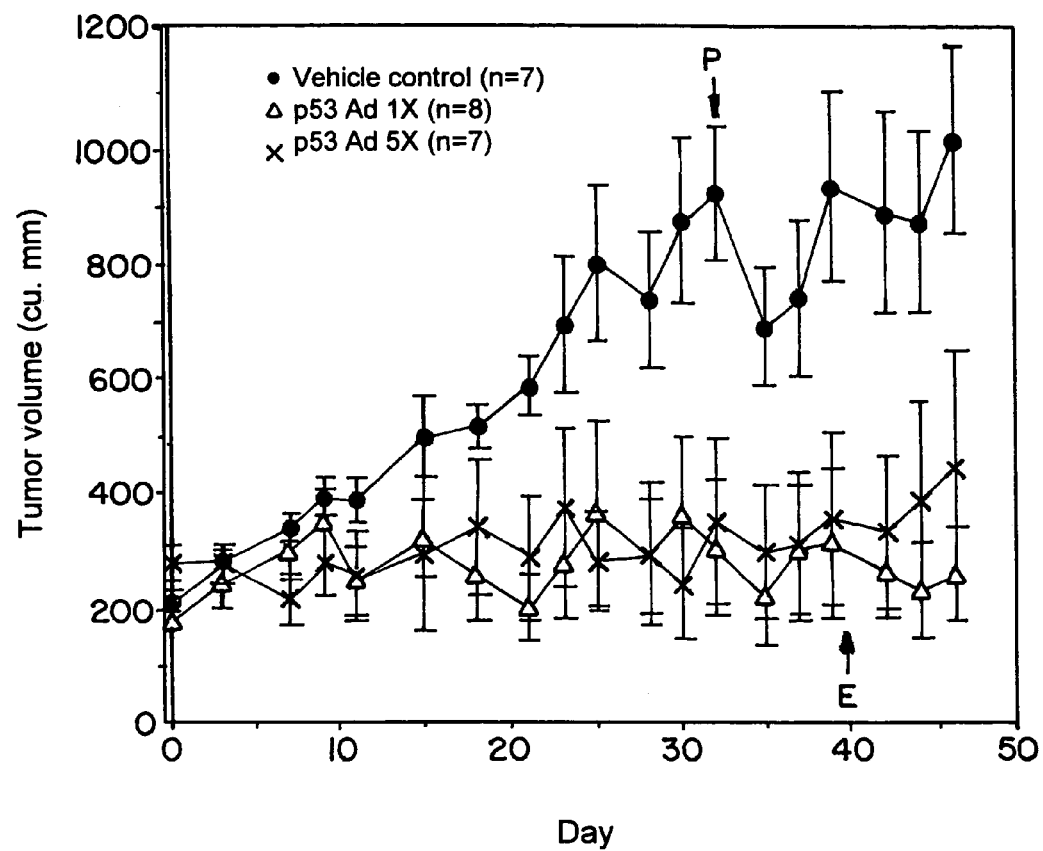
FIG. 6 illustrates the efficacy of multiple cycles of low dose p53 Ad against large, well-established tumors. A total dose of $1.32 \times 10^9$ C.I.U. p53 Ad was given over 6 weeks to MDA-MB-468 xenografts. (P=plateau in control tumor growth rate; E=end of dosing.).

FIG. 6 shows an experiment using 468 tumors that were initially 4-fold larger than the 468 tumors shown in FIG. 3*b*, treated with a 10-fold lower dose of adenovirus. A total dose of $2.2 \times 10^8$ C.I.U. p53 Ad/mouse per week was administered. One group received a single bolus injection of virus, followed by 4 injections of buffer per week (Ix group). The other treated group received the same viral dose split into five injections per week (5× group). These dosing schedules were given for 6 weeks. The total viral dose administered over 6 weeks was approximately half the dose used in FIG. 3. This dosing regime resulted in a cytostatic effect on tumor volume in mice treated with p53 Ad ($p \leq 0.05$). Treatments given early in the study appeared to be more effective than those given during later weeks. One mouse in the 5× group was tumor-free by day 21. However when tumor growth inhibition in all mice was compared, the Ix dosing regime (60%) was slightly, but not significantly, more effective than the 5× regime (55%). By 1 week after the end of dosing, the tumor growth rate in the 5× group started to increase. One month after the start of the study, the vehicle control tumors started to necrose and growth plateaued.

In vivo Infectivity After Repeated Adenovirus Exposure

At the end of the studies shown in FIGS. 5 and 6, some tumors were injected with beta-gal Ad. These tumors were harvested 24 hrs. later and frozen tissue sections were assayed for beta-galactosidase expression. Tumors treated with p53 Ad for 2 or 6 weeks were still transduced by beta-gal Ad, although transduction was lowest in the -468 tumors treated for 6 weeks with p53 Ad 5× per week. Sections from only 1 of the 3-468 tumors injected in the 5× group had cells expressing beta-galactosidase.

Induction of Apoptosis in vivo by p53 Ad

The MDA-MB-231 and MDA-MB-468 breast cancer xenografts in nude mice were injected with $1-5 \times 10^8$ C.I.U. p53Ad or buffer 48 to 72 hrs. before harvest. The induction of apoptosis by p53 Ad was assayed using Apoptag immunohistochemistry on tissue sections. Tumors injected with p53 Ad had areas of extensive apoptosis along the needle track(s) of tumors injected intra-tumorally and around the outside border of tumors injected peritumorally. By contrast, tumors injected with buffer had only a few scattered apoptotic cells, as expected.

Comparison of Integrin Expression in MDA-MB-231 and MDA-MB-435 Cells

FACS analysis of integrin expression was performed on MDA-MB-231 and MDA-MB-435 cells to determine whether the low Ad transduction of MDA-MB-435 cells was due to a deficiency in the alpha, integrins needed for internalization of Ad types 2, 3, and 4 (Wickham et al. (1993) *Cell*, 73: 309–319; Wickham et al. (1994) *J. Cell Biol.*, 127: 257–264; and Mathias et al. (1994) *J. Virol.* 68: 6811–6814). Both cell types expressed alpha$_v$, alpha$_v$beta$_3$, alpha$_v$beta$_5$, and beta$_1$ integrin moieties at approximately the same levels. Integrin alpha$_v$beta$_3$ and beta$_3$ expression were higher on MDA-MB-435 cells than on MDA-MB-231 cells.

Discussion: When a total dose of $2.2 \times 10^9$ C.I.U. p53 Ad was administered in 10 injections, tumor growth inhibition was 74% for MDA-MB-468 tumors and 86% for MDA-MB-231 tumors, but was not significant for MDA-MB-435 tumors. In MDA-MB-468 tumors, 61% of the total response was p53-specific, while in MDA-MB-231 tumors, 43% of the total response was p53-specific. The ability of beta-gal Ad to transduce MDA-MB-231, MDA-MB-468, and MDA-MB-435 cells in vitro was generally predictive of the in vivo results. At the same virus concentrations, -468 cells had a slightly higher transduction rate than MDA-MB-231 cells, while MDA-MB-435 cells were resistant to adenovirus transduction. The MDA-MB-435 results in vitro correlated with the very poor response in vivo.

Systemic treatment of nude mice bearing MDA-MB-435 tumors, with a p53-liposome vector, has been shown to cause tumor growth inhibition, and in some cases, recession (Lesoon-Wood et al. (1995) *Hum. Gene Ther.*, 6: 395–405). P53-liposome treatment also reduced the number of lung metastases. These results demonstrate that the lack of MDA-MB-435 tumor response to p53 Ad treatment in this study was not due to an inability of p53 to inhibit growth and metastasis of MDA-MB-435 tumors. Rather, these results suggest it was the low adenovirus transduction efficiency of MDA-MB-435 cells that caused their nonresponsiveness to p53 Ad treatment.

The alpha, integrins have been implicated as cellular elements required for efficient internalization of type 2, 3, and 4 adenoviruses (Wickham (1993) supra.; Wickham (1994) supra.; and Mathias (1994) supra.). It is likely that alpha$_v$ integrins perform the same role for type 5 Ad. Wickham et al. (1994) supra., observed 5–10-fold higher internalization of a recombinant type 5 adenovirus in cells transfected with alpha$_v$beta$_5$ as compared to cells lacking alpha$_v$ expression or transfected with alpha$_v$beta$_3$. The human embryonic kidney -293 cells used for production of the p53 Ad used herein express alpha$_v$beta$_1$, but not alpha$_v$beta$_3$ integrins (Bodary (1990) *J. Biol. Chem.* 265: 5938–5941). Therefore, it seemed prudent to measure -435 cell expression of the alpha, beta$_1$, beta$_3$, and alpha$_5$ integrin subunits. Both MDA-MB-231 and MDA-MB-435 cells expressed roughly equivalent levels of the integrin family molecules. Therefore, the lack of Ad transduction of MDA-MB-435 cells is not due to a deficiency in alphas integrin expression. Currently, no literature exists on the identity of the cellular receptor required for Ad binding to target cells. It is possible that the MDA-MB-435 cells are deficient in this receptor or that some other component required for viral binding, internalization, or gene expression is defective.

The continued efficacy of p53 Ad over multiple cycles of therapy was examined in the MDA-MB-231 and MDA-MB-468 tumor models. It appears that efficacy decreased with continued dosing, however this effect needs to be examined in more detail. Prevailing theory holds that adenovirus infection generates a rapid inflammatory and cytolytic response mediated by cytotoxic T cells in hosts with fully functional immune systems (reviewed by Wilson (1995) *Nature Med.* 4: 887–889). This T cell response is stimulated by adenovirus antigens produced in host cells and presented in conjunction with MHC moieties on the cell surface. Neutralizing antibodies specific for cells transduced by adenovirus are produced later in the immune response and are believed responsible for the reduced ability to reinfect host cells with adenovirus after the initial inoculations. The athymic nude mice used in these studies have a defective T cell immune response to foreign antigens, but are able to generate a B cell-mediated antibody response (Boven (1991) *The Nude Mouse in Oncology Research.* Boston: CRC Press). The production of neutralizing anti-adenovirus antibodies could explain the reduced efficacy of p53 adenovirus (p53 Ad) therapy over time in the present studies. The impaired immune function in nude mice and the poor blood supply to the interiors of the tumor xenografts could explain the partial effectiveness of the p53 Ad even after 6 weeks of dosing and the ability to infect a few tumor cells with beta-gal Ad even after repeated p53 Ad injections.

In addition to breast cancer, a number of other cancers have been treated with recombinant adenoviruses expressing wild-type p53. These reports include models of cervical cancer (Hamada (1996) *Cancer Res.* 56: 3047–3054), prostate cancer (Eastham (1995) *Cancer Res.* 55: 5151–5155), head and neck cancer (Clayman (1995) *Cancer Res.* 55: 1–6), lung cancer (Wills (1994) supra.), ovarian cancer (13), glioblastoma (27, 28), and colorectal cancer (13, 29). Collectively, these data support ongoing clinical investigations evaluating the effects of adenovirus-mediated p53 gene therapy. The present results demonstrate the ability of wild-type p53 to curtail cancerous cell growth in vivo in breast cancer xenografts expressing mutant p53. The present studies also confirm that adenovirus appears to be an efficient delivery vehicle for the 53 when target cells express the appropriate viral "receptor(s)".

Example 4

Further Investigations of Treatment Regimen on Tumor Inhibition

The invention provides for the treatment of various cancers by the administration of nucleic acid expressing a tumor suppressor polypeptide using various dosage regimens. The following example details the increased efficacy of split dosing the administration of p53 expressing adenovirus of the invention.

In order to investigate the effect of a single dosage regimen as compared to split doses administered over a period of time, scid mice injected with MDA-MB-468 and MDA-MB-231 tumors were treated with a total dose per mouse of $1 \times 10^9$ I.U. p53 Ad (A/C/N/53) administered as a single bolus injection or split into 3 or 5 injections administered once a day over the course of a week (indicated by arrows in FIG. 7).

Figure 7A:
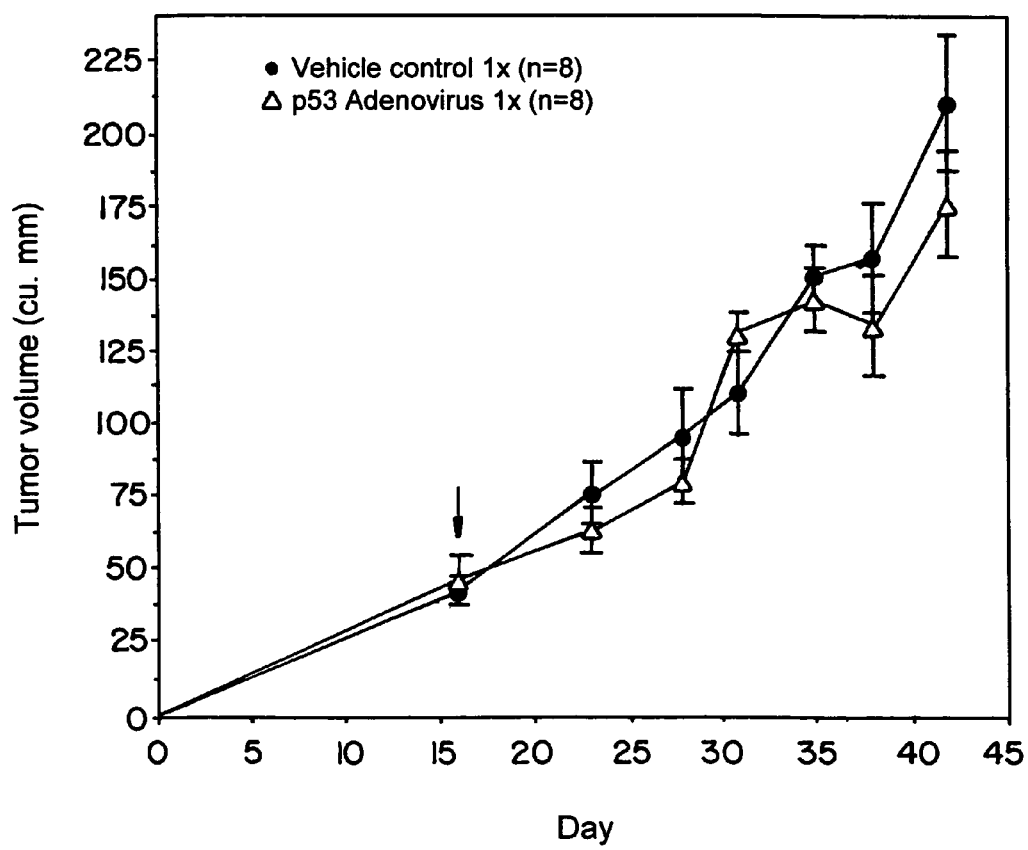
FIGS. 7a, 7b, and 7c illustrate-the in vivo inhibition of MDA-MB-468 tumors in nude mice administered $1 \times 10^9$ C.I.U. p53 Ad (A/C/N/53) as a single bolus injection (FIG. 7a) or split into 3 injections (FIG. 7b) or 5 injections (FIG. 7c).
Figure 7B:
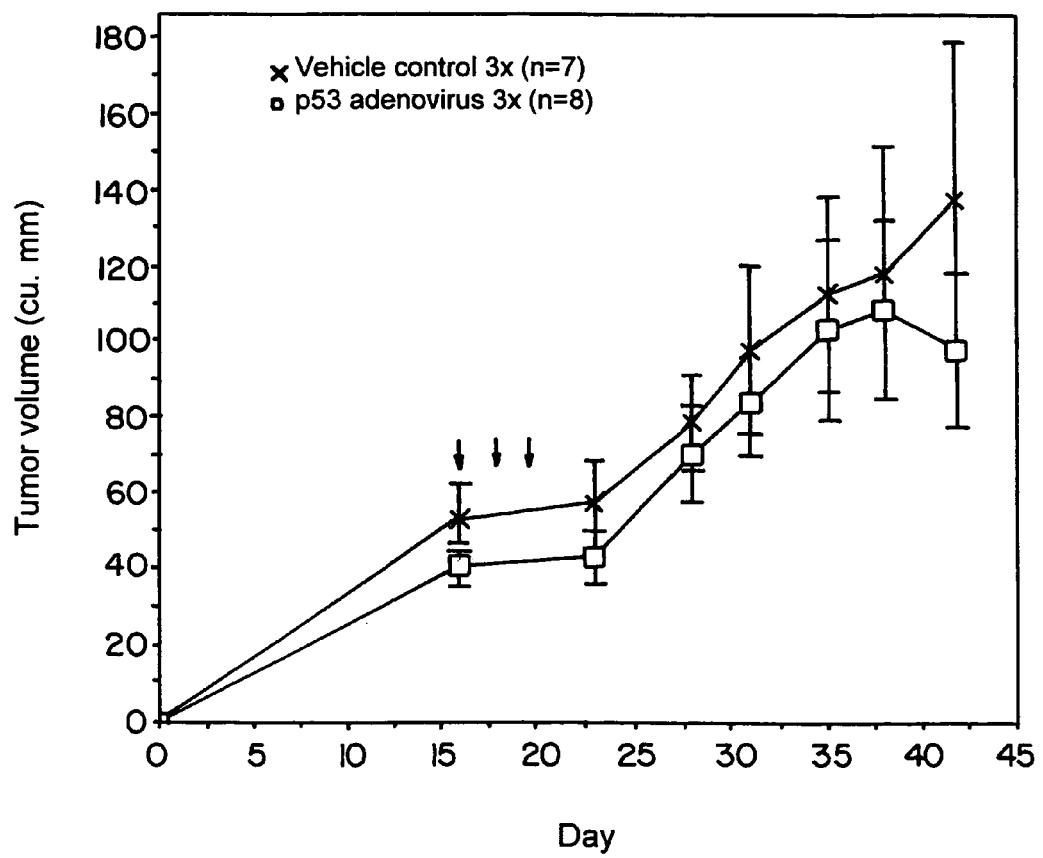
Figure 7C:
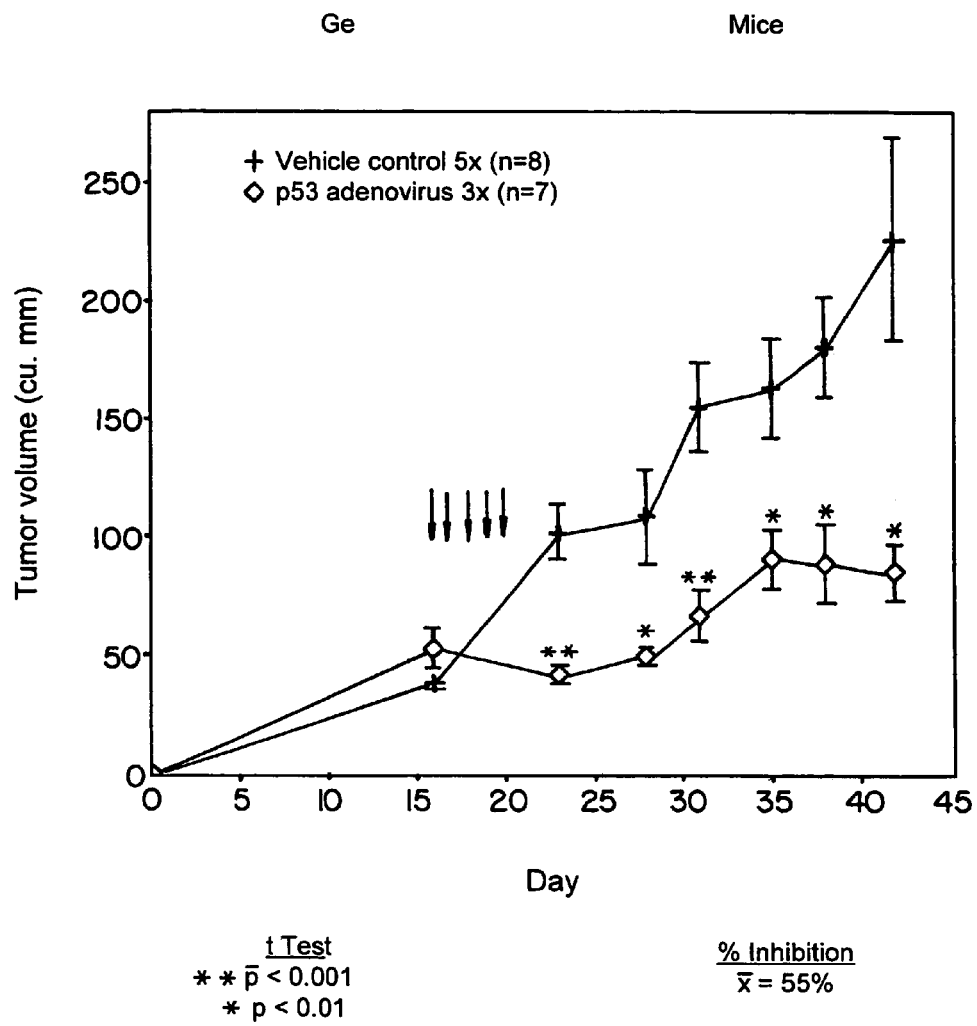

The results obtained with MDA-MB-468 tumors were similar to those obtained with MDA-MB-23 tumors and are illustrated in FIGS. 7a, 7b, and 7c. In general, split dosing inhibited tumor growth better than single bolus injections with the 5 injection dosage regimen having significant improvement over the 3 injection dosage regimen.

Example 5

Dexamethasone Mutes the Inhibition of Tumor Growth Associated with NK Cell-Mediated Anti-Adenovirus Immune Response It has been demonstrated that repeated administration of adenovirus vectors can induce an anti-adenovirus immune response. To investigate whether the immunosuppressant properties of low dose Dexamethasone (Dex) can inhibit the anti-adenovirus immune response (e.g., NK cell response) MDA-MB-231 tumors in scid mice were treated with recombinant virus of the invention in the absence and in the presence of dexamethasone.

Approximately $5 \times 10^6$ MDA-MB-231 cells/mouse were injected into the mammary fat pads of female scid mice on day 0. On day 11, dexamethasone or placebo pellets were implanted subcutaneously. The 5 mg pellets were designed to release 83.3 μg dexamethasone/day continuously for 60 days (Innovative Research of America, Sarasota, Fla.). All mice received a total of 10 peritumoral injections given once a day on days 14–18 and 21–25 (0.1 ml per injection). The total virus dose was $2 \times 10^9$ C.I.U./mouse (p53 AD (A/C/N/53 or beta-galactosidase Ad). Treatments were as listed in Table 5.

TABLE 5

Treatment of MDA-MB-231 tumors in scid mice.

| Group | Hormone | Gene Therapy |
|---|---|---|
| 1 | placebo | buffer |
| 2 | placebo | beta-gal Ad |
| 3 | placebo | p53 Ad |
| 4 | dexamethasone | buffer |
| 5 | dexamethasone | beta-gal Ad |
| 6 | dexamethasone | p53 Ad |

Figure 8:
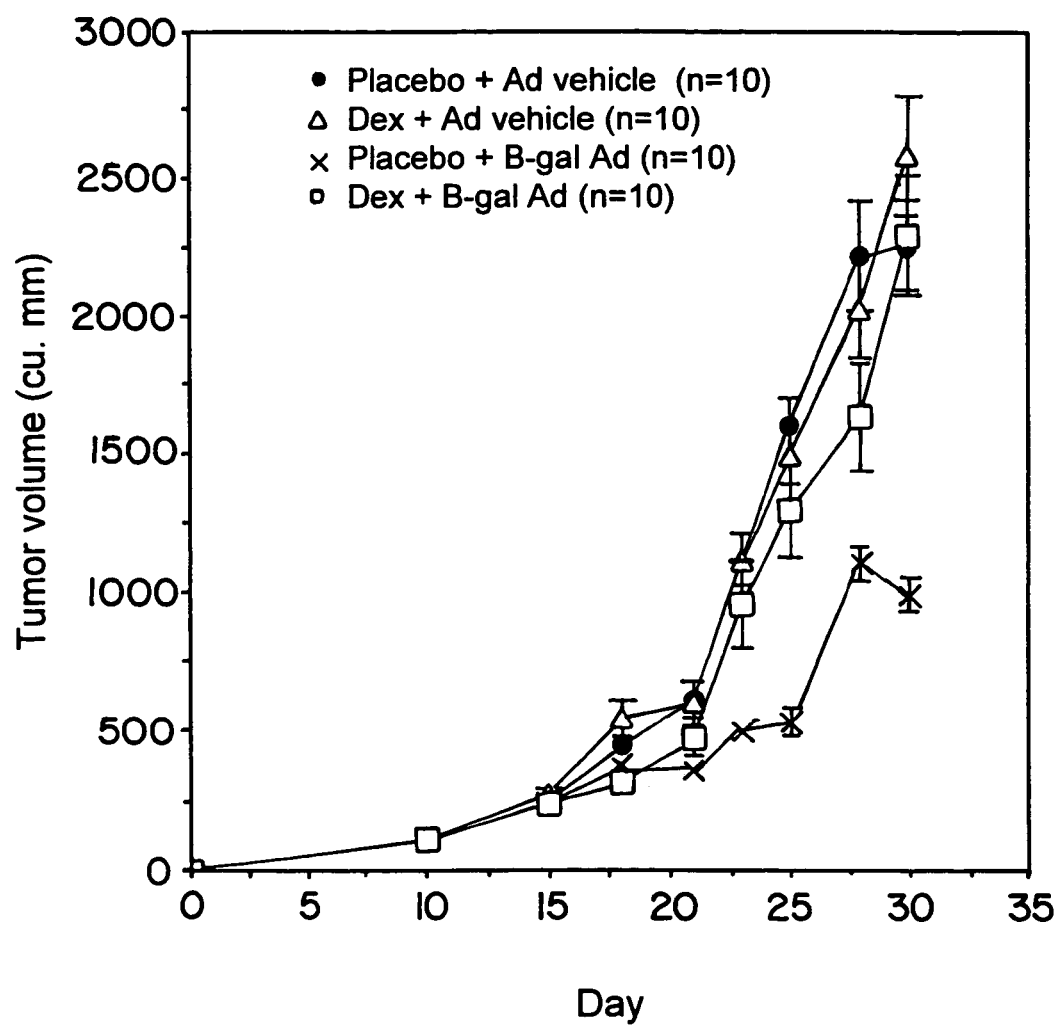
FIG. 8 illustrates of the ability of low dose dexamethasone to suppress the inhibition of tumor growth mediated by NK cells in scid mice. MDA-MB-231 tumors were dosed with a total of $2\times10^9$ C.I.U. beta-gal Ad ($1.1\times1011$ viral particles) split into 10 injections given on days 14–18 and 21–25. Subcutaneous dexamethasone (or placebo) pellets released 83.3 μg steroid per day.

Low dosage dexamethasone treatment had no significant effect on the growth rate of MDA-MB-231 tumors in scid mice (p>0.05). No adverse side effects of dexamethasone were observed. Treatment of tumors with beta-galactosidase adenovirus caused significant inhibition of tumor growth in placebo control tumors (p≦0.001, days 21–30), but not in dexamethasone treated tumors (P>0.05, see FIG. 8). Tumors treated with placebo and beta-gal Ad grew slower than tumors treated with placebo and dexamethasone (p≦0.01, days 23–30).

There was no significant p53-specific inhibition of tumor growth in placebo control tumors (p>0.05). By contrast, tumors treated with dexamethasone and p53 Ad did grow significantly slower than tumors treated with dexamethasone and beta-gal Ad (P≦0.02, days 21–30) or placebo and p53 Ad (p≦0.04, days 21–30).

Low dose dexamethasone treatment thus muted the inhibition of tumor growth associated with the anti-adenovirus immune response (e.g., NK cell response) in scid mice without adverse side-effects. The data also suggest that low dose dexamethasone treatment may stimulate transgene (e.g., p53) expression driven by the CMV promoter in recombinant adenoviruses. Conversely, dexamethasone may increase adenovirus transduction efficiency and thereby increase tumor cell death.

The MDA-MB-231 breast cancer model was next used to evaluate the anti-tumor efficacy of Ad with and without p53 in mice with differing abilities to mount an immune response to foreign antigens. Nude mice with non-functional T cells, scid mice with nonfunctional T and B cells but elevated NK cells, and scid-beige mice with nonfunctional T, B, and NK cells were studied.

To study the efficacy of rAd5/p53 (described supra) against MDA-MD-231 xenografts: nude mice were given a total dose of $2.2 \times 10^9$ C.I.U. Ad per mouse split into 10 injections on days 0 to 4 and 7 to 11. SCID mice were given a total virus dose=4×10$^9$ C.I.U. split into 10 doses given on days 0–4 and 7–11. SCID-Beige mice were given a total virus dose=1.6×10$^9$ C.I.U. split into 10 doses given on days 0–4 and 7–11. All mice were treated with p53 Ad, beta-gal Ad, or vehicle alone.

In nude mice (non-functional T cells) or scid mice (non-functional T and B cells; elevated NK cells), intratumoral dosing with control Ad vector (no p53 insert) caused some inhibition of tumor growth. Ad expressing p53 (rAd5/p53) had greatly enhanced anti-tumor efficacy compared to control Ad. By contrast, in scid-beige mice (nonfunctional T, B, and NK cells), anti-tumor efficacy was all due to p53 expression with no Ad vector component to the tumor growth inhibition. These data demonstrate a previously unrecognized role for NK cells in Ad-mediated tumor growth inhibition. The data also suggest that suppression of the immune system might abrogate some vector-specific, NK cell mediated, side effects.

Example 6

Combination p53 Adenovirus and Chemotherapy Treatment

The invention provides for the combined administration of nucleic acid expressing a tumor suppressor polypeptide and chemotherapeutic agents in the treatment of neoplasms. The following example details the ability of a p53 expressing adenovirus of the invention in combination with various anti-cancer drugs, cisplatin, doxorubicin, 5-fluorouracil (5-FU), methotrexate, and etoposide, to treat neoplasms, and that the combination therapy was more effective, i.e., was synergistic, at killing tumor cells than either agent alone.

p53 Administered with Chemotherapeutic Drugs In Vitro

Cisplatin, Doxorubicin, 5-fluorouracil (5-FU), Methotrexate, and Etoposide, in Combination With p53

The effect of the clinically-relevant anti-cancer drugs cisplatin, doxorubicin, 5-fluorouracil (5-FU), methotrexate, and etoposide, in combination with a tumor suppressor vector of the invention (A/C/N/53), was investigated in vitro. SCC-9 head and neck squamous cell carcinoma, SCC-15 head and neck squamous cell carcinoma, SCC-25 head and neck squamous cell carcinoma, and DU-145 prostate carcinoma cells were subjected to one of three treatment regines: In treatment 1, the cells were pretreated with the anti-cancer chemotherapeutic twenty-four hours before exposure to a p53 adenovirus construct A/C/N/53. In treatment 2, the cells were pretreated with the p53 adenovirus construct and then later contacted with the anti-cancer chemotherapeutic. In treatment 3, the cells were contacted simultaneously with both the anti-cancer chemotherapeutic and the p53 adenovirus.

All cell lines were obtained from ATCC (Rockville, Md.). SCC-9, SCC-15, and SCC-25 head and neck tumor cells (p53$^{null}$) were cultured in a 1:1 mixture of DMEM and Ham's F-12 (GIBCO/Life Technologies, Grand Island, N.Y.) with 10% fetal calf serum (FCS; Hyclone, Logan, Utah), 0.4 μg/ml hydrocortisone (Sigma Chem. Co., St. Louis, Mo.), and 1% nonessential amino acids (GIBCO) at 37° C. and 5% $CO_2$. SK-OV-3 human ovarian tumor cells (p53$^{null}$) and DU-145 human prostate tumor cells (p53$^{mut}$) were cultured in Eagle's MEM plus 10% FCS at 37° C. and 5% $CO_2$. MDA-MB-231 human mammary tumor cells (p53$^{mut}$) were cultured in DMEM (GE3CO) with 10% fetal calf serum (Hyclone) at 37° C. and 5% $CO_2$. MDA-MB-468 human mammary tumor cells (p53$^{mut}$) were cultured in Leibovitz's L-15 medium (GEBCO) containing 10% FCS at 37° C., no $CO_2$.

MDA-MB-231 mammary tumor cells carry an Arg-to-Lys mutation in codon 280 of the p53 gene and express mutant p53 (Bartek (1990) supra). DU-145 prostate tumor cells carry two p53 mutations on different chromosomes, a Proto-Leu mutation in codon 223 and a Val-to-Phe mutation in codon 274 (Isaacs (1991) Cancer Res. 51:4716–4720), and express mutant p53. SK-OV-3 ovarian tumor cells are p53-null (Yaginuma (1992) Cancer Res. 52:4196–4199). SCC-9 cells have a deletion between codons 274 and 285 resulting in a frame shift mutation; no immunoreactive p53 protein is detectable in SCC-9 nuclei (Jung (1992) Cancer Res. 52:6390–6393; Caamano (1993) Am J. Pathol. 142:1131–1139; Min (1994) Eur. J. Cancer 30B:338–345). SCC-15 cells have an insertion of 5 base pairs between codons 224 and 225; they produce low levels of p53 mRNA, but no detectable p53 protein (Min (1994) supra). SCC-25 cells have loss of heterozygosity (LOH) at chromosome 17 and a 2 base pair deletion in codon 209 on the remaining allele; p53 mRNA is not detectable in SCC-25 cells and no immunoreactive p53 protein is observed in their nuclei (Caamano (1993) supra). Approximately 1.5×10$^4$ cells in culture medium (as described in example 1) were added to each well on a 96 well microtitre plate and cultured for about 4 hours at 37° C. and 5% $CO_2$.

Construction and propagation of the human wild-type p53 and E. coli galactosidase (beta-gal) adenoviruses (Ad) have been described previously (Wills (1994) supra). The concentration of infectious viral particles was determined by measuring the concentration of viral hexon protein positive 293 cells after a 48 hr. infection period (Huyghe (1995) supra). C.I.U. is defined as cellular infectious units. p53-expressing adenoviruses were administered in phosphate buffer (20 mM $NaH_2PO_4$, pH 8.0, 130 mM NaCl, 2 mM $MgCl_2$, 2% sucrose). The drug, the p53 adenovirus, or the appropriate vehicle/buffer was added to each well. For in vitro studies with p53 Ad, cells were plated at a density of 1.5×10$^4$ cells/well on a 96-well plate and cultured for 4 hrs. at 37° C. and 5% $CO_2$. Drug, p53 Ad, or the appropriate vehicle was added to each well and cell culture was continued overnight. Then drug, p53 Ad, or the appropriate vehicle was added to each well. Cell culture was continued for an additional 2 days.

Cell death was then quantitated according to the MTT assay as described by Mosmann (1983) J. Immunol. Meth., 65: 55–63. Briefly, approximately 25 μl of 5 mg/ml MTT vital dye [3-(4,5 dimethylthiazol-2yl)-2,5-diphenyltetrazolium bromide] was added to each well and allowed to incubate for 3–4 hrs. at 37° C. and 5% $CO_2$. Then 100 μl of 10% SDS detergent was added to each well and allowed to incubate overnight at 37° C. and 5% $CO_2$. Signal in each well was then quantitated using a Molecular devices microtiter plate reader.

In all cases, using cisplatin (see Table 6 for summary results), doxorubicin (see Table 7 for summary results), 5-FU, methotrexate, and etoposide, the combination therapy was more effective at killing tumor cells than either agent alone. The combination of methotrexate and p53 Ad was tested in one cell line. When SCC-15 cells were treated with 0.7 μM methotrexate 24 hours before 5 m.o.i. p53 Ad, the combined antiproliferative effect of the two drugs was only 5% more than with p53 Ad alone, although this difference was statistically significant (p≦0.003). Pretreatment of DU-145 cells with 2.6 μM etoposide 24 hours before 5 or 10 m.o.i. p53 Ad resulted in greater combined efficacy over either drug alone ($p \leq 0.0001$). When SCC-15 cells were treated with 0.3 µM etoposide 24 hours before 5 m.o.i. p53 Ad, the combined antiproliferative effect of the two drugs was only 5% more than with p53 Ad alone, although this difference was also statistically significant ($p \leq 0.003$). The combination of tumor suppressor gene therapy and anti-neoplastic agents did not demonstrate antagonistic effects.

Figure 9:
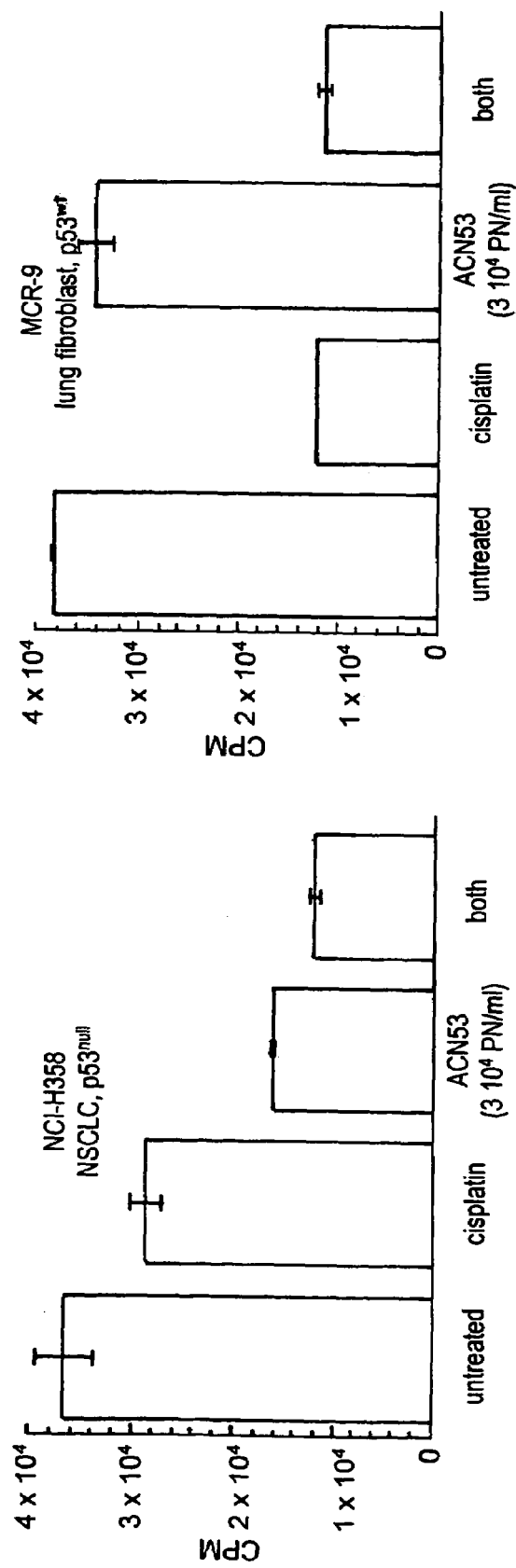
FIG. 9. Comparison of combination p53 and cisplatin therapy on normal and tumor cells.

In a second experiment, the efficacy of treatment of normal cells (MRC-9 cells) was compared with tumor cells (FIG. 9). In this experiment, growth was assayed as $^3$H-thymidine incorporation rather than the MTT assay. The normal cells (diploid fibroblast MRC-9 cells) did not show more pronounced effects with combination treatment. As would be expected, the effect of tumor suppressor alone was negligible in normal cells and highly significant in tumor cells. In contrast, the anti-cancer chemotherapeutic alone (e.g., cisplatin, doxorubicin, 5-FU, methotrexate, and etoposide) was more effective in normal cells than cancer cells (see FIG. 9).

Vitro Cell Dev Biol Anim. 31:55–61); Hep G2, a human hepatocellular carcinoma with p53 wild-type (ibid); and, SK-HEP-1, a human liver adenocarcinoma with p53 wild-type (Lee (1995) FEBS Lett. 368:348–352). Cell viability measured with the live cell probe calcien AM (Molecular Probes) (see, e.g., Poole (1993) J. Cell Sci. 106:685–691). The substrate calcien AM is cleaved by cellular esterases to generate a fluorescent product.

Cells were plated in 96 well plates ($5 \times 10^3$ cells/well), allowed to adhere overnight, treated in triplicate with dilutions of ACN53 and dilutions of doxorubicin on day 0, such that a dose response curve for doxorubicin treatment was generated with each dose of ACN53. On day 3 media was aspirated and calcien AM in PBS was added to the cells. Fluorescent intensity of each well was determined using fluorescent plate reader. Fluorescent value from wells with no cells were subtracted and data was expressed as the percent viability (fluorescent intensity) compared to

TABLE 6

Anti-proliferative effects of p53 Ad in combination with cisplatin.

| | | | Greater Combined Efficacy? | | |
|---|---|---|---|---|---|
| Cell Line | p53 Protein | Tissue Type | Cisplatin First | p53 Ad First | Simultaneous |
| SK-OV-3 | Null | Ovarian | Yes ($p \leq 0.0001$) | Yes ($p \leq 0.0001$) | Yes ($p \leq 0.0001$) |
| SCC-9 | Null | Head & Neck | Yes ($p \leq 0.0001$) | Yes ($p \leq 0.0001$) | Yes ($p \leq 0.0001$) |
| SCC-15 | Null | Head & Neck | Yes ($p \leq 0.0001$) | ND | ND |
| SCC-25 | Null | Head & Neck | Yes ($p \leq 0.0001$) | Yes ($p \leq 0.0001$) | Yes ($p \leq 0.0001$) |
| MDA-MB-468 | Mutant | Breast | Yes ($p \leq 0.0001$) | ND | Yes ($p \leq 0.0001$) |
| MDA-MB-231 | Mutant | Breast | Yes ($p \leq 0.0002$) | Yes ($p \leq 0.0001$) | Yes ($p \leq 0.0001$) |

ND = not done

TABLE 7

Anti-proliferative effects of p53 Ad in combination with doxorubicin.

| | | | Greater Combined Efficacy? | | |
|---|---|---|---|---|---|
| Cell Line | p53 Protein | Tissue Type | Dox First | p53 Ad First | Simultaneous |
| SK-OV-3 | Null | Ovarian | Yes ($p \leq 0.0001$) | Yes ($p \leq 0.0001$) | Yes ($p \leq 0.0001$) |
| SCC-9 | Null | Head & Neck | Yes ($p \leq 0.0001$) | Yes ($p \leq 0.0001$) | Yes ($p \leq 0.0001$) |
| SCC-15 | Null | Head & Neck | Yes ($p \leq 0.0001$) | Yes ($p \leq 0.0001$) | Yes ($p \leq 0.0001$) |
| SCC-25 | Null | Head & Neck | Yes ($p \leq 0.0001$) | Yes ($p \leq 0.0001$) | Yes ($p \leq 0.0001$) |
| DU-145 | Mutant | Prostate | Yes ($p \leq 0.0001$) | Yes ($p \leq 0.0001$) | Yes ($p \leq 0.0001$) |
| MB-231 | Mutant | Breast | Yes ($p \leq 0.0001$) | Yes ($p \leq 0.0001$) | Yes ($p \leq 0.0001$) |

Doxorubicin and p53 Effects on Human Hepatocellular Carcinoma

The following example details the ability of a p53 expressing adenovirus of the invention in combination with doxorubicin to treat neoplasms, and that the combination therapy was more effective, i.e., was synergistic, at killing tumor cells than either agent alone. The results demonstrate a synergistic interaction between the p53 expressing vector of the invention (ACN53) and doxorubicin.

Doxorubicin (Adriamycin) and p53 (ACN53, the recombinant adenovirus construct expressing the human wild-type p53 transgene) were administered to the following cell lines: HLE, a human hepatocellular carcinoma cell line (Hsu (1993) Carcinogenesis 14:987–992; Farshid (1992) J. Med. Virol. 38:235–239; Dor (1975) Gann. 66:385–392), with a mutated p53; HLF, a human hepatocellular carcinoma cell line with a mutated p53 (ibid); Hep 3B, a human hepatocellular carcinoma with a null p53 (Hasegawa (1995) In untreated control wells. $ED_{50}$ values were used to generate isobologram plots to assess the interaction between ACN53 and doxorubicin.

Isobologram analysis for each cell line showed a synergistic interaction between the p53 expressing vector of the invention (ACN53) and doxorubicin; this synergy was independent of the p53 status of the cell line. Note, however, the $ED_{50}$ for ACN53 in the absence of doxorubicin is higher in the p53 wild-type cell lines than in the p53 altered lines.

In another similar experiment, HLE cells were plated in 96 well plates ($5 \times 10^3$ cells/well); allowed to adhere overnight; and, treated in triplicate with dilutions of ACN53 and dilutions of doxorubicin such that a dose response curve for doxorubicin treatment was generated with each dose of ACN53. Three groups were used to test the effects on dosing order on the interaction between ACN53 and doxorubicin.

| group | day 0 | day 1 | day 2 | day 3 |
|---|---|---|---|---|
| simultaneous | ACN53, doxorubicin | | | harvest |
| ACN53 first | ACN53 | doxorubicin | | harvest |
| doxorubicin first | doxorubicin | ACN 53 | | harvest |

Cells were incubated for 3 days after first treatment. Media was aspirated and calcien AM in PBS was added to the cells. Fluorescent intensity of each well was determined using fluorescent plate reader. Fluorescent value from wells with no cells were subtracted and data was expressed as the percent viability (fluorescent intensity) compared to untreated control wells. $ED_{50}$ values were used to generate isobologram plots to assess the interaction between ACN53 and doxorubicin. Isobologram analysis for each dosing regimen showed similar interaction, consistent with synergy, between ACN53 and doxorubicin in HLE cells that was independent of the dosing order of the treatment.

p53 With Chemotherapeutic Drugs In Vivo

The effect of the clinically-relevant anti-cancer drugs cisplatin, doxorubicin, and 5-fluorouracil (5-FU), in combination with a tumor suppressor vector of the invention (A/C/N/53), was further investigated in vivo.

C.B. 17/ICR-scid mice were purchased from Taconic Farms (Germantown, N.Y.) or Charles River Laboratories (Wilmington, Mass.). Athymic nu/nu mice were purchased from Charles River Laboratories. All mice were maintained in a VAF-barrier facility and all animal procedures were performed in accordance with the rules set forth in the N.I.H. Guide for the Care and Use of Laboratory Animals. Tumor volumes for different treatment groups on each day were compared by Student's t test using Statview II software (Abacus Concepts, Berkeley, Calif.). Tumor growth curves were constructed to show mean tumor volume±s.e.m. There were normally ten mice per group.

SK-OV-3 Ovarian Tumor Model:

Established intraperitoneal SK-OV-3 tumors were treated with intraperitoneal doses of vehicles, p53 Ad, cisplatin, or both drugs. Mice were given six injections of p53 Ad over a period of two weeks. The total virus dose was $1.5 \times 10^9$ C.I.U. ($3.1 \times 10^{10}$ viral particles).

Cisplatin efficacy: Female scid mice were injected with $5 \times 10^6$ SK-OV-3 ovarian tumor cells, I.P., on day 0. Mice were dosed I.P. on days 6, 8, 10, 13, 15, and 17 (p53 Ad only on D17). Mice received 0.2 ml total volume (0.1 ml cisplatin vehicle or cisplatin plus 0.1 ml Ad buffer or p53 Ad). The p53 Ad dose was $2.5 \times 10^8$ C.I.U./mouse/day ($5.2 \times 10^9$ viral particles). The cisplatin dose was 2 mg/kg/day. Tumors were harvested and weighed on day 20.

Mice in one treatment group received five doses of cisplatin simultaneously with the first five p53 Ad doses. This dose of intraperitoneal p53 Ad reduced mouse tumor burden only 17% by day 20 ($p \leq 0.01$). However, when combined with cisplatin, p53 Ad caused a 38% decrease in tumor burden as compared to cisplatin alone ($p \leq 0.0008$). Mice treated with drug vehicles or with p53 Ad alone had bloody ascites and invasive tumor nodules in the diaphragm muscle. These symptoms were absent in the mice treated with cisplatin alone or cisplatin with p53 Ad.

Cisplatin/Paclitaxel efficacy: Female scid mice were injected with $2.5 \times 10^6$ SK-OV-3 ovarian tumor cells, I.P., on day 0. Mice were dosed I.P. on days 7, 9, 11, 16, and 18. Mice received 0.3 ml total volume (0.1 ml cisplatin vehicle or cisplatin plus 0.1 ml paclitaxel vehicle or paclitaxel pus 0.1 ml Ad buffer or p53 Ad). The p53 Ad dose was $2.5 \times 10^8$ C.I.U./mouse/day ($5.2 \times 10^9$ viral particles). The cisplatin dose was 0.5 mg/kg/day. The paclitaxel dose was 1 mg/kg/day. Tumors were harvested and weighed on day 30. n=7=10 mice per group.

In this second study, SK-OV-3 ovarian tumors were treated with intraperitoneal doses of vehicles, p53 Ad, cisplatin plus paclitaxel, or all three drugs simultaneously. The combination of all three drugs reduced tumor burden 34% more than the combination of cisplatin plus paclitaxel, demonstrating the enhanced efficacy of the three drug combination ($p \leq 0.0006$).

DU-145 Prostate Tumor Model:

Cisplatin Efficacy:

Intraperitoneal DU-145 tumors were treated with intraperitoneal doses of vehicles, p53 Ad, cisplatin, or both drugs. Male scid mice were injected with $2.5 \times 10^6$ DU-145 cells, I.P., on day 0. Mice were dosed I.P. on days 7, 9, 11, 14, and 16. Mice received 0.2 ml total volume (0.1 ml cisplatin vehicle or cisplatin plus 0.1 ml Ad buffer or p53 Ad). The p53 Ad dose was $8.3 \times 10^8$ C.I.U./mouse/day ($2.9 \times 10^{10}$ PN). The cisplatin dose was 1 mg/kg/day. Tumors were harvested and weighed on day 22. The combination of p53 Ad and cisplatin had greatly enhanced anti-tumor efficacy compared to either drug alone ($p \leq 0.0004$).

MDA-MB-468 Mammary Tumor Model:

Cisplatin Efficacy:

Established MDA-MB-468 tumors were treated with vehicles, p53 Ad, cisplatin, or both drugs. Female scid mice were injected with $1 \times 10^7$ MDA-MB-468 cells into the mammary fat pad, 11 days before the start of dosing on day 0. The intraperitoneal cisplatin dose was 1 mg/kg/day. The intratumoral p53 Ad dose was $8.3 \times 10^8$ CIU/mouse/day ($2.9 \times 10^{10}$ viral particles) given simultaneously on days 0–4. p53 Ad had enhanced efficacy when combined with cisplatin (days 8–31, $p \leq 0.0004$).

Doxorubicin Efficacy:

In a second experiment, MDA-MB-468 tumors were treated with vehicles, p53 Ad, doxorubicin, or both drugs. Female nude mice were injected with $1 \times 10^7$ MDA-MB-468 cells subcutaneously 12 days prior to the start of dosing on day 0. The intraperitoneal doxorubicin dose was 4 mg/kg/day on days 0, 2, 7, and 9. The intratumoral p53 Ad dose was $5 \times 10^8$ CIU/mouse/day ($1.03 \times 10^{10}$ viral particles) on days 0–4 and 7–11.

p53 Ad had greater efficacy when administered in combination with doxorubicin (days 14–24, $p \leq 0.05$).

SCC-15 Head and Neck Tumor Model:

5-Fluorouracil Efficacy:

Subcutaneous SCC-15 tumors were treated with vehicles, p53 Ad, 5-fluorouracil (5-FU), or both drugs. Scid mice were injected with $5 \times 10^6$ SCC-15 cells subcutaneously 7 days prior to the start of dosing on day 0. The intraperitoneal 5-fluorouracil dose was 50 mg/kg/day in 40% hydroxypropyl-beta-cyclodextran (Cerestar Inc., Hammond, Ind.) given I.P. on days 0, 7, and 14 (once a week for 3 weeks). The p53 Ad dose was $2 \times 10^8$ CIU/mouse/day ($4 \times 10^9$ viral particles), on days 0, 1, 7, 8, 14, and 15 (6 intratumoral injections over a period of 3 weeks). The 5-FU dose of 50 mg/kg was given. The combination of p53 Ad and 5-FU resulted in greater antitumor activity than when either drug was used alone ($p \leq 0.04$).

p53 With FPT Inhibitor

The effect of a farnesyl protein transferase inhibitor in combination with a tumor suppressor vector designated A/C/N/53 was investigated in vitro. The following examples detail the ability of a p53 expressing adenovirus of the invention in combination with the FPT inhibitor designated "FPT39," as described in International Application WO 97/23478, filed Dec. 19, 1996, where FPT39 is designated compound "39.0," see pg 95 of WO 97/23478) to treat neoplasms, and that for combination therapy against prostate tumor cells and mammary tumor cells was more effective at killing tumor cells than either agent alone.

Anti-Proliferative Efficacy of rAd5/p53 and FPT39 Against SK-OV-3 Ovarian Tumor

Methods: SK-OV-3 human ovarian tumor cells ($p53^{null}$) were aliquoted into 96-well plates at a density of 250 cells per well in Eagle's MEM plus 10% fetal bovine serum. Cells were then incubated at 37° C. and 5% $CO_2$ for 4 hours. FPT39 or drug vehicle was added to each well and cell culture was continued for 3 days. After 3 days, untreated cells in some wells were counted in order to calculate the amount of rAd5/p53 to add. Then rAds/p53 or drug vehicle was added to each well and cell culture was continued for another 3 days. Cell proliferation was measured using the MTT assay. Briefly, 25 ul of 5 mg/ml MTT vital dye [3-(4,5 dimethylthiazol-2-yl)-2,5-diphenyltetrazolium bromide] was added to each well and allowed to incubate for 3–4 hrs. at 37° C. and 5% $CO_2$. Then, 100 ul of 10% SDS detergent was added to each well and the incubation was continued overnight. Fluorescence in each well was quantitated using a Molecular Devices microtiter plate reader. Cell proliferation data was analyzed using the Thin Plate Spline statistical methodology of O'Connell and Wolfinger (1997) *J. Comp. Graph. Stat.* 6: 224–241

Results: rAd5/p53 and FPT39 had additive efficacy in inhibiting cell growth. Neither synergism ($p>0.05$) nor antagonism ($p>0.05$) were demonstrated in this experiment.

Anti-Proliferative and Synergistic Efficacy of rAd5/p53 and FPT39 (FPT Inhibitor) Against DU-145 Prostate Tumor Cells Methods: DU-145 human prostate tumor cells ($p53^{mut}$) were treated with FPT39 or drug vehicle, and rAd5/p53, and the cell cultures were subsequently analyzed, as described above for the SK-OV-3 human ovarian tumor cells. The experiment was repeated twice.

Results: Experiment 1: rAd5/p53 and FPT39 had additive efficacy in inhibiting cell growth. Neither synergism ($p>0.05$) nor antagonism ($p>0.05$) were demonstrated in this experiment.

Experiment 2: rAd5/p53 and FPT39 had synergistic efficacy ($p=0.0192$). These results demonstrate that rAd5/p53 and FPT39 can interact and have synergistic efficacy against prostate tumor cell proliferation.

Anti-proliferative and Synergistic Efficacy of rAd5/p53 and FPT39 (FPT Inhibitor) Against MDA-MB-231 Mammary Tumor Cells Methods: MDA-MB-231 human breast cancer cells ($p53^{mut}$) were treated with FPT39 or drug vehicle, and rAd5/p53, and the cell cultures were subsequently analyzed, as described above for the SK-OV-3 human ovarian tumor cells. The experiment was repeated twice.

Results: Experiment 1: rAd5/p53 and FPT39 had additive efficacy. Neither synergism ($p>0.05$) were demonstrated in this experiment.

Experiment 2: rAd5/p53 and FPT39 had additive efficacy over most of the response surface. However, synergism was evident at isoboles greater that or equal to 70 (i.e., less than 30% of cells killed, $p=0.0001$). These results demonstrate that rAd5/p53 and FPT39 can interact and have synergistic efficacy against human breast cancer cell proliferation.

Example 7

Immune Response Profile in Patients with Metastatic Hepatic Carcinomas Treated with Adenovirus Vector Carrying p53

The invention provides for the combined in vivo administration of nucleic acid expressing p53 and other chemotherapeutic agents in the treatment of neoplasms. The following example details the ability of the p53 expressing adenovirus of the invention to increases the levels of tumor-killing lymphocytes found within a human liver carcinoma.

The aim of this study was to characterize the genotypes and phenotypes of the tumor infiltrating lymphocytes (TILs) in metastatic liver carcinomas from the colon harboring p53 mutations (for discussion TILs, see, e.g., Wang (1997) *Mol. Med.* 3:716–731; Marrogi (1997) *Int. J. Cancer* 74:492–501). A total of 16 patients were treated in a dose escalating manner, $10^9$–$10^{11}$ particles, through hepatic artery canalization with an adenovirus vector carrying wild type p53 gene. A total of four biopsies from each patient was obtained 3 to 7 days after administering the adenoviral vector. Immunohistochemical analysis were performed on the frozen tissues obtained from normal liver and tumor-host tissue interface sites. Computer assisted image analysis was performed to quantitate immunoreactivity to the following monoclonal antibodies: CD3, CD4, CD8, CD25, CD28, CD56, HLA-DR, IFN-gamma, TNF-alpha and IL-2. An increase in TILs ($CD3^+$ and $CD4^+$) population was observed with the maximum at $7.5 \times 10^{10}$ particles. At higher doses, a decrease in $CD3^+$ and $CD4^+$ population was observed. An inverse correlation was observed for $CD8^+$ cells. At the highest dose ($2.5 \times 10^{11}$) an increase in the $CD3^+$, $CD4^+$ and $CD8^+$ population was observed in the tumor as compared to the normal. These results demonstrate that delivery of high doses of adenovirus particles results in increased TILs composed of $CD4^+$ and $CD8^+$ population.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed:

1. A method of treating mammalian cancer cells deficient in functional p53, said method comprising contacting said cancer cells with a recombinant adenoviral vector comprising a nucleic acid encoding p53 tumor suppressor protein, which nucleic acid is expressed in said cells, and also contacting said cells with the polyprenyl-protein transferase inhibitor FPT39, such that one or more disease characteristics of the cells are ameliorated, wherein the mammalian cancer cells are human breast, colorectal, pancreatic, or prostate cancer cells.

2. The method of claim 1, wherein said nucleic acid is delivered by a recombinant adenoviral vector comprising a partial or total deletion of a protein IX DNA and comprising a nucleic acid encoding a wild-type p53 protein.

3. The method of claim 1, wherein said recombinant adenoviral vector comprises the adenovirus type 2 major late promoter or the human CMV promoter, the adenovirus type 2 tripartite leader cDNA and a human p53 cDNA, which are operably linked.

4. The method of claim 1, wherein said cells are first contacted with said recombinant adenoviral vector comprising a nucleic acid encoding p53 and are subsequently contacted with said FPT39.

5. The method of claim 1, wherein said cells are first contacted with said FPT39 and subsequently contacted with said recombinant adenoviral vector comprising a nucleic acid encoding p53.

6. The method of claim 1, wherein said cells are simultaneously contacted with said FPT39 and with said recombinant adenoviral vector comprising a nucleic acid encoding p53.

7. The method of claim 1, wherein said recombinant adenoviral vector comprising a nucleic acid encoding p53 is dispersed in a pharmacologically acceptable excipient.

8. The method of claim 1, wherein said recombinant adenoviral vector comprising a nucleic acid encoding p53 and said FPT39 are dispersed in a single composition.

9. The method of claim 1, wherein said contacting cells with a recombinant adenoviral vector comprising a nucleic acid encoding p53 comprises contacting said cells with said recombinant adenoviral vector comprising a nucleic acid encoding p53 in a multiplicity of treatments each separated by at least about 6 hours.

10. A method of treating human breast, colorectal, pancreatic, or prostate cancer cells in a mammal, the method comprising administering to the mammal an adenoviral vector comprising a nucleic acid encoding a p53 tumor suppressor protein, which nucleic acid is expressed in the cells, and also administering to the mammal the polyprenyl-protein transferase inhibitor FPT39, such that one or more disease characteristics of the cancer cells are ameliorated.

11. A method of treating human breast, colorectal, pancreatic, or prostate cancer cells in vitro, the method comprising contacting the cancer cells with an adenoviral vector comprising a nucleic acid encoding a p53 tumor suppressor protein, which nucleic acid is expressed in the cells, and also contacting the cells with the polyprenyl-protein transferase inhibitor FPT39, such that one or more disease characteristics of the cancer cells are ameliorated.

12. The method according to claim 10, wherein the cancer cells comprise human breast cancer cells.

13. The method according to claim 10, wherein the cancer cells comprise human colorectal cancer cells.

14. The method according to claim 10, wherein the cancer cells comprise human pancreatic cancer cells.

15. The method according to claim 10, wherein the cancer cells comprise human prostate cancer cells.

16. The method according to claim 11, wherein the cancer cells comprise human breast cancer cells.

17. The method according to claim 11, wherein the cancer cells comprise human colorectal cancer cells.

18. The method according to claim 11, wherein the cancer cells comprise human pancreatic cancer cells.

19. The method according to claim 11, wherein the cancer cells comprise human prostate cancer cells.

* * * * *